United States Patent
Haas et al.

(10) Patent No.: US 11,395,799 B2
(45) Date of Patent: Jul. 26, 2022

(54) PREPARATION AND STORAGE OF LIPOSOMAL RNA FORMULATIONS SUITABLE FOR THERAPY

(71) Applicant: BioNTech SE, Mainz (DE)

(72) Inventors: Heinrich Haas, Mainz (DE); Sebastian Hörner, Mainz (DE); Isaac Hernan Esparza Borquez, Mainz (DE); Thomas Michael Hiller, Mainz (DE); Ferdia Bates, Mainz (DE)

(73) Assignee: BioNTech SE, Mainz (DE)

( * ) Notice: Subject to any disclaimer, the term of this patent is extended or adjusted under 35 U.S.C. 154(b) by 0 days.

(21) Appl. No.: 16/757,054

(22) PCT Filed: Oct. 18, 2018

(86) PCT No.: PCT/EP2018/078587
§ 371 (c)(1),
(2) Date: Apr. 17, 2020

(87) PCT Pub. No.: WO2019/077053
PCT Pub. Date: Apr. 25, 2019

(65) Prior Publication Data
US 2020/0246267 A1      Aug. 6, 2020

Related U.S. Application Data

(60) Provisional application No. 62/574,965, filed on Oct. 20, 2017.

(51) Int. Cl.
*A61K 9/127* (2006.01)
*B82Y 5/00* (2011.01)
(Continued)

(52) U.S. Cl.
CPC .......... *A61K 9/1272* (2013.01); *A61K 31/713* (2013.01); *A61K 48/00* (2013.01); *B82Y 5/00* (2013.01)

(58) Field of Classification Search
CPC .............................. A61K 9/1272; A61K 9/127
See application file for complete search history.

(56) References Cited

U.S. PATENT DOCUMENTS

| 2005/0002998 | A1* | 1/2005 | Chang | A61K 47/6911 424/450 |
| 2005/0064026 | A1* | 3/2005 | Garidel | A61K 9/1272 424/450 |

(Continued)

FOREIGN PATENT DOCUMENTS

| CN | 1492756 A | 4/2004 |
| CN | 102144973 A | 8/2011 |

(Continued)

OTHER PUBLICATIONS

Jule Clement, Karin Kiefer, Andrea Kimpfler, Patrick Garidel, Regine Peschka-Suss. "Large-scale production of lipoplexes with long shelf-life." European Journal of Pharmaceutics and Biopharmaceutics, vol. 59, 2005, pp. 35-43. (Year: 2005).*

(Continued)

*Primary Examiner* — Isaac Shomer
(74) *Attorney, Agent, or Firm* — Choate, Hall & Stewart LLP; Brenda Herschbach Jarrell; Michael A. Shinall

(57) ABSTRACT

The present disclosure relates to methods for preparing RNA lipoplex particles for delivery of RNA to target tissues after parenteral administration, in particular after intravenous administration, and compositions comprising such RNA lipoplex particles. The present disclosure also relates to methods which allow preparing RNA lipoplex particles in an industrial GMP-compliant manner. Furthermore, the present disclosure relates to methods and compositions for storing RNA lipoplex particles without substantial loss of the product quality and, in particular, without substantial loss of RNA activity.

31 Claims, 45 Drawing Sheets

(51) Int. Cl.
    *A61K 48/00* (2006.01)
    *A61K 31/713* (2006.01)

(56) References Cited

U.S. PATENT DOCUMENTS

| | | | |
|---|---|---|---|
| 2008/0196762 | A1 | 8/2008 | Mallett et al. |
| 2011/0165223 | A1* | 7/2011 | Sgouros ......... A61K 39/001189 424/450 |
| 2021/0161818 | A1 | 6/2021 | Haas et al. |

FOREIGN PATENT DOCUMENTS

| | | | | |
|---|---|---|---|---|
| CN | 102727436 | A | 10/2012 | |
| CN | 103194489 | A | 7/2013 | |
| CN | 103906504 | A | 7/2014 | |
| CN | 104302276 | A | 1/2015 | |
| CN | 107072945 | A | 8/2017 | |
| EP | 2830593 | A1 | 2/2015 | |
| WO | WO-0105373 | A1 * | 1/2001 | ........... A61K 9/1272 |
| WO | WO-02/066012 | A2 | 8/2002 | |
| WO | WO-2012/112730 | A2 | 8/2012 | |
| WO | WO-2013/143555 | A1 | 10/2013 | |
| WO | WO-2013/143683 | A1 | 10/2013 | |
| WO | WO-2016/045732 | A1 | 3/2016 | |
| WO | WO-2016045732 | A1 * | 3/2016 | ........... A61K 9/1272 |
| WO | WO-2016138175 | A1 * | 9/2016 | ........... A61K 9/1682 |
| WO | WO-2016149625 | A1 * | 9/2016 | ........ B01F 15/00149 |
| WO | WO-2016156398 | A1 * | 10/2016 | ........... A61K 31/675 |
| WO | WO-2019/077053 | A1 | 4/2019 | |

OTHER PUBLICATIONS

Tiago Albertini Balbino, Adriano Rodrigues Azzoni, Lucimara Gaziola de la Torre. "Microfluidic devices for continuous production of pDNA/cationic liposome complexes for gene delivery and vaccine therapy." Colloids and Surfaces B: Biointerfaces 111, vol. 2013, pp. 203-210. (Year: 2013).*

O Zelphati, C Nguyen, M Ferrari, J Feigner, Y Tsai and PL Felgner. "Stable and monodisperse lipoplex formulations for gene delivery." Gene Therapy, vol. 5, 1998, pp. 1272-1282. (Year: 1998).*

Linde Schoenmaker, Dominik Witzigmann, Jayesh A. Kulkarni, Rein Verbeke, Gideon Kersten, Wim Jiskoot,, Daan J.A. Crommelin. "mRNA-lipid nanoparticle COVID-19 vaccines: Structure and stability." International Journal of Pharmaceutics 601 (2021) 120586, pp. 1-13. (Year: 2021).*

International Search Report for PCT/EP2018/078587 (Preparation and Storage of Liposomal RNA Formulations Suitable for Therapy, filed Oct. 18, 2018) received by ISA/EP, 5 pages (dated Apr. 25, 2019).

Written Opinion for PCT/EP2018/078587 (Preparation and Storage of Liposomal RNA Formulations Suitable for Therapy, filed Oct. 18, 2018) received by ISA/EP, 8 pages (dated Apr. 25, 2019).

Verbeke, R., et al., Co-delivery of nucleoside-modified mRNA and TLR agonists for cancer immunotherapy: Restoring the immunogenicity of immunosilent mRNA, J Control Release, 266:287-300 (2017).

* cited by examiner

PREPARATION AND STORAGE OF LIPOSOMAL RNA FORMULATIONS SUITABLE FOR THERAPY

RELATED APPLICATIONS

This application is a 35 U.S.C. § 371 National Phase Entry Application of International Application No. PCT/EP2018/078587 filed on Oct. 18, 2018, which claims the benefit of and priority to U.S. Provisional Application Ser. No. 62/574,965, filed on Oct. 20, 2017, each of which are incorporated herein by reference in their entirety.

TECHNICAL FIELD

The present disclosure relates to methods for preparing RNA lipoplex particles for delivery of RNA to target tissues after parenteral administration, in particular after intravenous administration, and compositions comprising such RNA lipoplex particles. The present disclosure also relates to methods which allow preparing RNA lipoplex particles in an industrial GMP-compliant manner. Furthermore, the present disclosure relates to methods and compositions for storing RNA lipoplex particles without substantial loss of the product quality and, in particular, without substantial loss of RNA activity. RNA lipoplex particle formulations described herein can be frozen or dehydrated by freeze-drying, spray-drying or related methods, enabling to obtain extended shelf-life of the products in comparison to liquid storage. The RNA lipoplex particles in one embodiment comprise single-stranded RNA such as mRNA which encodes a peptide or protein of interest, such as a pharmaceutically active peptide or protein. The RNA is taken up by cells of a target tissue and the RNA is translated into the encoded peptide or protein, which may exhibit its physiological activity. The peptide or protein of interest may be a peptide or protein comprising one or more epitopes for inducing or enhancing an immune response directed against the one or more epitopes. The methods and compositions described herein are suitable for use in a manner that complies with the requirements for pharmaceutical products, more specifically that complies with the requirements for GMP manufacturing and the requirements for the quality of pharmaceutical products for parenteral application.

BACKGROUND

The use of RNA for delivery of foreign genetic information into target cells offers an attractive alternative to DNA. The advantages of using RNA include transient expression and a non-transforming character. RNA does not need to enter the nucleus in order to be expressed and moreover cannot integrate into the host genome, thereby eliminating the risk of oncogenesis. RNA may be delivered by so-called lipoplex formulations, in which the RNA is bound to liposomes composed of a mixture of a cationic lipid and helper lipid to form injectable nanoparticle formulations. The development of formulations for the delivery of biologically active RNA to a target tissue, even after storage of the formulations, is, however, an unmet need. In addition, the development of methods for GMP-compliant manufacturing of injectable RNA lipoplex particle formulations where long shelf-life is provided is still an unmet need Thus, there is a need of providing formulations for the delivery of biologically active RNA to a target tissue where the delivered RNA is efficiently translated into the peptide or protein it codes for. Furthermore, there is a need of providing such formulations which are shelf-stable without substantial loss of the product quality and, in particular, without substantial loss of biological activity of the RNA.

The inventors surprisingly found that the RNA lipoplex particle formulations described herein fulfill the above mentioned requirements.

SUMMARY

I. Methods for Preparing RNA Lipoplex Particles, RNA Lipoplex Particles and Compositions Comprising RNA Lipoplex Particles In a first aspect, the present disclosure relates to methods for preparing RNA lipoplex particles with improved biological activity, RNA lipoplex particles prepared according to the disclosure and compositions comprising such RNA lipoplex particles. The RNA lipoplex particles and compositions comprising RNA lipoplex particles are useful for delivery of RNA to a target tissue after parenteral administration, in particular after intravenous administration. The RNA lipoplex particles are prepared using liposomes that are obtained by injecting a highly concentrated solution of the lipids in ethanol into water or a suitable aqueous phase. In one embodiment, the RNA lipoplex product is characterized by a specific pattern in x-ray scattering, where a single Bragg peak at about 1 $nm^{-1}$ is observed, where the peak width is smaller than 0.2 $nm^{-1}$.

In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). The concentration of DOPE in the lipid mixture is higher than the equilibrium solubility of the DOPE in ethanol alone. At room temperature, DOPE alone has a solubility of about 50 mM, together with the DOTMA it has a solubility of 100 mM or higher. Lipid solutions to form liposomes, from which highly active lipoplexes are obtained may have a total lipid concentration of 270 mM or above (e.g., DOPE at 90 mM or above). Solutions of even higher concentration in ethanol may be obtained by increasing the temperature. Liposomes obtained from lipid solutions where the concentration of the DOPE is above the equilibrium solubility are significantly larger than the liposomes from lipid solutions where the concentration of the DOPE is at the equilibrium solubility and below. The liposome size increases monotonously with the concentration in ethanol.

Liposomes prepared according to the disclosure may be used for preparing RNA lipoplex particles by mixing the liposomes with RNA. In one embodiment, the RNA is incubated with NaCl prior to mixing in order to adjust a certain ionic strength, which is required for increased activity of the lipoplexes. Lipoplexes which are formed from these larger liposomes have significantly higher biological activity, as demonstrated by in vitro and in vivo experiments. These lipoplexes with higher activity can be clearly discriminated from those with lower activity by certain physicochemical parameters, for example (i) a lower peak width of the Bragg peak and (ii) a different separation profile in dispersive analytical methods for size measurements, like field-flow fractionation. Lipoplexes with lower activity are smaller in average. In addition, they have also a different elution profile, which is probably related to parameters like the molecular conformation, shape, and the interactions with the bulk phase.

Accordingly, in this aspect, the disclosure relates to a method of producing a liposome colloid comprising injecting a lipid solution in ethanol into an aqueous phase to produce the liposome colloid, wherein the concentration of at least one of the lipids in the lipid solution corresponds to or is higher than the equilibrium solubility of the at least one lipid in ethanol.

In one embodiment, the method comprises heating the lipid solution to increase the concentration of lipids in the lipid solution. In one embodiment, the lipid solution is heated to a temperature of at least about 40° C., or at least about 60° C.

In one embodiment, the lipid solution is a solution of a mixture of two or more different lipids.

In one embodiment, the concentration of one lipid in the lipid solution corresponds to or is higher than the equilibrium solubility of the lipid in ethanol.

In one embodiment, the total lipid concentration in the lipid solution is from about 180 mM to about 600 mM, from about 300 mM to about 600 mM, or about 330 mM.

In one embodiment, the lipid solution comprises at least one cationic lipid and at least one additional lipid.

In one embodiment, the concentration of an additional lipid in the lipid solution corresponds to or is higher than the equilibrium solubility of the additional lipid in ethanol.

In one embodiment, the at least one cationic lipid comprises 1,2-di-O-octadecenyl-3-trimethylammonium propane (DOTMA) and/or 1,2-dioleoyl-3-trimethylammonium-propane (DOTAP).

In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC).

In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE).

In one embodiment, the molar ratio of the at least one cationic lipid to the at least one additional lipid is from about 10:0 to about 1:9, from about 4:1 to about 1:2, from about 3:1 to about 1:1, or about 2:1.

In one embodiment, the lipid solution comprises DOTMA and DOPE in a molar ratio of from about 10:0 to about 1:9, from about 4:1 to about 1:2, from about 3:1 to about 1:1, or about 2:1.

In one embodiment, the concentration of DOPE in the lipid solution is at least about 60 mM, or at least about 90 mM.

In one embodiment, the lipid solution is injected into the aqueous phase at a stirring velocity of the aqueous phase of from about 50 rpm to about 150 rpm.

In one embodiment, the aqueous phase is water.

In one embodiment, the aqueous phase has an acidic pH. In one embodiment, the aqueous phase comprises acetic acid e.g., in an amount of about 5 mM.

In one embodiment, the method further comprises stirring the liposome colloid.

In one embodiment, the liposome colloid is stirred for about 15 min to about 60 min, or for about 30 min.

The disclosure further relates to a method of producing a liposome colloid comprising injecting a lipid solution comprising DOTMA and DOPE in a molar ratio of about 2:1 in ethanol into water stirred at a stirring velocity of about 150 rpm to produce the liposome colloid, wherein the concentration of DOTMA and DOPE in the lipid solution is about 330 mM.

In one embodiment, the method of producing a liposome does not comprise the step of extruding the liposomes.

The disclosure further relates to a liposome colloid which is obtainable by the method of producing a liposome.

In one embodiment, the liposomes have an average diameter of at least about 250 nm.

In one embodiment, the liposomes have an average diameter that ranges from about 250 nm to about 800 nm.

In one embodiment, the liposomes have a polydispersity index smaller than about 0.5, smaller than about 0.4, or smaller than about 0.3.

In one embodiment, the liposomes are cationic liposomes.

In one embodiment, the liposomes comprise at least one cationic lipid and at least one additional lipid.

In one embodiment, the at least one cationic lipid comprises 1,2-di-O-octadecenyl-3-trimethylammonium propane (DOTMA) and/or 1,2-dioleoyl-3-trimethylammonium-propane (DOTAP).

In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC).

In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE).

In one embodiment, the molar ratio of the at least one cationic lipid to the at least one additional lipid is from about 10:0 to about 1:9, from about 4:1 to about 1:2, from about 3:1 to about 1:1, or about 2:1.

In one embodiment, the liposomes comprise DOTMA and DOPE in a molar ratio of from about 10:0 to about 1:9, from about 4:1 to about 1:2, from about 3:1 to about 1:1, or about 2:1.

The disclosure further relates to a method of preparing RNA lipoplex particles comprising adding the above liposome colloid to a solution comprising RNA.

In one embodiment, in an X-ray scattering pattern the RNA lipoplexes are characterized by a single Bragg peak at about 1 $nm^{-1}$, wherein the peak width is smaller than 0.2 $nm^{-1}$.

In one embodiment, the RNA lipoplex particles have an average diameter that ranges from about 200 to about 800 nm, from about 250 to about 700 nm, from about 400 to about 600 nm, from about 300 nm to about 500 nm, or from about 350 nm to about 400 nm.

The disclosure further relates to a composition comprising RNA lipoplex particles which are obtainable as described above.

In one embodiment, the RNA lipoplex particles comprise at least one cationic lipid and at least one additional lipid.

In one embodiment, the RNA encodes a peptide or protein comprising at least one epitope, wherein the ratio of positive charges to negative charges in the RNA lipoplex particles is from about 1:2 to about 1.9:2, or about 1.3:2.0.

The disclosure further relates to a composition comprising:
  RNA lipoplex particles comprising:
  RNA encoding a peptide or protein comprising at least one epitope, and
  at least one cationic lipid and at least one additional lipid, wherein the ratio of positive charges to negative charges in the RNA lipoplex particles is from about 1:2 to about 1.9:2, or about 1.3:2.0, and
  wherein the RNA lipoplex particles are characterized by a single Bragg peak at about 1 $nm^{-1}$, wherein the peak width is smaller than 0.2 $nm^{-1}$.

In one embodiment, the composition further comprises sodium chloride at a concentration from about 10 mM to about 300 mM, from about 45 mM to about 300 mM, from about 10 mM to about 50 mM, or from about 80 mM to about 150 mM.

In one embodiment, the composition further comprises a buffer.

In one embodiment, the composition further comprises a chelating agent.

In one embodiment, the RNA lipoplex particles described in this aspect under I. have an average diameter that ranges from about 200 to about 800 nm, from about 250 to about 700 nm, from about 400 to about 600 nm, from about 300 nm to about 500 nm, or from about 350 nm to about 400 nm.

In one embodiment, the RNA lipoplex particles have a polydispersity index smaller than about 0.5, smaller than about 0.4, or smaller than about 0.3.

In one embodiment, the at least one cationic lipid comprises 1,2-di-O-octadecenyl-3-trimethylammonium propane (DOTMA) and/or 1,2-dioleoyl-3-trimethylammonium-propane (DOTAP).

In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC).

In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE).

In one embodiment, the molar ratio of the at least one cationic lipid to the at least one additional lipid is from about 10:0 to about 1:9, from about 4:1 to about 1:2, from about 3:1 to about 1:1, or about 2:1.

In one embodiment, the RNA lipoplex particles comprise DOTMA and DOPE in a molar ratio of from about 10:0 to 1:9, from about 4:1 to 1:2, from about 3:1 to about 1:1, or about 2:1 and wherein the charge ratio of positive charges in DOTMA to negative charges in the RNA is from about 1:2 to 1.9:2.

In one embodiment, the chelating agent is ethylenediaminetetraacetic acid (EDTA).

In one embodiment, the EDTA is at a concentration from about 0.25 mM to about 5 mM, or of about 2.5 mM.

In one embodiment, the composition further comprises an adjuvant.

In one embodiment, the composition is formulated for systemic administration.

In one embodiment, the systemic administration is by intravenous administration.

The disclosure further relates to a composition as described for therapeutic use.

II. Methods for Preparing RNA Lipoplex Particles in an Industrial GMP-Compliant Manner In a second aspect, the present disclosure relates to methods which allow preparing RNA lipoplex particles in an industrial GMP-compliant manner.

In one embodiment of the disclosure, a fluid paths system is used for GMP-manufacturing of the pharmaceutical RNA lipoplex particle product, which enables accurate control of the mixing ratio of RNA to liposomes, which is important for product quality. In one embodiment, the fluid path comprises mixing of a liposome solution and an RNA solution in a 1 to 1 (volume/volume) manner, where the concentrations of the components are selected in order to exactly maintain the intended charge ratio. In one embodiment, the RNA is incubated with NaCl prior to mixing in order to adjust a certain ionic strength, which is required for the activity of the lipoplexes. In one embodiment, a Y-type mixing setup is realized, which is fully based on single use materials. Fluid dynamics are optimized to maintain particle characteristics and to avoid clogging. In contrast, when using commercially available microfluidic devices clogging occurs after some time, which makes application for GMP impossible.

In one embodiment, lipoplexes are manufactured by incubating RNA with cationic liposomes, where the mixing ratio and mixing conditions are exactly controlled by using a syringe pump (perfusor pump), where two syringes, one comprising liposomes and one comprising RNA are inserted in syringe pumps, preferentially in parallel into the same pump. Pistons of poth pumps are moved forward by the same driver, thus exactly controlling the relative volumina which are mixed. In the selected process conditions, identical syringes are used for both solutions thus enabling an exact one to one (v/v) mixing condition. By adjusting the concentrations of the two solutions prior to mixing, the ratio between RNA and liposomes (cationic lipid) is then exactly controlled.

Accordingly, in this aspect, the disclosure relates to a method for continuous flow manufacturing of RNA lipoplex particles comprising mixing a solution comprising RNA and a solution comprising cationic liposomes under controlled mixing conditions of the RNA and the cationic liposomes.

In one embodiment, the solution comprising cationic liposomes is the liposome colloid as described above.

In one embodiment, the solution comprising RNA and the solution comprising cationic liposomes are aqueous solutions.

In one embodiment, a flow rate is used which allows mixing of the solution comprising RNA and the solution comprising cationic liposomes.

In one embodiment, the flow is characterized by a Reynolds number of greater than 300, or from about 500 to about 2100.

In one embodiment, the controlled mixing conditions comprise controlling the mixing ratio of the solution comprising RNA and the solution comprising cationic liposomes.

In one embodiment, the controlled mixing conditions comprise controlling the relative volume of the solution comprising RNA and the solution comprising cationic liposomes which are to be mixed.

In one embodiment, the mixing ratio of the RNA and the cationic liposomes is controlled by using identical mixing volume (v/v) of the solution comprising RNA and the solution comprising cationic liposomes and adjusting the concentrations of RNA and cationic liposomes in the respective solutions.

In one embodiment, the controlled mixing conditions are selected to maintain characteristics of the RNA lipoplex particles while avoiding clogging.

In one embodiment, the method comprises using a Y-type or T-type mixing element.

In one embodiment, the Y-type or T-type mixing element has a diameter of from about 1.2 mm to about 50 mm.

In one embodiment, the method comprises using a mixing element, e.g. a Y-type or T-type mixing element, wherein the fluids from two tubes or hoses are brought together and wherein no internal static mixing elements as e.g. split and recombine, staggered herringbone, zigzag or twisted channels, or three-dimensional serpentine are present. Mixing elements can have diameters between 1.2 and 50.0 mm.

In one embodiment, the method comprises using a device, where two syringes, one comprising the solution comprising cationic liposomes and one comprising the solution comprising RNA are inserted in parallel into the same or two holders and pistons of the device are protruded by one or two precision actuator(s). In one embodiment, the method comprises using a syringe pump, where two syringes, one comprising the solution comprising cationic liposomes and one comprising the solution comprising RNA are inserted in parallel into the same pump.

In one embodiment, the method comprises using a pressurized vessel, a membrane pump, a gear pump, a magnetic levitation pump, a peristaltic pump, HPLC/FPLC pumps or any other piston pump, optionally in combination with flow rate sensors optionally with feedback-loop for online-control and real-time adjustment of the flow rate.

In one embodiment, the mixture of the solution comprising RNA and the solution comprising liposomes comprises sodium chloride at a concentration from about 45 mM to about 300 mM, or comprises an ionic strength corresponding to sodium chloride at a concentration from about 45 mM to about 300 mM.

In one embodiment, the RNA solution comprises sodium chloride at a concentration from about 90 mM to about 600 mM, or comprises an ionic strength corresponding to sodium chloride at a concentration from about 90 mM to about 600 mM.

In one embodiment, the mixture of the solution comprising RNA and the solution comprising liposomes has an ionic strength of at least about 50 mM.

In one embodiment, in an X-ray scattering pattern the RNA lipoplexes are characterized by a single Bragg peak at about 1 $nm^{-1}$, wherein the peak width is smaller than 0.2 $nm^{-1}$ In one embodiment, the RNA lipoplex particles have an average diameter that ranges from about 200 to about 800 nm, from about 250 to about 700 nm, from about 400 to about 600 nm, from about 300 nm to about 500 nm, or from about 350 nm to about 400 nm.

The disclosure further relates to a composition comprising RNA lipoplex particles which are obtainable as described above.

In one embodiment, the RNA lipoplex particles comprise at least one cationic lipid and at least one additional lipid.

In one embodiment, the RNA encodes a peptide or protein comprising at least one epitope, wherein the ratio of positive charges to negative charges in the RNA lipoplex particles is from about 1:2 to about 1.9:2, or about 1.3:2.0.

The disclosure further relates to a composition comprising:
RNA lipoplex particles comprising:
RNA encoding a peptide or protein comprising at least one epitope, and
at least one cationic lipid and at least one additional lipid,
wherein the ratio of positive charges to negative charges in the RNA lipoplex particles is from about 1:2 to about 1.9:2, or about 1.3:2.0, and
wherein the RNA lipoplex particles are characterized by a single Bragg peak at about 1 $nm^{-1}$, wherein the peak width is smaller than 0.2 $nm^{-1}$.

In one embodiment, the composition further comprises sodium chloride at a concentration from about 10 to about 300 mM, from about 45 mM to about 300 mM, from about 10 mM to about 50 mM, or from about 80 mM to about 150 mM.

In one embodiment, the composition further comprises a buffer.

In one embodiment, the composition further comprises a chelating agent.

In one embodiment, the RNA lipoplex particles described in this aspect under II. have an average diameter that ranges from about 200 to about 800 nm, from about 250 to about 700 nm, from about 400 to about 600 nm, from about 300 nm to about 500 nm, or from about 350 nm to about 400 nm.

In one embodiment, the RNA lipoplex particles have a polydispersity index smaller than about 0.5, smaller than about 0.4, or smaller than about 0.3.

In one embodiment, the at least one cationic lipid comprises 1,2-di-O-octadecenyl-3-trimethylammonium propane (DOTMA) and/or 1,2-dioleoyl-3-trimethylammonium-propane (DOTAP).

In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC).

In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE).

In one embodiment, the molar ratio of the at least one cationic lipid to the at least one additional lipid is from about 10:0 to about 1:9, from about 4:1 to about 1:2, from about 3:1 to about 1:1, or about 2:1.

In one embodiment, the RNA lipoplex particles comprise DOTMA and DOPE in a molar ratio of from about 10:0 to 1:9, from about 4:1 to 1:2, from about 3:1 to about 1:1, or about 2:1 and wherein the charge ratio of positive charges in DOTMA to negative charges in the RNA is from about 1:2 to 1.9:2.

In one embodiment, the chelating agent is ethylenediaminetetraacetic acid (EDTA).

In one embodiment, the EDTA is at a concentration from about 0.25 mM to about 5 mM, or of about 2.5 mM.

In one embodiment, the composition further comprises an adjuvant.

In one embodiment, the composition is formulated for systemic administration.

In one embodiment, the systemic administration is by intravenous administration.

The disclosure further relates to a composition as described for therapeutic use.

III. Methods and Compositions for Storing RNA Lipoplex Particles

In a third aspect, the present disclosure relates to methods and compositions for storing RNA lipoplex particles without substantial loss of the product quality and, in particular, without substantial loss of RNA activity. In particular, the present disclosure relates to formulations which allow freezing, lyophilization or spray-drying of RNA lipoplex particles without substantial loss of the quality of the RNA lipoplex particles and, in particular, without substantial loss of RNA activity.

RNA lipoplex particle formulations described herein can be frozen or dehydrated by freeze drying, spray-drying or related methods, enabling to obtain extended shelf-life of the products in comparison to liquid storage.

In order to enable freezing, a stabilizer (cryoprotectant) is added. In one embodiment, the lipoplexes are diluted with the stabilizer (cryoprotectant), after manufacturing, thus enabling to adjust the ionic strength, preferentially to reduce the ionic strength and adjusting the appropriate concentration of the stabilizer. For freezing of the product, the stabilizer concentration may be higher than the value to obtain physiological osmolality. In that case, for administration, the product is diluted with a suitable aqueous phase (e.g. water for injection, saline) in order to adjust the desired osmolality and ionic strength. As stabilizer sugars like glucose, sucrose or trehalose, but also other compounds, like dextrans, can be used.

Surprisingly, it has been found according to the disclosure that an RNA lipoplex formulation comprising a stabilizer as described herein can also be lyophilized. For lyophilization, the required stabilizer (lyoprotectant) concentration can be lower than for freezing, and the tolerated NaCl concentration (ionic strength) can be higher than for freezing. The product can be also spray-dried, if economic dehydration at large scale is required.

The pH of some of the RNA lipoplex formulations is adjusted to a value which is lower than the usual physiological range and the usual pH optimum for RNA storage in the bulk phase. The optimum pH is about 6.2, a suitable range is between about 5.7 and about 6.7. For other formulations the ideal pH may be even lower. It is hypothesized, that the local pH inside the RNA lipoplexes is higher than the bulk phase pH due to the positive charges of the cationic lipid.

In those embodiments of the disclosure wherein the RNA lipoplex compositions are frozen for storage, the compositions may be thawed and optionally the osmolality, ionic strength and/or the pH of the composition may be adjusted by adding an aqueous liquid. The resulting composition may be administered to a subject.

In those embodiments of the disclosure wherein the RNA lipoplex compositions are lyophilized or freeze-dried for storage, the compositions may be reconstituted by adding an aqueous liquid and optionally the osmolality, ionic strength and/or the pH of the composition may be adjusted by adding an aqueous liquid. The resulting composition may be administered to a subject.

Accordingly, in this aspect, the disclosure relates to a method of preparing a frozen composition comprising RNA lipoplex particles comprising (i) providing an aqueous composition comprising RNA lipoplex particles and a stabilizer and (ii) freezing the composition.

In one embodiment, freezing is at a temperature from about −15° C. to about −40° C., or at about −30° C.

In one embodiment, the composition is stored, for example, at a storage temperature of from about −15° C. to about −40° C., or about −20° C.

In one embodiment, the stabilizer is a carbohydrate selected from a monosaccharide, a disaccharide, a trisaccharide, a sugar alcohol, an oligosaccharide or its corresponding sugar alcohol, and a straight chain polyalcohol.

In one embodiment, providing an aqueous composition comprising RNA lipoplex particles and a stabilizer comprises providing an aqueous composition comprising RNA lipoplex particles and adding the stabilizer to the aqueous composition comprising RNA lipoplex particles. Accordingly, a method of preparing a composition for freezing comprises providing an aqueous composition comprising RNA lipoplex particles and adding a stabilizer to the aqueous composition comprising RNA lipoplex particles.

In one embodiment, adding the stabilizer to the aqueous composition comprising RNA lipoplex particles reduces the ionic strength of the aqueous composition comprising RNA lipoplex particles In one embodiment, the concentration of stabilizer in the aqueous composition comprising RNA lipoplex particles and a stabilizer is higher than the value required for physiological osmolality.

In one embodiment, the concentration of stabilizer in the aqueous composition comprising RNA lipoplexes and a stabilizer is sufficient to maintain the quality of the RNA lipoplex particles and, in particular, to avoid substantial loss of RNA activity after storage of the composition at a temperature from about −15° C. to about −40° C. for at least one month, for at least 6 months, for at least 12 months, for at least 24 months, or for at least 36 months.

In one embodiment, the concentration of stabilizer in the aqueous composition comprising RNA lipoplexes and a stabilizer is from about 5% to about 35.0% (w/v), from about 10% to about 30.0% (w/v), from about 12.5% to about 25.0% (w/v), or about 22.0% (w/v).

In one embodiment, the pH in the aqueous composition comprising RNA lipoplexes and a stabilizer is lower than the usual pH optimum for RNA storage.

In one embodiment, the aqueous composition comprising RNA lipoplexes and a stabilizer comprises sodium chloride at a concentration from about 10 mM to about 50 mM, or comprises an ionic strength corresponding to sodium chloride at a concentration from about 10 mM to about 50 mM.

In one embodiment, the aqueous composition comprising RNA lipoplexes and a stabilizer has an ionic strength corresponding to sodium chloride at a concentration of about 20 mM.

In one embodiment, the RNA lipoplex particles are obtainable by the method as described above under I. and II.

In one embodiment, the method of preparing a frozen composition further comprises storing the frozen composition comprising RNA lipoplex particles. The composition may be stored at a temperature which corresponds or essentially corresponds to the freezing temperature, or a temperature which is higher or lower than the freezing temperature. Generally, the composition is stored at a temperature from about −15° C. to about −40° C., e.g. at about −20° C.

The disclosure further relates to a composition comprising RNA lipoplex particles which is obtainable by the above method of preparing a frozen composition. The disclosure also relates to a composition comprising RNA lipoplex particles which is obtainable by the above method of preparing a composition for freezing.

In one embodiment, the RNA lipoplex particles comprise at least one cationic lipid and at least one additional lipid.

In one embodiment, the RNA encodes a peptide or protein comprising at least one epitope, wherein the ratio of positive charges to negative charges in the RNA lipoplex particles is from about 1:2 to about 1.9:2, or about 1.3:2.0.

In one embodiment, the composition further comprises sodium chloride at a concentration from about 10 mM to about 50 mM.

The disclosure further relates to a composition comprising: RNA lipoplex particles comprising:
  RNA encoding a peptide or protein comprising at least one epitope,
  at least one cationic lipid and at least one additional lipid,
    wherein the ratio of positive charges to negative charges in the RNA lipoplex particles is from about 1:2 to about 1.9:2, or about 1.3:2.0,
sodium chloride at a concentration from 0 mM to about 40 mM, and
a stabilizer.

In one embodiment, the composition further comprises a buffer

In one embodiment, the amount of RNA in the composition is from about 0.01 mg/mL to about 1 mg/mL, about 0.05 mg/mL to about 0.5 mg/mL, or about 0.05 mg/mL.

In one embodiment, the sodium chloride is at a concentration from about 20 mM to about 30 mM.

In one embodiment, the sodium chloride is at a concentration of about 20 mM.

In one embodiment, the sodium chloride is at a concentration of about 30 mM.

In one embodiment, the concentration of stabilizer in the composition is higher than the value required for physiological osmolality.

In one embodiment, the concentration of stabilizer in the composition is from about 5 to about 35 weight by volume percent (% w/v), or from about 12.5 to about 25 weight by volume percent (% w/v).

In one embodiment, the stabilizer is a carbohydrate selected from a monosaccharide, a disaccharide, a trisaccharide, a sugar alcohol, an oligosaccharide or its corresponding sugar alcohol, and a straight chain polyalcohol.

In one embodiment, the stabilizer is sucrose at a concentration from about 5 to about 25 weight by volume percent (% w/v).

In one embodiment, the sucrose is at a concentration from about 15% (w/v) to about 25% (w/v).

In one embodiment, the sucrose is at a concentration from about 20% (w/v) to about 25% (w/v).

In one embodiment, the sucrose is at a concentration of about 22% (w/v).

In one embodiment, the sucrose is at a concentration of about 20% (w/v).

In one embodiment, the composition has a pH that is lower than the usual pH optimum for RNA storage.

In one embodiment, the composition has a pH from about 5.7 to about 6.7, or of about 6.2.

In one embodiment, the buffer is 2-[4-(2-hydroxyethyl)piperazin-1-yl]ethanesulfonic acid (HEPES).

In one embodiment, the HEPES is at a concentration from about 2.5 mM to about 10 mM, or of about 7.5 mM.

In one embodiment, the composition further comprises a chelating agent.

The disclosure further relates to a composition comprising: RNA lipoplex particles comprising:
  RNA encoding a peptide or protein comprising at least one epitope at a concentration of about 0.05 mg/mL, and
  DOTMA and DOPE in a molar ratio of about 2:1,
  wherein the ratio of positive charges to negative charges in the RNA lipoplex particles is about 1.3:2.0,
sodium chloride at a concentration of about 20 mM,
sucrose at a concentration of about 22% (w/v),
HEPES at a concentration of about 7.5 mM with a pH of about 6.2, and
EDTA at a concentration of about 2.5 mM.

In one embodiment, the composition is in a liquid or frozen state.

In one embodiment, the frozen composition is stable at a temperature from about −15° C. to about −40° C. for at least one month, for at least 6 months, for at least 12 months, for at least 24 months, or for at least 36 months.

In one embodiment, the frozen composition is stable at a temperature of about −15° C. for at least one month, for at least 6 months, for at least 12 months, for at least 24 months, or for at least 36 months.

In one embodiment, the frozen composition is stable at a temperature of about −15° C. for at least two months.

In one embodiment, the frozen composition is stable at a temperature of about −20° C. for at least one month, for at least 6 months, for at least 12 months, for at least 24 months, or for at least 36 months.

In one embodiment, the frozen composition is stable at a temperature of about −20° C. for at least two months.

In one embodiment, the frozen composition is stable at a temperature of about −30° C. for at least one month, for at least 6 months, for at least 12 months, for at least 24 months, or for at least 36 months.

In one embodiment, the frozen composition is stable at a temperature of about −30° C. for at least two months.

The disclosure further relates to an aqueous composition comprising RNA lipoplex particles obtainable by thawing the above frozen composition and optionally adjusting the osmolality and ionic strength by adding an aqueous liquid.

In one embodiment, the osmolality of the composition is from about 200 mOsmol to about 450 mOsmol.

In one embodiment, the composition comprises sodium chloride at a concentration from about 80 mM to about 150 mM.

In one embodiment, the RNA lipoplex particles are obtainable by the method as described above under I. and II.

The disclosure further relates to a method of preparing a dehydrated, e.g. lyophilized or spray-dried, composition comprising RNA lipoplex particles comprising (i) providing an aqueous composition comprising RNA lipoplex particles and a stabilizer and (ii) dehydrating, e.g. lyophilizing or spray-drying, the composition.

In one embodiment, the stabilizer is a carbohydrate selected from a monosaccharide, a disaccharide, a trisaccharide, a sugar alcohol, an oligosaccharide or its corresponding sugar alcohol, and a straight chain polyalcohol.

In one embodiment, providing an aqueous composition comprising RNA lipoplex particles and a stabilizer comprises providing an aqueous composition comprising RNA lipoplex particles and adding the stabilizer to the aqueous composition comprising RNA lipoplex particles. Accordingly, a method of preparing a composition for dehydration, e.g. lyophilization or spray-drying, comprises providing an aqueous composition comprising RNA lipoplex particles and adding a stabilizer to the aqueous composition comprising RNA lipoplex particles.

In one embodiment, adding the stabilizer to the aqueous composition comprising RNA lipoplex particles reduces the ionic strength of the aqueous composition comprising RNA lipoplex particles In one embodiment, the concentration of stabilizer in the aqueous composition comprising RNA lipoplex particles and a stabilizer is higher than the value required for physiological osmolality.

In one embodiment, the concentration of stabilizer in the aqueous composition comprising RNA lipoplexes and a stabilizer is sufficient to maintain the quality of the RNA lipoplex particles and, in particular, to avoid substantial loss of RNA activity after storage of the composition for at least one month, for at least 6 months, for at least 12 months, for at least 24 months, or for at least 36 months.

In one embodiment, the concentration of stabilizer in the aqueous composition comprising RNA lipoplexes and a stabilizer is from about 5% to about 35.0% (w/v), from about 10% to about 30.0% (w/v), from about 12.5% to about 25.0% (w/v), or about 22.0% (w/v).

In one embodiment, the pH in the aqueous composition comprising RNA lipoplexes and a stabilizer is lower than the usual pH optimum for RNA storage.

In one embodiment, the aqueous composition comprising RNA lipoplexes and a stabilizer comprises sodium chloride at a concentration from about 10 mM to about 80 mM or from about 10 mM to about 50 mM, or comprises an ionic strength corresponding to sodium chloride at a concentration from about 10 mM to about 80 mM or from about 10 mM to about 50 mM.

In one embodiment, the aqueous composition comprising RNA lipoplexes and a stabilizer has an ionic strength corresponding to sodium chloride at a concentration of about 20 mM, about 40 mM, about 60 mM, or about 80 mM.

In one embodiment, the RNA lipoplex particles are obtainable by the method as described above under I. and II.

In one embodiment, the method of preparing a dehydrated, e.g. lyophilized or spray-dried, composition further comprises storing the lyophilized or spray-dried composition comprising RNA lipoplex particles. Generally, the composition is stored at a temperature from about −15° C. to about −40° C., e.g. at about −20° C. In certain embodiments, the composition is stored at a temperature higher than 0° C., for example at about 25° C. or about 4° C., or for example at room temperature.

The disclosure further relates to a composition comprising RNA lipoplex particles which is obtainable by the above method of preparing a dehydrated, e.g. lyophilized or spray-dried, composition. The disclosure also relates to a composition comprising RNA lipoplex particles which is obtainable by the above method of preparing a composition for dehydration, e.g. lyophilization or spray-drying.

In one embodiment, the RNA lipoplex particles comprise at least one cationic lipid and at least one additional lipid.

In one embodiment, the RNA encodes a peptide or protein comprising at least one epitope, wherein the ratio of positive charges to negative charges in the RNA lipoplex particles is from about 1:2 to about 1.9:2, or about 1.3:2.0.

In one embodiment, the composition further comprises sodium chloride at a concentration from about 10 mM to about 80 mM or from about 10 mM to about 50 mM.

The disclosure further relates to a composition comprising:
RNA lipoplex particles comprising:
  RNA encoding a peptide or protein comprising at least one epitope,
  at least one cationic lipid and at least one additional lipid,
  wherein the ratio of positive charges to negative charges in the RNA lipoplex particles is from about 1:2 to about 1.9:2, or about 1.3:2.0,
sodium chloride at a concentration from 10 mM to about 80 mM, and
a stabilizer.

In one embodiment, the composition further comprises a buffer

In one embodiment, the amount of RNA in the composition is from about 0.01 mg/mL to about 1 mg/mL, about 0.05 mg/mL to about 0.5 mg/mL, or about 0.05 mg/mL.

In one embodiment, the sodium chloride is at a concentration from about 20 mM to about 30 mM.

In one embodiment, the sodium chloride is at a concentration of about 20 mM.

In one embodiment, the sodium chloride is at a concentration of about 30 mM.

In one embodiment, the concentration of stabilizer in the composition is higher than the value required for physiological osmolality.

In one embodiment, the concentration of stabilizer in the composition is from about 5 to about 35 weight by volume percent (% w/v), or from about 10 to about 25 weight by volume percent (% w/v).

In one embodiment, the stabilizer is a carbohydrate selected from a monosaccharide, a disaccharide, a trisaccharide, a sugar alcohol, an oligosaccharide or its corresponding sugar alcohol, and a straight chain polyalcohol.

In one embodiment, the stabilizer is trehalose at a concentration from about 5 to about 35 weight by volume percent (% w/v).

In one embodiment, the trehalose is at a concentration from about 5% (w/v) to about 25% (w/v).

In one embodiment, the trehalose is at a concentration from about 10% (w/v) to about 25% (w/v).

In one embodiment, the trehalose is at a concentration of about 10% (w/v).

In one embodiment, the trehalose is at a concentration of about 1.5% (w/v).

In one embodiment, the composition has a pH that is lower than the usual pH optimum for RNA storage.

In one embodiment, the composition has a pH from about 5.7 to about 6.7, or of about 6.2.

In one embodiment, the buffer is 2-[4-(2-hydroxyethyl) piperazin-1-yl]ethanesulfonic acid (HEPES).

In one embodiment, the HEPES is at a concentration from about 2.5 mM to about 10 mM, or of about 7.5 mM.

In one embodiment, the composition further comprises a chelating agent.

The disclosure further relates to a composition comprising:
RNA lipoplex particles comprising:
  RNA encoding a peptide or protein comprising at least one epitope at a concentration of about 0.05 mg/mL, and
  DOTMA and DOPE in a molar ratio of about 2:1,
  wherein the ratio of positive charges to negative charges in the RNA lipoplex particles is about 1.3:2.0,
sodium chloride at a concentration of about 20 mM,
trehalose at a concentration of about 10% (w/v),
HEPES at a concentration of about 7.5 mM with a pH of about 6.2, and
EDTA at a concentration of about 2.5 mM.

In one embodiment, the composition is in a liquid or dehydrated, e.g. lyophilized or freeze-dried, state.

In one embodiment, the dehydrated, e.g. lyophilized or freeze-dried, composition is stable for at least one month, for at least 6 months, for at least 12 months, for at least 24 months, or for at least 36 months. In one embodiment, the composition is stored at a temperature higher than 0° C., for example at about 25° C. or about 4° C., or for example at room temperature.

In one embodiment, the dehydrated, e.g. lyophilized or freeze-dried, composition is stable for at least one month.

In one embodiment, the dehydrated, e.g. lyophilized or freeze-dried, composition is stable for at least two months.

The disclosure further relates to an aqueous composition comprising RNA lipoplex particles obtainable by reconstituting the above dehydrated, e.g. lyophilized or freeze-dried, composition and optionally adjusting the osmolality and ionic strength by adding an aqueous liquid.

In one embodiment, the osmolality of the composition is from about 150 mOsmol to about 450 mOsmol.

In one embodiment, the composition comprises sodium chloride at a concentration from about 80 mM to about 150 mM.

In one embodiment, the RNA lipoplex particles are obtainable by the method as described above under I. and II.

In one embodiment, the RNA lipoplex particles described in this aspect under III. are characterized by a single Bragg peak at about 1 nm$^{-1}$, wherein the peak width is smaller than 0.2 nm$^{-1}$ In one embodiment, the RNA lipoplex particles described in this aspect under III. have an average diameter that ranges from about 200 to about 800 nm, from about 250 to about 700 nm, from about 400 to about 600 nm, from about 300 nm to about 500 nm, or from about 350 nm to about 400 nm.

In one embodiment, the RNA lipoplex particles have a polydispersity index smaller than about 0.5, smaller than about 0.4, or smaller than about 0.3.

In one embodiment, the at least one cationic lipid comprises 1,2-di-O-octadecenyl-3-trimethylammonium propane (DOTMA) and/or 1,2-dioleoyl-3-trimethylammonium-propane (DOTAP).

In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC).

In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE).

In one embodiment, the molar ratio of the at least one cationic lipid to the at least one additional lipid is from about 10:0 to about 1:9, from about 4:1 to about 1:2, from about 3:1 to about 1:1, or about 2:1.

In one embodiment, the RNA lipoplex particles comprise DOTMA and DOPE in a molar ratio of from about 10:0 to 1:9, from about 4:1 to 1:2, from about 3:1 to about 1:1, or about 2:1 and wherein the charge ratio of positive charges in DOTMA to negative charges in the RNA is from about 1:2 to 1.9:2.

In one embodiment, the chelating agent is ethylenediaminetetraacetic acid (EDTA).

In one embodiment, the EDTA is at a concentration from about 0.25 mM to about 5 mM, or of about 2.5 mM.

In one embodiment, the composition further comprises an adjuvant.

In one embodiment, the composition is formulated for systemic administration.

In one embodiment, the systemic administration is by intravenous administration.

The disclosure further relates to a composition as described for therapeutic use.

The disclosure further relates to a method of preparing an aqueous composition comprising RNA lipoplex particles comprising thawing the frozen composition described above or reconstituting the lyophilized or spray-dried composition described above and optionally adjusting the osmolality and ionic strength by adding an aqueous liquid.

In one embodiment, an aqueous liquid is added to obtain an osmolality of the composition from about 200 mOsmol to about 450 mOsmol.

In one embodiment, an aqueous liquid is added to obtain sodium chloride at a concentration from about 80 mM to about 150 mM.

DETAILED DESCRIPTION

Figure 1:
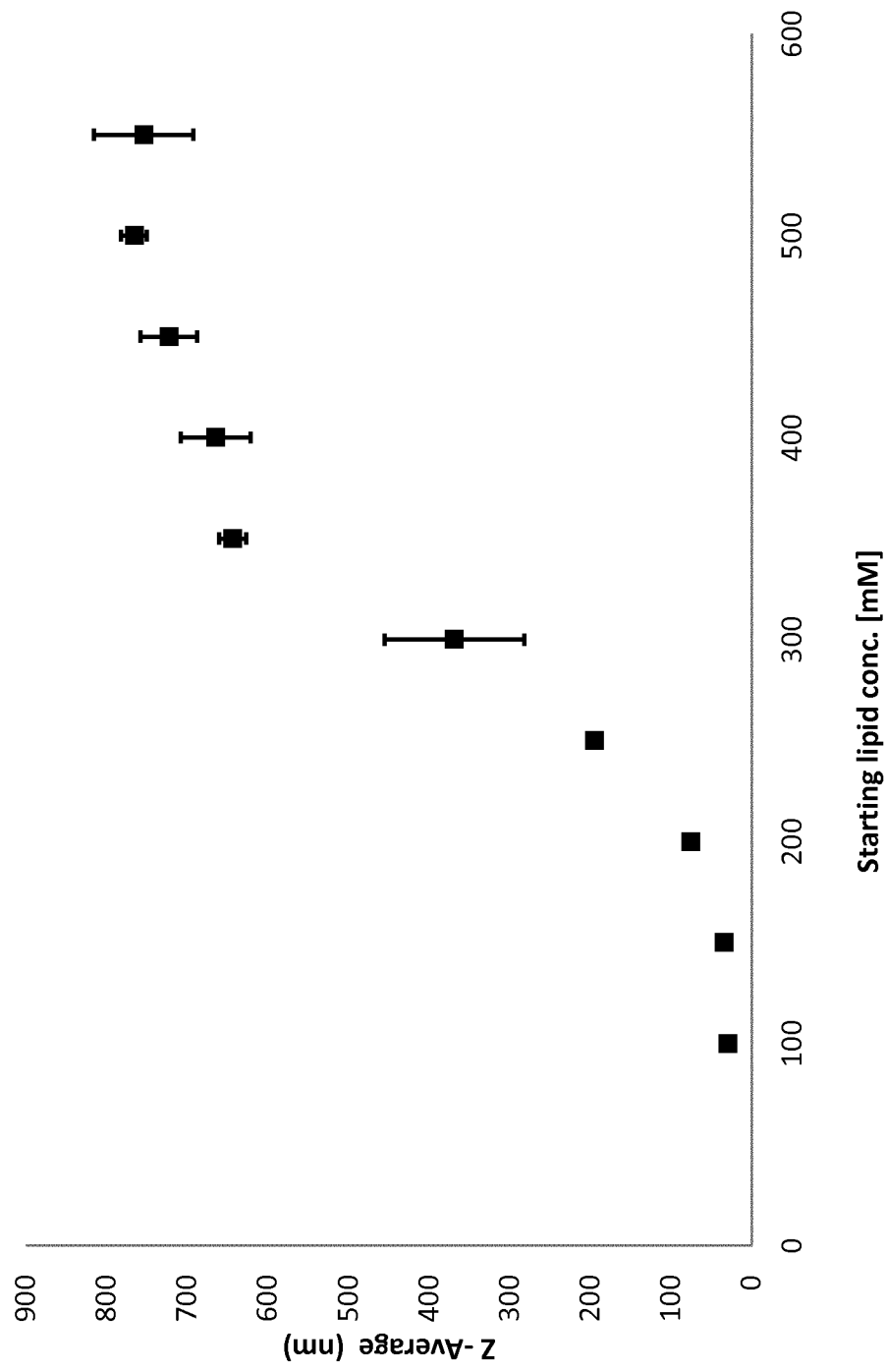
FIG. 1 shows the correlation between lipid concentration in the lipid stock solution and liposome size. Liposomes were prepared by ethanol injection in water (no filtration process performed after ethanol injection). Size of the liposomes increases with the lipid concentration in ethanol. This example: lipid mixture DOTMA/DOPE with a % molar ratio of 66:33.

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e. for the purpose of this embodiment "comprising" is to be understood as having the meaning of "consisting of".

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

Terms such as "reduce" or "inhibit" as used herein means the ability to cause an overall decrease, for example, of about 5% or greater, about 10% or greater, about 20% or greater, about 50% or greater, or about 75% or greater, in the level. The term "inhibit" or similar phrases includes a complete or essentially complete inhibition, i.e. a reduction to zero or essentially to zero.

Terms such as "increase" or "enhance" in one embodiment relate to an increase or enhancement by at least about 10%, at least about 20%, at least about 30%, at least about 40%, at least about 50%, at least about 80%, or at least about 100%.

"Physiological pH" as used herein refers to a pH of about 7.5.

As used in the present disclosure, "% w/v" refers to weight by volume percent, which is a unit of concentration measuring the amount of solute in grams (g) expressed as a percent of the total volume of solution in milliliters (mL).

The term "ionic strength" refers to the mathematical relationship between the number of different kinds of ionic species in a particular solution and their respective charges. Thus, ionic strength I is represented mathematically by the formula $$I = \frac{1}{2} \cdot \sum_i z_i^2 \cdot c_i$$

in which c is the molar concentration of a particular ionic species and z the absolute value of its charge. The sum $\Sigma$ is taken over all the different kinds of ions (i) in solution.

According to the disclosure, the term "ionic strength" in one embodiment relates to the presence of monovalent ions. Regarding the presence of divalent ions, in particular divalent cations, their concentration or effective concentration (presence of free ions) due to the presence of chelating agents is in one embodiment sufficiently low so as to prevent degradation of the RNA. In one embodiment, the concentration or effective concentration of divalent ions is below the catalytic level for hydrolysis of the phosphodiester bonds between RNA nucleotides. In one embodiment, the concentration of free divalent ions is 20 µM or less. In one embodiment, there are no or essentially no free divalent ions.

"Osmolality" refers to the concentration of a particular solute expressed as the number of osmoles of solute per kilogram of solvent.

The Reynolds number is a dimensionless number, which can be calculated using the following formalism:

$$Re = \frac{\rho \cdot v \cdot l}{\eta}$$

wherein ρ is the density of the fluid, v is the velocity of the fluid, l is the characteristic length (here the inner diameter of the mixing element), and η is the viscosity.

The term "freezing" relates to the solidification of a liquid, usually with the removal of heat.

The term "lyophilizing" or "lyophilization" refers to the freeze-drying of a substance by freezing it and then reducing the surrounding pressure to allow the frozen medium in the substance to sublimate directly from the solid phase to the gas phase.

The term "spray-drying" refers to spray-drying a substance by mixing (heated) gas with a fluid that is atomized (sprayed) within a vessel (spray dryer), where the solvent from the formed droplets evaporates, leading to a dry powder.

The term "cryoprotectant" relates to a substance that is added to a formulation in order to protect the active ingredients during the freezing stages.

The term "lyoprotectant" relates to a substance that is added to a formulation in order to protect the active ingredients during the drying stages.

The term "reconstitute" relates to adding a solvent such as water to a dried product to return it to a liquid state such as its original liquid state.

The term "recombinant" in the context of the present disclosure means "made through genetic engineering". In one embodiment, a "recombinant object" in the context of the present disclosure is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring. The term "found in nature" means "present in nature" and includes known objects as well as objects that have not yet been discovered and/or isolated from nature, but that may be discovered and/or isolated in the future from a natural source.

The term "equilibrium solubility" refers to the concentration of the solute at which the rate at which solute dissolves and the rate at which the solute is deposited out of solution are the same.

In one embodiment, the term concerns the respective concentration at room temperature.

As used herein, the term "room temperature" refers to temperatures greater than 4° C., preferably from about 15° C. to about 40° C., from about 15° C. to about 30° C., from about 15° C. to about 24° C., or from about 16° C. to about 21° C. Such temperatures will include 14° C., 15° C., 16° C., 17° C., 18° C., 19° C., 20° C., 21° C. and 22° C.

In the context of the present disclosure, the term "particle" relates to a structured entity formed by molecules or molecule complexes. In one embodiment, the term "particle" relates to a micro- or nano-sized structure, such as a micro- or nano-sized compact structure.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used in the present disclosure, "nanoparticle" refers to a particle comprising RNA and at least one cationic lipid and having an average diameter suitable for intravenous administration.

The term "average diameter" refers to the mean hydrodynamic diameter of particles as measured by dynamic light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The term "polydispersity index" is used herein as a measure of the size distribution of an ensemble of particles, e.g., nanoparticles. The polydispersity index is calculated based on dynamic light scattering measurements by the so-called cumulant analysis.

As used herein, "sub-visible particles" refers to particles having an average diameter less than 100 micrometers (μm). The number of sub-visible particles can be measured using light obscuration to indicate the degree of aggregation of RNA lipoplex particles in the present disclosure. In some embodiments, the number of sub-visible particles having an average diameter greater than or equal to 10 μm is measured. In other embodiments, the number of sub-visible particles having an average diameter greater than or equal to 25 μm is measured.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion. Using the ethanol injection technique, such colloidal liposome dispersion is, in one embodiment, formed as follows: an ethanol solution comprising lipids, such as cationic lipids like DOTMA and additional lipids, is injected into an aqueous solution under stirring. In one embodiment, the RNA lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

RNA Lipoplex Particle Diameter

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm. RNA lipoplex particles described herein, e.g. generated by the processes described herein, exhibit a polydispersity index less than about 0.5, less than about 0.4, or less than about 0.3. By way of example, the RNA lipoplex particles can exhibit a polydispersity index in a range of about 0.1 to about 0.3.

Lipid

In one embodiment, the lipid solutions, liposomes and RNA lipoplex particles described herein include a cationic lipid. As used herein, a "cationic lipid" refers to a lipid having a net positive charge. Cationic lipids bind negatively charged RNA by electrostatic interaction to the lipid matrix. Generally, cationic lipids possess a lipophilic moiety, such as a sterol, an acyl or diacyl chain, and the head group of the lipid typically carries the positive charge. Examples of cationic lipids include, but are not limited to 1,2-di-O-octadecenyl-3-trimethylammonium propane (DOTMA), dimethyldioctadecylammonium (DDRB); 1,2-dioleoyl-3-trimethylammonium propane (DOTAP); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 2,3-di(tetradecoxy)propyl-(2-hydroxyethyl)-dimethylazanium (DMRIE), 1,2-dimyristoyl-sn-glycero-3-ethylphosphocholine (DMEPC), 1,2-dimyristoyl-3-trimethylammonium propane (DMTAP), 1,2-dioleyloxypropyl-3-dimethyl-hydroxyethyl ammonium bromide (DORIE), and 2,3-dioleoyloxy-[2(spermine carboxamide)ethyl]-N,N-dimethyl-1-propanamium trifluoroacetate (DOSPA). Preferred are DOTMA, DOTAP, DODAC, and DOSPA. In specific embodiments, the at least one cationic lipid is DOTMA and/or DOTAP.

An additional lipid may be incorporated to adjust the overall positive to negative charge ratio and physical stability of the RNA lipoplex particles. In certain embodiments, the additional lipid is a neutral lipid. As used herein, a "neutral lipid" refers to a lipid having a net charge of zero. Examples of neutral lipids include, but are not limited to, 1,2-di-(9Z-octadecenoyl)-sn-glycero-3-phosphoethanolamine (DOPE), 1,2-dioleoyl-sn-glycero-3-phosphocholine (DOPC), diacylphosphatidyl choline, diacylphosphatidyl ethanol amine, ceramide, sphingoemyelin, cephalin, cholesterol, and cerebroside. In specific embodiments, the second lipid is DOPE, cholesterol and/or DOPC.

In certain embodiments, the RNA lipoplex particles include both a cationic lipid and an additional lipid. In an exemplary embodiment, the cationic lipid is DOTMA and the additional lipid is DOPE. Without wishing to be bound by theory, the amount of the at least one cationic lipid compared to the amount of the at least one additional lipid may affect important RNA lipoplex particle characteristics, such as charge, particle size, stability, tissue selectivity, and bioactivity of the RNA. Accordingly, in some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a β-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In certain embodiments of the present disclosure, the RNA in the RNA lipoplex compositions described herein is at a concentration from about 0.01 mg/mL to about 1 mg/mL, or from about 0.05 mg/mL to about 0.5 mg/mL. In specific embodiments, the RNA is at a concentration of about 0.05 mg/mL, about 0.06 mg/mL, about 0.07 mg/mL, about 0.08 mg/mL, about 0.09 mg/mL, about 0.10 mg/mL, about 0.11 mg/mL, about 0.12 mg/mL, about 0.13 mg/mL, about 0.14 mg/mL, about 0.15 mg/mL, about 0.16 mg/mL, about 0.17 mg/mL, about 0.18 mg/mL, about 0.19 mg/mL, about 0.20 mg/mL, about 0.21 mg/mL, about 0.22 mg/mL, about 0.23 mg/mL, about 0.24 mg/mL, about 0.25 mg/mL, about 0.26 mg/mL, about 0.27 mg/mL, about 0.28 mg/mL, about 0.29 mg/mL, about 0.30 mg/mL, about 0.31 mg/mL, about 0.32 mg/mL, about 0.33 mg/mL, about 0.34 mg/mL, about 0.35 mg/mL, about 0.36 mg/mL, about 0.37 mg/mL, about 0.38 mg/mL, about 0.39 mg/mL, about 0.40 mg/mL, about 0.41 mg/mL, about 0.42 mg/mL, about 0.43 mg/mL, about 0.44 mg/mL, about 0.45 mg/mL, about 0.46 mg/mL, about 0.47 mg/mL, about 0.48 mg/mL, about 0.49 mg/mL, or about 0.50 mg/mL. In an exemplary embodiment, the RNA is at a concentration of 0.05 mg/mL.

In one embodiment, the RNA may have modified ribonucleotides. Examples of modified ribonucleotides include, without limitation, 5-methylcytidine and pseudouridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5' to 5' triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) tail. Thus, the 3'-UTR is upstream of the poly(A) sequence (if present), e.g. directly adjacent to the poly(A) sequence.

In some embodiments, the RNA according to the present disclosure comprises a 3'-poly(A) sequence. The term "poly (A) sequence" relates to a sequence of adenyl (A) residues which typically is located at the 3'-end of a RNA molecule. According to the disclosure, in one embodiment, a poly(A) sequence comprises at least about 20, at least about 40, at least about 80, or at least about 100, and up to about 500, up to about 400, up to about 300, up to about 200, or up to about 150 A nucleotides, and in particular about 120 A nucleotides.

In the context of the present disclosure, the term "transcription" relates to a process, wherein the genetic code in a DNA sequence is transcribed into RNA. Subsequently, the RNA may be translated into peptide or protein.

With respect to RNA, the term "expression" or "translation" relates to the process in the ribosomes of a cell by which a strand of mRNA directs the assembly of a sequence of amino acids to make a peptide or protein.

In one embodiment, after administration of the RNA lipoplex particles described herein, at least a portion of the RNA is delivered to a target cell. In one embodiment, at least a portion of the RNA is delivered to the cytosol of the target cell. In one embodiment, the RNA is RNA encoding a peptide or protein and the RNA is translated by the target cell to produce the peptide or protein.

In one embodiment, the target cell is a spleen cell. In one embodiment, the target cell is an antigen presenting cell such as a professional antigen presenting cell in the spleen. In one embodiment, the target cell is a dendritic cell in the spleen. Thus, RNA lipoplex particles described herein may be used for delivering RNA to such target cell. Accordingly, the present disclosure also relates to a method for delivering RNA to a target cell in a subject comprising the administration of the RNA lipoplex particles described herein to the subject. In one embodiment, the RNA is delivered to the cytosol of the target cell. In one embodiment, the RNA is RNA encoding a peptide or protein and the RNA is translated by the target cell to produce the peptide or protein.

In an embodiment, RNA encodes a pharmaceutically active peptide or protein.

According to the disclosure, the term "RNA encodes" means that the RNA, if present in the appropriate environment, such as within cells of a target tissue, can direct the assembly of amino acids to produce the peptide or protein it encodes during the process of translation. In one embodiment, RNA is able to interact with the cellular translation machinery allowing translation of the peptide or protein. A cell may produce the encoded peptide or protein intracellularly (e.g. in the cytoplasm and/or in the nucleus), may secrete the encoded peptide or protein, or may produce it on the surface.

According to the disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" refers to large peptides, in particular peptides having at least about 151 amino acids, but the terms "peptide" and "protein" are used herein usually as synonyms.

A "pharmaceutically active peptide or protein" has a positive or advantageous effect on a condition or disease state of a subject when provided to the subject in a therapeutically effective amount. In one embodiment, a pharmaceutically active peptide or protein has curative or palliative properties and may be administered to ameliorate, relieve, alleviate, reverse, delay onset of or lessen the severity of one or more symptoms of a disease or disorder. A pharmaceutically active peptide or protein may have prophylactic properties and may be used to delay the onset of a disease or to lessen the severity of such disease or pathological condition. The term "pharmaceutically active peptide or protein" includes entire proteins or polypeptides, and can also refer to pharmaceutically active fragments thereof. It can also include pharmaceutically active analogs of a peptide or protein.

Examples of pharmaceutically active proteins include, but are not limited to, cytokines and immune system proteins such as immunologically active compounds (e.g., interleukins, colony stimulating factor (CSF), granulocyte colony stimulating factor (G-CSF), granulocyte-macrophage colony stimulating factor (GM-CSF), erythropoietin, tumor necrosis factor (TNF), interferons, integrins, addressins, seletins, homing receptors, T cell receptors, immunoglobulins, soluble major histocompatibility complex antigens, immunologically active antigens such as bacterial, parasitic, or viral antigens, allergens, autoantigens, antibodies), hormones (insulin, thyroid hormone, catecholamines, gonadotrophines, trophic hormones, prolactin, oxytocin, dopamine, bovine somatotropin, leptins and the like), growth hormones (e.g., human grown hormone), growth factors (e.g., epidermal growth factor, nerve growth factor, insulin-like growth factor and the like), growth factor receptors, enzymes (tissue plasminogen activator, streptokinase, cholesterol biosynthestic or degradative, steriodogenic enzymes, kinases, phosphodiesterases, methylases, de-methylases, dehydrogenases, cellulases, proteases, lipases, phospholipases, aromatases, cytochromes, adenylate or guanylaste cyclases, neuramidases and the like), receptors (steroid hormone receptors, peptide receptors), binding proteins (growth hormone or growth factor binding proteins and the like), transcription and translation factors, tumor growth suppressing proteins (e.g., proteins which inhibit angiogenesis), structural proteins (such as collagen, fibroin, fibrinogen, elastin, tubulin, actin, and myosin), blood proteins (thrombin, serum albumin, Factor VII, Factor VIII, insulin, Factor IX, Factor X, tissue plasminogen activator, protein C, von Wilebrand factor, antithrombin III, glucocerebrosidase, erythropoietin granulocyte colony stimulating factor (GCSF) or modified Factor VIII, anticoagulants and the like.

The term "immunologically active compound" relates to any compound altering an immune response, for example, by inducing and/or suppressing maturation of immune cells, inducing and/or suppressing cytokine biosynthesis, and/or altering humoral immunity by stimulating antibody production by B cells. Immunologically active compounds possess potent immunostimulating activity including, but not limited to, antiviral and antitumor activity, and can also downregulate other aspects of the immune response, for example shifting the immune response away from a TH2 immune response, which is useful for treating a wide range of TH2 mediated diseases. Immunologically active compounds can be useful as vaccine adjuvants.

In one embodiment, a pharmaceutically active peptide or protein comprises one or more antigens or one or more epitopes, i.e., administration of the peptide or protein to a subject elicits an immune response against the one or more antigens or one or more epitopes in a subject which may be therapeutic or partially or fully protective.

The term "antigen" relates to an agent comprising an epitope against which an immune response can be generated. The term "antigen" includes, in particular, proteins and peptides. In one embodiment, an antigen is presented by cells of the immune system such as antigen presenting cells like dendritic cells or macrophages. An antigen or a processing product thereof such as a T cell epitope is in one embodiment bound by a T or B cell receptor, or by an immunoglobulin molecule such as an antibody. Accordingly, an antigen or a processing product thereof may react specifically with antibodies or T-lymphocytes (T-cells). In one embodiment, an antigen is a disease-associated antigen, such as a tumor antigen, a viral antigen, or a bacterial antigen and an epitope is derived from such antigen.

The term "disease-associated antigen" is used in its broadest sense to refer to any antigen associated with a disease. A disease-associated antigen is a molecule which contains epitopes that will stimulate a host's immune system to make a cellular antigen-specific immune response and/or a humoral antibody response against the disease. The disease-associated antigen or an epitope thereof may therefore be used for therapeutic purposes. Disease-associated antigens may be associated with infection by microbes, typically microbial antigens, or associated with cancer, typically tumors.

The term "tumor antigen" refers to a constituent of cancer cells which may be derived from the cytoplasm, the cell surface and the cell nucleus. In particular, it refers to those antigens which are produced intracellularly or as surface antigens on tumor cells.

The term "viral antigen" refers to any viral component having antigenic properties, i.e. being able to provoke an immune response in an individual. The viral antigen may be a viral ribonucleoprotein or an envelope protein.

The term "bacterial antigen" refers to any bacterial component having antigenic properties, i.e. being able to provoke an immune response in an individual. The bacterial antigen may be derived from the cell wall or cytoplasm membrane of the bacterium.

The term "epitope" refers to a part or fragment a molecule such as an antigen that is recognized by the immune system. For example, the epitope may be recognized by T cells, B cells or antibodies. An epitope of an antigen may include a continuous or discontinuous portion of the antigen and may be between about 5 and about 100 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

In certain embodiments of the present disclosure, the RNA encodes at least one epitope. In certain embodiments, the epitope is derived from a tumor antigen. The tumor antigen may be a "standard" antigen, which is generally known to be expressed in various cancers. The tumor antigen may also be a "neo-antigen", which is specific to an individual's tumor and has not been previously recognized by the immune system. A neo-antigen or neo-epitope may result from one or more cancer-specific mutations in the genome of cancer cells resulting in amino acid changes. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUD FN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5. MAGE-A6, MAGE-A7, MAGE-A8, MAGE-A9, MAGE-A 10, MAGE-A 11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pm1/RARa, PRAME, proteinase 3, PSA, PSM, RAGE, RUI or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

Cancer mutations vary with each individual. Thus, cancer mutations that encode novel epitopes (neo-epitopes) represent attractive targets in the development of vaccine compositions and immunotherapies. The efficacy of tumor immunotherapy relies on the selection of cancer-specific antigens and epitopes capable of inducing a potent immune response within a host. RNA can be used to deliver patient-specific tumor epitopes to a patient. Dendritic cells (DCs) residing in the spleen represent antigen-presenting cells of particular interest for RNA expression of immunogenic epitopes or antigens such as tumor epitopes. The use of multiple epitopes has been shown to promote therapeutic efficacy in tumor vaccine compositions. Rapid sequencing of the tumor mutanome may provide multiple epitopes for individualized vaccines which can be encoded by RNA described herein, e.g., as a single polypeptide wherein the epitopes are optionally separated by linkers. In certain embodiments of the present disclosure, the RNA encodes at least one epitope, at least two epitopes, at least three epitopes, at least four epitopes, at least five epitopes, at least six epitopes, at least seven epitopes, at least eight epitopes, at least nine epitopes, or at least ten epitopes. Exemplary embodiments include RNA that encodes at least five epitopes (termed a "pentatope") and RNA that encodes at least ten epitopes (termed a "decatope").

Charge Ratio

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)]. The concentration of RNA and the at least one cationic lipid amount can be determined using routine methods by one skilled in the art.

In a first embodiment, at physiological pH the charge ratio of positive charges to negative charges in the RNA lipoplex particles is from about 1.9:2 to about 1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0. In one embodiment, the charge ratio of positive charges to negative charges in the RNA lipoplex particles at physiological pH is 1.3:2.0. In another embodiment, the RNA lipoplex particles described herein may have an equal number of positive and negative charges at physiological pH, yielding RNA lipoplex particles with a net neutral charge ratio.

In a second embodiment, at physiological pH the charge ratio of positive charges to negative charges in the RNA lipoplex particles is from about 6:1 to about 1.5:1. In specific embodiments, the charge ratio of positive charges to negative charges in the RNA lipoplex particles at physiological pH is about 6.0:1.0, about 5.9:1.0, about 5.8:1.0, about 5.7:1.0, about 5.6:1.0, about 5.5:1.0, about 5.4:1.0, about 5.3:1.0, about 5.2:1.0, about 5.1:1.0, about 5.0:1.0, about 4.9:1.0, about 4.8:1.0, about 4.7:1.0, about 4.6:1.0, about 4.5:1.0, about 4.4:1.0, about 4.3:1.0, about 4.2:1.0, about 4.1:1.0, about 4.0:1.0, about 3.9:1.0, about 3.8:1.0, about 3.7:1.0, about 3.6:1.0, about 3.5:1.0, about 3.4:1.0, about 3.3:1.0, about 3.2:1.0, about 3.1:1.0, about 3.0:1.0, about 2.9:1.0, about 2.8:1.0, about 2.7:1.0, about 2.6:1.0, about 2.5:1.0, about 2.4:1.0, about 2.3:1.0, about 2.2:1.0, about 2.1:1.0, about 2.0:1.0, about 1.9:1.0, about 1.8:1.0, about 1.7:1.0, about 1.6:1.0, or about 1.5:1.0.

For RNA based immunotherapy, targeting precise organs, such as the spleen, is necessary to avoid an autoimmune response in other organs and potential toxicity. According to the disclosure, RNA may be targeted to different cells, tissues or organs.

It has been found that RNA lipoplex particles having a charge ratio according to the first embodiment may be used to preferentially target spleen tissue or spleen cells such as antigen-presenting cells, in particular dendritic cells. Accordingly, in one embodiment, following administration of the RNA lipoplex particles, RNA accumulation and/or RNA expression in the spleen occurs. Thus, RNA lipoplex particles of the disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the disclosure may be used for expressing RNA in such antigen presenting cells. In one embodiment, the antigen presenting cells are dendritic cells and/or macrophages.

It has been found that RNA lipoplex particles having a charge ratio according to the second embodiment may be used to preferentially target lung tissue or lung cells. Accordingly, in one embodiment, following administration of the RNA lipoplex particles, RNA accumulation and/or RNA expression in the lung occurs. Thus, RNA lipoplex particles of the disclosure may be used for expressing RNA in the lung. Accordingly, if expression of RNA in tissue other than spleen is desired, in embodiments described herein in connection with a charge ratio according to the first embodiment, e.g., a charge ratio from about 1:2 to about 1.9:2, a charge ratio according to the second embodiment, e.g., a charge ratio from about 6:1 to about 1.5:1, may be used instead of the charge ratio according to the first embodiment. In these and other embodiments described herein RNA other than RNA encoding a peptide or protein comprising at least one epitope, e.g. RNA encoding a pharmaceutically active peptide or protein as described herein may be used. In one embodiment, the pharmaceutically active peptide or protein is a cytokine and/or the treatment of lung cancer is intended.

Compositions Comprising RNA Lipoplex Particles

A. Salt and Ionic Strength

According to the present disclosure, the compositions described herein may comprise salts such as sodium chloride. Without wishing to be bound by theory, sodium chloride functions as an ionic osmolality agent for preconditioning RNA prior to mixing with the at least one cationic lipid. Certain embodiments contemplate alternative organic or inorganic salts to sodium chloride in the present disclosure. Alternative salts include, without limitation, potassium chloride, dipotassium phosphate, monopotassium phosphate, potassium acetate, potassium bicarbonate, potassium sulfate, potassium acetate, disodium phosphate, monosodium phosphate, sodium acetate, sodium bicarbonate, sodium sulfate, sodium acetate, lithium chloride, magnesium chloride, magnesium phosphate, calcium chloride, and sodium salts of ethylenediaminetetraacetic acid (EDTA).

Generally, compositions comprising RNA lipoplex particles described herein comprise sodium chloride at a concentration that preferably ranges from 0 mM to about 500 mM, from about 5 mM to about 400 mM, or from about 10 mM to about 300 mM. In one embodiment, compositions comprising RNA lipoplex particles comprise an ionic strength corresponding to such sodium chloride concentrations.

Generally, compositions for and resulting from forming RNA lipoplex particles from RNA and liposomes such as those described herein comprise high sodium chloride concentrations, or comprises a high ionic strength. In one embodiment, the sodium chloride is at a concentration of at least 45 mM. In one embodiment, the sodium chloride is at a concentration of about 45 mM to about 300 mM, or from about 50 mM to about 150 mM. In one embodiment, the compositions comprise an ionic strength corresponding to such sodium chloride concentrations.

Generally, compositions for storing RNA lipoplex particles such as for freezing of RNA lipoplex particles such as those described herein comprise low sodium chloride concentrations, or comprises a low ionic strength. In one embodiment, the sodium chloride is at a concentration from 0 mM to about 50 mM, from 0 mM to about 40 mM, or from about 10 mM to about 50 mM. In specific embodiments, the sodium chloride is at a concentration of about 1 mM, about 2 mM, about 3 mM, about 4 mM, about 5 mM, about 6 mM, about 7 mM, about 8 mM, about 9 mM, about 10 mM, about 11 mM, about 12 mM, about 13 mM, about 14 mM, about 15 mM, about 16 mM, about 17 mM, about 18 mM, about 19 mM, about 20 mM, about 21 mM, about 22 mM, about 23 mM, about 24 mM, about 25 mM, about 26 mM, about 27 mM, about 28 mM, about 29 mM, about 30 mM, about 31 mM, about 32 mM, about 33 mM, about 34 mM, about 35 mM, about 36 mM, about 37 mM, about 38 mM, about 39 mM, about 40 mM, about 41 mM, about 42 mM, about 43 mM, about 44 mM, about 45 mM, about 46 mM, about 47 mM, about 48 mM, about 49 mM, or about 50 mM. In preferred embodiments, the sodium chloride is at a concentration of about 20 mM, about 30 mM, or about 40 mM. In one exemplary embodiment, the sodium chloride is at a concentration of 20 mM. In another exemplary embodiment, the sodium chloride is at a concentration of 30 mM. In one embodiment, the compositions comprise an ionic strength corresponding to such sodium chloride concentrations.

Generally, compositions resulting from thawing frozen RNA lipoplex particle compositions and optionally adjusting the osmolality and ionic strength by adding an aqueous liquid comprise high sodium chloride concentrations, or comprises a high ionic strength. In one embodiment, the sodium chloride is at a concentration of about 50 mM to about 300 mM, or from about 80 mM to about 150 mM. In one embodiment, the compositions comprise an ionic strength corresponding to such sodium chloride concentrations.

B. Stabilizer

Compositions described herein may comprise a stabilizer to avoid substantial loss of the product quality and, in particular, substantial loss of RNA activity during freezing, lyophilization or spray-drying and storage of the frozen, lyophilized or spray-dried composition. Such a composition is also referred to as stable herein. Typically the stabilizer is present prior to the freezing, lyophilization or spray-drying process and persists in the resulting frozen, lyophilized or freeze-dried preparation. It can be used to protect RNA lipoplex particles during freezing, lyophilization or spray-drying and storage of the frozen, lyophilized or freeze-dried preparation, for example to reduce or prevent aggregation, particle collapse, RNA degradation and/or other types of damage.

In an embodiment the stabilizer is a carbohydrate. The term "carbohydrate", as used herein refers to and encompasses monosaccharides, disaccharides, trisaccharides, oligosaccharides and polysaccharides.

In an embodiment, the stabilizer is a monosaccharide. The term "monosaccharide", as used herein refers to a single carbohydrate unit (e.g., a simple sugar) that cannot be hydrolyzed to simpler carbohydrate units. Exemplary monosaccharide stabilizers include glucose, fructose, galactose, xylose, ribose and the like.

In an embodiment, the stabilizer is a disaccharide. The term "disaccharide", as used herein refers to a compound or a chemical moiety formed by 2 monosaccharide units that are bonded together through a glycosidic linkage, for example through 1-4 linkages or 1-6 linkages. A disaccharide may be hydrolyzed into two monosaccharides. Exemplary disaccharide stabilizers include sucrose, trehalose, lactose, maltose and the like.

The term "trisaccharide" means three sugars linked together to form one molecule. Examples of a trisaccharides include raffinose and melezitose.

In an embodiment, the stabilizer is an oligosaccharide. The term "oligosaccharide", as used herein refers to a compound or a chemical moiety formed by 3 to about 15, preferably 3 to about 10 monosaccharide units that are bonded together through glycosidic linkages, for example through 1-4 linkages or 1-6 linkages, to form a linear, branched or cyclic structure. Exemplary oligosaccharide stabilizers include cyclodextrins, raffinose, melezitose, maltotriose, stachyose, acarbose, and the like. An oligosaccharide can be oxidized or reduced.

In an embodiment, the stabilizer is a cyclic oligosaccharide. The term "cyclic oligosaccharide", as used herein refers to a compound or a chemical moiety formed by 3 to about 15, preferably 6, 7, 8, 9, or 10 monosaccharide units that are bonded together through glycosidic linkages, for example through 1-4 linkages or 1-6 linkages, to form a cyclic structure. Exemplary cyclic oligosaccharide stabilizers include cyclic oligosaccharides that are discrete compounds, such as a cyclodextrin, β cyclodextrin, or γ cyclodextrin.

Other exemplary cyclic oligosaccharide stabilizers include compounds which include a cyclodextrin moiety in a larger molecular structure, such as a polymer that contains a cyclic oligosaccharide moiety. A cyclic oligosaccharide can be oxidized or reduced, for example, oxidized to dicarbonyl forms. The term "cyclodextrin moiety", as used herein refers to cyclodextrin (e.g., an α, β, or γ cyclodextrin) radical that is incorporated into, or a part of, a larger molecular structure, such as a polymer. A cyclodextrin moiety can be bonded to one or more other moieties directly, or through an optional linker. A cyclodextrin moiety can be oxidized or reduced, for example, oxidized to dicarbonyl forms.

Carbohydrate stabilizers, e.g., cyclic oligosaccharide stabilizers, can be derivatized carbohydrates. For example, in an embodiment, the stabilizer is a derivatized cyclic oligosaccharide, e.g., a derivatized cyclodextrin, e.g., 2-hydroxypropyl-β-cyclodextrin, e.g., partially etherified cyclodextrins (e.g., partially etherified β cyclodextrins).

An exemplary stabilizer is a polysaccharide. The term "polysaccharide", as used herein refers to a compound or a chemical moiety formed by at least 16 monosaccharide units that are bonded together through glycosidic linkages, for example through 1-4 linkages or 1-6 linkages, to form a linear, branched or cyclic structure, and includes polymers that comprise polysaccharides as part of their backbone structure. In backbones, the polysaccharide can be linear or cyclic. Exemplary polysaccharide stabilizers include glycogen, amylase, cellulose, dextran, maltodextrin and the like.

In an embodiment, the stabilizer is a sugar alcohol. As used herein, the term "sugar alcohol" refers to reduction products of "sugars" and indicates that all oxygen atoms in a simple sugar alcohol molecule are present in the form of hydroxyl groups. The sugar alcohols are "polyols". This term refers to chemical compounds containing three or more hydroxyl groups, and is synonymous with another customary term, polyhydric alcohol. Examples of sugar alcohols include, but are not limited to, sorbitol, mannitol, maltitol, lactitol, erythritol, glycerin, xylitol, or inositol.

According to the present disclosure, pharmaceutical compositions that include sucrose as a stabilizer are provided. Without wishing to be bound by theory, sucrose functions to promote cryoprotection of the composition, thereby preventing RNA lipoplex particle aggregation and maintaining chemical and physical stability of the composition. Certain embodiments contemplate alternative stabilizers to sucrose in the present disclosure. Alternative stabilizers include, without limitation, trehalose, glucose, fructose, arginin, glycerin, mannitol, prolin, sorbitol, glycine betaine and dextran. In a specific embodiment, an alternative stabilizer to sucrose is trehalose.

In one embodiment, the stabilizer is at a concentration from about 5% (w/v) to about 35% (w/v), or from about 10% (w/v) to about 25% (w/v). In specific embodiments, the stabilizer is at a concentration of about 10% (w/v), about 11% (w/v), about 12% (w/v), about 13% (w/v), about 14% (w/v), about 15% (w/v), about 16% (w/v), about 17% (w/v), about 18% (w/v), about 19% (w/v), about 20% (w/v), about 21% (w/v), about 22% (w/v), about 23% (w/v), about 24% (w/v), or about 25% (w/v). In one preferred embodiment, the stabilizer is at a concentration from about 15% (w/v) to about 25% (w/v). In another preferred embodiment, the stabilizer is at a concentration from about 20% (w/v) to about 25% (w/v). In one exemplary embodiment, the stabilizer is at a concentration of about 25% (w/v). In another exemplary embodiment, the stabilizer is at a concentration of about 22% (w/v). In embodiments of the disclosure, the stabilizer is sucrose or trehalose. In an embodiment of the disclosure, the stabilizer is sucrose. In an embodiment of the disclosure, the stabilizer is trehalose.

According to the present disclosure, the RNA lipoplex particle compositions described herein have a stabilizer concentration suitable for the stability of the composition, in particular for the stability of the RNA lipoplex particles and for the stability of the RNA.

C. pH and Buffer

According to the present disclosure, the RNA lipoplex particle compositions described herein have a pH suitable for the stability of the RNA lipoplex particles and, in particular, for the stability of the RNA. In one embodiment, the RNA lipoplex particle compositions described herein have a pH from about 5.7 to about 6.7. In specific embodiments, the compositions have a pH of about 5.7, about 5.8, about 5.9, about 6.0, about 6.1, about 6.2, about 6.3, about 6.4, about 6.5, about 6.6, or about 6.7.

According to the present disclosure, compositions that include buffer are provided. Without wishing to be bound by theory, the use of buffer maintains the pH of the composition during manufacturing, storage and use of the composition. In certain embodiments of the present disclosure, the buffer may be sodium bicarbonate, monosodium phosphate, disodium phosphate, monopotassium phosphate, dipotassium phosphate, [tris(hydroxymethyl)methylamino]propanesulfonic acid (TAPS), 2-(Bis(2-hydroxyethyl)amino)acetic acid (Bicine), 2-Amino-2-(hydroxymethyl)propane-1,3-diol (Tris), N-(2-Hydroxy-1,1-bis(hydroxymethyl)ethyl)glycine (Tricine), [[1,3-dihydroxy-2-(hydroxymethyl)propan-2-yl] amino]-2-hydroxypropane-1-sulfonic acid (TAPSO), 2-[[4-(2-hydroxyethyl)piperazin-1-yl]ethanesulfonic acid (HEPES), 2-[1,3-dihydroxy-2-(hydroxymethyl)propan-2-yl]amino]ethanesulfonic acid (TES), 1,4-piperazinediethanesulfonic acid (PIPES), dimethylarsinic acid, 2-morpholin-4-ylethanesulfonic acid (MES), 3-morpholino-2-hydroxypropanesulfonic acid (MOPSO), or phosphate buffered saline (PBS). Other suitable buffers may be acetic acid in a salt, citric acid in a salt, boric acid in a salt and phosphoric acid in a salt.

In some embodiments, the buffer has a pH from about 5.7 to about 6.7. In specific embodiments, the buffer has a pH of about 5.7, about 5.8, about 5.9, about 6.0, about 6.1, about 6.2, about 6.3, about 6.4, about 6.5, about 6.6, or about 6.7. In one embodiment, the buffer is HEPES. In a preferred embodiment, the HEPES has a pH from about 5.7 to about 6.7. In specific embodiments, the HEPES has a pH of about 5.7, about 5.8, about 5.9, about 6.0, about 6.1, about 6.2, about 6.3, about 6.4, about 6.5, about 6.6, or about 6.7. In an exemplary embodiment, the HEPES has a pH of about 6.2.

In still another embodiment, the buffer has a concentration from about 2.5 mM to about 10 mM. In specific embodiments where HEPES is the buffer, the concentration of HEPES is about 2.5 mM, about 2.75 mM, 3.0 mM, about 3.25 mM, about 3.5 mM, about 3.75 mM, about 4.0 mM, about 4.25 mM, about 4.5 mM, about 4.75 mM, about 5.0 mM, about 5.25 mM, about 5.5 mM, about 5.75 mM, about 6.0 mM, about 6.25 mM, about 6.5 mM, about 6.75 mM, about 7.0 mM, about 7.25 mM, about 7.5 mM, about 7.75 mM, about 8.0 mM, about 8.25 mM, about 8.5 mM, about 8.75 mM, about 9.0 mM, about 9.25 mM, about 9.5 mM, about 9.75 mM, or about 10.0 mM. In a preferred embodiment, the HEPES is at a concentration of about 7.5 mM.

D. Chelating Agent

Certain embodiments of the present disclosure contemplate the use of a chelating agent. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation in the present disclosure. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethyl enetriaminepentaacetic acid (DTPA), bis(aminoethyl)glycolether-N,N,N', N'-tetraacetic acid, iminodiacetic acid, citric acid, tartaric acid, fumaric acid, or a salt thereof. In certain embodiments, the chelating agent is EDTA or a salt of EDTA. In an exemplary embodiment, the chelating agent is EDTA di sodium dihydrate.

In some embodiments, the EDTA is at a concentration from about 0.25 mM to about 5 mM. In specific embodiments, the EDTA is at a concentration of about 0.25 mM, about 0.3 mM, about 0.4 mM, about 0.5 mM, about 0.6 mM, about 0.7 mM, about 0.8 mM, about 0.9 mM, about 1.0 mM, about 1.1 mM, about 1.2 mM, about 1.3 mM, about 1.4 mM, about 1.5 mM, about 1.6 mM, about 1.7 mM, about 1.8 mM, about 1.9 mM, about 2.0 mM, about 2.1 mM, about 2.2 mM, about 2.3 mM, about 2.4 mM, about 2.5 mM, about 2.6 mM, about 2.7 mM, about 2.8 mM, about 2.9 mM, about 3.0 mM, about 3.1 mM, about 3.2 mM, about 3.3 mM, about 3.4 mM, about 3.5 mM, about 3.6 mM, about 3.7 mM, about 3.8 mM, about 3.9 mM, about 4.0 mM, about 4.1 mM, about 4.2 mM, about 4.3 mM, about 4.4 mM, about 4.5 mM, about 4.6 mM, about 4.7 mM, about 4.8 mM, about 4.9 mM, or about 5.0 mM. In a preferred embodiment, the EDTA is at a concentration of about 2.5 mM.

E. Exemplary Compositions of the Disclosure

In one exemplary embodiment, the composition of RNA lipoplex particles includes DOTMA and DOPE in a molar ratio from about 2:1 to about 1:1 and RNA at a concentration of about 0.05 mg/mL that encodes at least one epitope, where at physiological pH the charge ratio of positive charges to negative charges in the RNA lipoplex particles is about 1.3:2.0; sodium chloride at a concentration of about 20 mM; sucrose at a concentration of about 22% (w/v); HEPES at a concentration of about 7.5 mM with a pH of about 6.2; and EDTA at a concentration of about 2.5 mM. In further specific embodiments, the RNA encodes five epitopes or ten epitopes.

In another exemplary embodiment, the composition of RNA lipoplex particles includes DOTMA and DOPE in a molar ratio from about 2:1 to about 1:1 and RNA at a concentration of about 0.05 mg/mL that encodes at least one epitope, where at physiological pH the charge ratio of positive charges to negative charges in the RNA lipoplex particles is about 1.3:2.0; sodium chloride at a concentration of about 30 mM; sucrose at a concentration of about 20% (w/v); HEPES at a concentration of about 7.5 mM with a pH of about 6.2; and EDTA at a concentration of about 2.5 mM. In further specific embodiments, the RNA encodes five epitopes or ten epitopes.

F. Stability of Compositions of the Disclosure

As used herein, "stable" refers to a composition where the measured values for various physiochemical parameters are within a defined range. In one embodiment, the composition is analyzed to assess stability according to various parameters. According to the present disclosure, stability parameters include, without limitation, average diameter of RNA lipoplex particles, polydispersity index, integrity of RNA, RNA content, pH, osmolality, and the number of sub-visible particles. One of skill in the art would be able to measure such parameters using routine laboratory techniques and instrumentation. For example, stability parameters may be assessed using dynamic light scattering (DLS), light obscuration, spectrometry, agarose gel electrophoresis, bioanalyzer, or other any other suitable technique. In one embodiment, the bioanalyzer is an Agilent 2100 Bioanalyzer (Agilent Technologies) capable of measuring both integrity of RNA and RNA content. In one embodiment, the bioanalyzer is a Fragment Analyzer by Advanced Analytical.

Without wishing to be bound by theory, DLS measurements are useful for analyzing parameters related to RNA lipoplex particles of the present disclosure. In one embodiment, DLS may be used to determine the average diameter of RNA lipoplex particles, which is expressed in terms of Z-avg (a measure for the average particle size). In another embodiment, DLS may be used to determine the polydispersity index of RNA lipoplex particles, which indicates the size and weight distribution of RNA lipoplex particles.

In certain embodiments, the composition is stable when measurements for stability parameters are within a defined range. In one embodiment of a stable composition, the RNA lipoplex particles have an average diameter that differs from the original average diameter (i.e. the average diameter prior to freezing, freeze-drying, or spray-drying and thawing or reconstitution) by no more than ±20%, ±10%, ±5%, or ±3% after storage, e.g., after storage at a temperature from about −15° C. to about −40° C. In one embodiment of a stable composition, the RNA lipoplex particles have an average diameter that is not greater than 20%, 10%, 5%, or 3% compared to the original average diameter (i.e. the average diameter prior to freezing, freeze-drying, or spray-drying and thawing or reconstitution) after storage, e.g., after storage at a temperature from about −15° C. to about −40° C. In another embodiment of a stable composition, the RNA lipoplex particles have a polydispersity index that differs from the original polydispersity index (i.e. the polydispersity index prior to freezing, freeze-drying, or spray-drying and thawing or reconstitution) by no more than ±20%, ±10%, ±5%, or ±3% after storage, e.g., after storage at a temperature from about −15° C. to about −40° C. In one embodiment, a stable composition has no more than 6,000 sub-visible particles with a diameter greater than or equal to 10 μm after storage, e.g., after storage at a temperature from about −15° C. to about −40° C. In one embodiment, a stable composition has no more than 600 sub-visible particles with a diameter greater than or equal to 25 μm after storage, e.g., after storage at a temperature from about −15° C. to about −40° C.

In one embodiment of a stable composition, the integrity of the RNA is at least 80 percent after storage, e.g., after storage at a temperature from about −15° C. to about −40° C.

In one embodiment, the composition is stable at a storage temperature from about −15° C. to about −40° C. In specific embodiments, the composition is stable at a temperature of about −15° C., about −16° C., about −17° C., about −18° C., about −19° C., about −20° C., about −21° C., about −22° C., about −23° C., about −24° C., about −25° C., about −26° C., about −27° C., about −28° C., about −29° C., about −30° C., about −31° C., about −32° C., about −33° C., about −34° C., about −35° C., about −36° C., about −37° C., about −38° C., about −39° C., or about −40° C. In a preferred embodiment, the composition is stable at a temperature of about −15° C., about −20° C., about −30° C., or about −40° C.

In one embodiment, the composition is stable at a temperature from about −15° C. to about −40° C. when the pharmaceutical composition is protected from light. In a preferred embodiment, the composition is stable at a temperature from about −15° C. to about −25° C. when the composition is protected from light.

In one embodiment, the composition is stable at a temperature from about −15° C. to about −40° C. for at least 1 month up until about 24 months. In specific embodiments, the composition is stable at a temperature from about −15° C. to about −40° C. for at least 1 month, at least 2 months, at least 3 months, at least 4 months, at least 5 months, at least 6 months, at least 7 months, at least 8 months, at least 9 months, at least 10 months, at least 11 months, at least 12 months, at least 13 months, at least 14 months, at least 15 months, at least 16 months, at least 17 months, at least 18 months, at least 19 months, at least 20 months, at least 21 months, at least 22 months, at least 23 months, at least 24 months, at least 25 months, at least 26 months, at least 27 months, at least 28 months, at least 29 months, at least 30 months, at least 31 months, at least 32 months, at least 33 months, at least 34 months, at least 35 months, or at least 36 months.

In a preferred embodiment, the composition is stable at a temperature of about −15° C. for at least 1 month, at least 2 months, at least 3 months, at least 4 months, at least 5 months, or at least 6 months.

In another preferred embodiment, the composition is stable at a temperature of about −20° C. for at least 1 month, at least 2 months, at least 3 months, at least 4 months, at least 5 months, or at least 6 months.

In still another preferred embodiment, the composition is stable at a temperature of about −30° C. for at least 1 month, at least 2 months, at least 3 months, at least 4 months, at least 5 months, or at least 6 months.

In one embodiment, the composition is stable after freezing at a temperature from about −15° C. to about −40° C. and thawing to a temperature from about 4° C. to about 25° C. (ambient temperature).

In another embodiment, the composition is stable after freezing at a temperature from about −15° C. to about −40° C. and thawing to a temperature from about 4° C. to about 25° C. (ambient temperature) in multiple freeze-thaw cycles.

G. Physical State of Compositions of the Disclosure

In embodiments, the composition of the present disclosure is a liquid or a solid. Non-limiting examples of a solid include a frozen form or a lyophilized form. In a preferred embodiment, the composition is a liquid.

Pharmaceutical Compositions of the Disclosure

The compositions comprising RNA lipoplex particles described herein are useful as or for preparing pharmaceutical compositions or medicaments for therapeutic or prophylactic treatments.

The particles of the present disclosure may be administered in the form of any suitable pharmaceutical composition.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation. In the context of the present disclosure, the pharmaceutical composition comprises RNA lipoplex particles as described herein.

The pharmaceutical compositions of the present disclosure preferably comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cyctokines, such as monokines, lymphokines, interleukins, chemokines. The chemokines may be IL-1, IL-2, IL-3, IL-4, IL-5, IL-6, IL-7, IL-8, IL-9, IL-10, IL-12, INFa, INF-γ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the particles or compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the particles or compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

Routes of Administration of Pharmaceutical Compositions of the Disclosure

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical compositions is formulated for systemic administration. In another preferred embodiment, the systemic administration is by intravenous administration.

Articles of Manufacture

In one aspect, RNA lipoplex particles described herein are present in a pharmaceutical composition. In another aspect, a composition described herein is a pharmaceutical composition.

In one aspect, the disclosure relates to a vial containing a pharmaceutical composition described herein. In another aspect, the disclosure relates to a syringe containing a pharmaceutical composition described herein.

Use of Pharmaceutical Compositions of the Disclosure

RNA lipoplex particles described herein may be used in the therapeutic or prophylactic treatment of various diseases, in particular diseases in which provision of a peptide or protein to a subject results in a therapeutic or prophylactic effect. For example, provision of an antigen or epitope which is derived from a virus may be useful in the treatment of a viral disease caused by said virus. Provision of a tumor antigen or epitope may be useful in the treatment of a cancer disease wherein cancer cells express said tumor antigen.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In embodiments of the present disclosure, the "individual" or "subject" is a "patient".

The term "patient" means an individual or subject for treatment, in particular a diseased individual or subject.

In one embodiment of the disclosure, the aim is to provide an immune response against diseased cells expressing an antigen such as cancer cells expressing a tumor antigen, and to treat a disease such as a cancer disease involving cells expressing an antigen such as a tumor antigen.

A pharmaceutical composition comprising RNA lipoplex particles as described herein comprising RNA encoding a peptide or protein that comprises one or more antigens or one or more epitopes may be administered to a subject to elicit an immune response against the one or more antigens or one or more epitopes in the subject which may be therapeutic or partially or fully protective. A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. A cellular immune response includes, without limitation, a cellular response directed to cells expressing an antigen and being characterized by presentation of an antigen with class I or class II MHC molecule. The cellular response relates to T lymphocytes, which may be classified as helper T cells (also termed CD4+ T cells) that play a central role by regulating the immune response or killer cells (also termed cytotoxic T cells, CD8+ T cells, or CTLs) that induce apoptosis in infected cells or cancer cells. In one embodiment, administering a pharmaceutical composition of the present disclosure involves stimulation of an anti-tumor CD8+ T cell response against cancer cells expressing one or more tumor antigens. In as specific embodiment, the tumor antigens are presented with class I MHC molecule.

The present disclosure contemplates an immune response that may be protective, preventive, prophylactic and/or therapeutic. As used herein, "induces [or inducing] an immune response" may indicate that no immune response against a particular antigen was present before induction or it may indicate that there was a basal level of immune response against a particular antigen before induction, which was enhanced after induction. Therefore, "induces [or inducing] an immune response" includes "enhances [or enhancing] an immune response".

The term "immunotherapy" relates to the treatment of a disease or condition by inducing, or enhancing an immune response. The term "immunotherapy" includes antigen immunization or antigen vaccination.

The terms "immunization" or "vaccination" describe the process of administering an antigen to an individual with the purpose of inducing an immune response, for example, for therapeutic or prophylactic reasons.

In one embodiment, the present disclosure envisions embodiments wherein RNA lipoplex particles as described herein targeting spleen tissue are administered. The RNA encodes a peptide or protein comprising an antigen or an epitope as described, for example, herein. The RNA is taken up by antigen-presenting cells in the spleen such as dendritic cells to express the peptide or protein. Following optional processing and presentation by the antigen-presenting cells an immune response may be generated against the antigen or epitope resulting in a prophylactic and/or therapeutic treatment of a disease involving the antigen or epitope. In one embodiment, the immune response induced by the RNA lipoplex particles described herein comprises presentation of an antigen or fragment thereof, such as an epitope, by antigen presenting cells, such as dendritic cells and/or macrophages, and activation of cytotoxic T cells due to this presentation. For example, peptides or proteins encoded by the RNAs or procession products thereof may be presented by major histocompatibility complex (MHC) proteins expressed on antigen presenting cells. The MHC peptide complex can then be recognized by immune cells such as T cells or B cells leading to their activation.

Thus, in one embodiment the RNA in the RNA lipoplex particles described herein, following administration, is delivered to the spleen and/or is expressed in the spleen. In one embodiment, the RNA lipoplex particles are delivered to the spleen for activating splenic antigen presenting cells. Thus, in one embodiment, after administration of the RNA lipoplex particles RNA delivery and/or RNA expression in antigen presenting cells occurs. Antigen presenting cells may be professional antigen presenting cells or non-professional antigen presenting cells. The professional antigen presenting cells may be dendritic cells and/or macrophages, even more preferably splenic dendritic cells and/or splenic macrophages.

Accordingly, the present disclosure relates to RNA lipoplex particles or a pharmaceutical composition comprising RNA lipoplex particles as described herein for inducing or enhancing an immune response, preferably an immune response against cancer.

In a further embodiment, the present disclosure relates to RNA lipoplex particles or a pharmaceutical composition comprising RNA lipoplex particles as described herein for use in a prophylactic and/or therapeutic treatment of a disease involving an antigen, preferably a cancer disease.

In a further embodiment, the present disclosure relates to a method for delivering an antigen or an epitope of an antigen to antigen presenting cells, such as professional antigen presenting cells, in the spleen, or expressing an antigen or an epitope of an antigen in antigen presenting cells, such as professional antigen presenting cells, in the spleen comprising administering to a subject RNA lipoplex particles or a pharmaceutical composition comprising RNA lipoplex particles as described herein. In one embodiment, the antigen is a tumor antigen. In this aspect, the antigen or an epitope of an antigen is preferably encoded by the RNA in the RNA lipoplex particles.

In one embodiment, systemically administering RNA lipoplex particles or a pharmaceutical composition comprising RNA lipoplex particles as described herein results in targeting and/or accumulation of the RNA lipoplex particles or RNA in the spleen and not in the lung and/or liver. In one embodiment, RNA lipoplex particles release RNA in the spleen and/or enter cells in the spleen. In one embodiment, systemically administering RNA lipoplex particles or a pharmaceutical composition comprising RNA lipoplex particles as described herein delivers the RNA to antigen presenting cells in the spleen. In a specific embodiment, the antigen presenting cells in the spleen are dendritic cells or macrophages.

In a further embodiment, the present disclosure relates to a method for inducing or enhancing an immune response in a subject comprising administering to the subject RNA lipoplex particles or a pharmaceutical composition comprising RNA lipoplex particles as described herein. In an exemplary embodiment, the immune response is against cancer.

The term "macrophage" refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen. Peptides from degraded proteins are displayed on the macrophage cell surface where they can be recognized by T cells, and they can directly interact with antibodies on the B cell surface, resulting in T and B cell activation and further stimulation of the immune response. Macrophages belong to the class of antigen presenting cells. In one embodiment, the macrophages are splenic macrophages.

The term "dendritic cell" (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term "antigen presenting cell" (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term "professional antigen presenting cells" relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term "non-professional antigen presenting cells" relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term "disease involving an antigen" or "disease involving an epitope" refers to any disease which implicates an antigen or epitope, e.g. a disease which is characterized by the presence of an antigen or epitope. The disease involving an antigen or epitope can be an infectious disease, or a cancer disease or simply cancer. As mentioned above, the antigen may be a disease-associated antigen, such as a tumor-associated antigen, a viral antigen, or a bacterial antigen and the epitope may be derived from such antigen.

The term "infectious disease" refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the disclosure also comprises cancer metastases.

Combination strategies in cancer treatment may be desirable due to a resulting synergistic effect, which may be considerably stronger than the impact of a monotherapeutic approach. In one embodiment, the pharmaceutical composition is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. A monoclonal antibody may induce cell death via antibody-dependent cell mediated cytotoxicity (ADCC), or bind complement proteins, leading to direct cell toxicity, known as complement dependent cytotoxicity (CDC). Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ3), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-1), Gemtuzumab ozogamicin (CD33), Gevokizumab (IL-43), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDCI), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL-5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL-6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA-4), Tigatuzumab (TRAIL-R2), TNX-650 (IL-13), Tositumomab (CD20), Trastuzumab (HER2/neu), TRBS07 (GD2), Tremelimumab (CTLA-4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanolimumab (CD4).

In one embodiment, the immunotherapeutic agent is a PD-1 axis binding antagonist. A PD-1 axis binding antagonist includes but is not limited to a PD-1 binding antagonist, a PD-L1 binding antagonist and a PD-L2 binding antagonist. Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific embodiment, PD-L1 binding partners are PD-1 and/or B7-1. In another embodiment, the PD-L2 binding antagonist is a molecule that inhibits the binding of PD-L2 to its binding partners. In a specific embodiment, the PD-L2 binding partner is PD-1. The PD-1 binding antagonist may be an antibody, an antigen binding fragment thereof, an immunoadhesin, a fusion protein, or oligopeptide. In some embodiments, the PD-1 binding antagonist is an anti-PD-1 antibody (e.g., a human antibody, a humanized antibody, or a chimeric antibody). Examples of an anti-PD-1 antibody include, without limitation, MDX-1106 (Nivolumab, OPDIVO), Merck 3475 (MK-3475, Pembrolizumab, KEYTRUDA), MEDI-0680 (AMP-514), PDR001, REGN2810, BGB-108, and BGB-A317.

In one embodiment, the PD-1 binding antagonist is an immunoadhesin that includes an extracellular or PD-1 binding portion of PD-L1 or PD-L2 fused to a constant region. In one embodiment, the PD-1 binding antagonist is AMP-224 (also known as B7-DCIg, is a PD-L2-Fc), which is fusion soluble receptor described in WO2010/027827 and WO2011/066342.

In one embodiment, the PD-1 binding antagonist is an anti-PD-L1 antibody, including, without limitation, YW243.55.S70, MPDL3280A (Atezolizumab), MEDI4736 (Durvalumab), MDX-1105, and MSB0010718C (Avelumab).

In one embodiment, the immunotherapeutic agent is a PD-1 binding antagonist. In another embodiment, the PD-1 binding antagonist is an anti-PD-L1 antibody. In an exemplary embodiment, the anti-PD-L1 antibody is Atezolizumab.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Materials

Notable materials used for the experiments described hereinafter were:

| Material | Company. Article Nr. |
|---|---|
| R-DOTMA | Merck & Cie. 5000249.2900-10G |
| DOPE | CordenPharma. LP-04-069 |
| Ethanol abs. | VWR chemicals. 20821.365 |
| Water | Aqua B.Braun. 0082479E |
| Minisart 0.45 µm | Sartorius Stedim. 16555-K |
| Minisart 0.8 µm | Sartorius Stedim. 17593-K |
| Minisart 1.2 µm | Sartorius Stedim. 17593-K |
| Minisart 5 µm | Sartorius Stedim. 17594-K |
| BD microlance 3 | 0.9 × 40 mm. 301300 |
| Injekt-F 1 mL | B. Braun. 9166017V |
| 5M NaCl solution | Ambion. AM9760G |
| Luc-RNA | RNA coding for Luciferase; generated from Biontech RNA Pharmaceuticals |

Example 2: Preparation of Lipid Mixtures

DOTMA/DOPE lipid mixture prepared at different lipid concentrations in ethanol with a lipid molar ratio 2:1 respectively. The solution is prepared as follow:

Weigh DOPE lipid.
Calculate the amount of DOTMA to keep the % molar ratio of 2:1 DOTMA/DOPE.
Weigh DOTMA lipid.
Calculate the amount of ethanol absolute necessary to dissolve the lipids.
Weigh Ethanol abs.
Dissolve the lipids in ethanol with the aid of water bad at 37° C.

DOPE and DOPE/DOTMA solubility in ethanol was investigated by preparing 300 mM DOPE or 330 mM DOPE/DOTMA (66:33) solutions in ethanol. The lipids were dissolved by incubating the lipid solutions at 37° C. for 20 minutes. The DOPE solutions were centrifuged at 17000 G for 1 h and the DOPE concentration was measured in the supernatant by HPLC. The DOTMA/DOPE solutions were filtered through a 0.22 µm PES syringe filter and the lipid concentration was measured in the filtrate by HPLC.

Further lipid mixtures which can be prepared likewise by following the basic steps described in this example, provided that other lipids are used as starting materials and/or other molar ratios are calculated.

Example 3: Preparation of Liposomes

Liposomes were prepared by ethanol injection as follows:
0.2 mL DO™/DOPE or (other lipid solution) in ethanol was injected with the aid of a 1 mL syringe equipped with a 0.9×40 mm needle into 9.8 mL water under stirring at 120 rpm. The liposome colloid was stirred for 30 minutes. The liposomes were filtered or not through a 0.45 or 1.2 or 5 μm CA syringe filters. The liposome colloids were stored at 4-8° C. The DOTMA/DOPE lipid solutions were prepared in at 66:33% molar ratio at different total lipid concentrations, from 100 to 400 mM with intermediate steps of 50 mM.

Example 4: Preparation of RNA Lipoplexes

RNA lipoplex formulations were prepared as follows by firstly mixing an RNA solution (e.g luc-RNA solution) with a NaCl solution to pre-condense the luc-RNA. After this, the liposome colloid and the luc-RNA-NaCl solution were mixed to form the RNA lipoplexes. The RNA lipoplex formulation was incubated at room temperature for 10 minutes and stored at 4-8° C. The different RNA lipoplex formulations were e.g. prepared with an N/P ratio of 0.65. The RNA concentration in these different RNA lipoplex formulations was 0.1 mg/mL and the NaCl concentration was 50 mM. Different liposome precursors (different sizes) were used for the preparation of the RNA lipoplexes.

Example 5: Dynamic Light Scattering

Liposome sizes and RNA lipoplex sizes were measured by the known method of Dynamic Light Scattering (DLS) using a Nicomp instrument (PSS. Santa Barbara. USA). Liposome samples were diluted with water to 1 mM total lipid concentration. RNA lipoplex samples were diluted 1 to 5 with 0.9% NaCl solution. The samples were measured in 5×50 mm culture tubes (Kimble. USA).

Example 6: Light Obscuration—Dynamic Light Scattering

The particle counting/measurement from the different liposomes and RNA lipoplex formulations in a size range between 0.5-5 μm were performed using an Accusizer A7000 instrument (PSS. Santa Barbara. USA). Three measurements of a volume of 5 mL (2.5 μL sample/20 mL free particle water) were performed. The obtained results represented the mean value of the amount of particles of three measurements.

Example 7: Small Angle X-Ray Scattering

Internal structure parameters of different RNA lipoplex formulations prepared with different liposome precursors was measured by Small Angel X-ray Scattering (SAXS). SAXS is a technique by which nanoscale density differences in a sample can be quantified by analyzing the elastic scattering behaviour of X-rays when travelling through the material, recording their scattering at small angles. Correlation length and d-spacing parameters were calculated for every RNA-formulation tested. RNA lipoplex formulations were prepared with an N/P ratio of 0.65, 0.1 mg/mL RNA and 112 mM NaCl.

Example 8: Agarose Gel Electrophoresis

The amount of free RNA in the different RNA lipoplex samples were measured by gel electrophoresis. 1% agarose gel containing sodium hypochlorite was used to perform the measurements. RNA lipoplex samples were diluted 1:6 with DNA loading dye. 12 μL of diluted RNA lipoplex samples were carefully loaded into the agarose gel. Electrophoresis was performed at 80V with a run time of 40 min.

Example 9: HPLC

Lipid concentration in the different liposome formulations were measured by HPLC (Agilent technologies. Santa Clara. USA) using a Sunfire C18 2.5 μm 4.6×75 mm column (Waters. Mass. USA) and a wave length of 205 nm. Mobile phase A was a mixture of 70% methanol/30% isopropanol/0.1% TFA, mobile phase B was a mixture of 55% methanol/15% isopropanol/30% water/0.1% TFA. Liposomes samples were or not diluted with water to 3 mM total lipid concentration.

Example 10: Cell Culture: RNA Transfection in Dendritic Cells In Vitro

RNA lipoplex formulations were prepared with different liposome precursors and luc-RNA. The RNA lipoplexes were diluted to 0.01 mg/mL RNA with 0.9% NaCl solution for cell culture experiments. RNA transfection efficiency of the different RNA lipoplex formulations was investigated in human dendritic cells seeded in medium or whole blood.

Example 11: Animal Model: Spleen Targeting and RNA Transfection in Dendritic Cells Transfection efficiency of different RNA lipoplex formulations was investigated in BALB/c mice. 20 μg formulated RNA lipoplexes were retro-orbital injected and luciferase expression in dendritic cells (spleen target) was measured after 6 hours. RNA lipoplexes were prepared with luc-RNA and different liposome precursors, small or large liposomes obtained from raw colloids and small and large liposomes after 0.45 μm filtration, N/P ratio 0.65 and 112 mM NaCl.

Example 12: Solubility Testing

It has been tested if DOPE-containing solutions of higher concentration can be prepared (in the supersaturated state) and used for ethanol injection for liposome manufacturing (next section). Results obtained in this solubility test series are shown in Tables 1 and 2:

TABLE 1

Solubility of DOPE lipid in ethanol obtained from different providers.
DOPE solubility in ethanol

| Provider | Charge Nr. | mM |
|---|---|---|
| Corden Pharma | F0624 | 56 |
| Corden Pharma | W0650 | 59 |
| NOF | 14099612 | 63 |
| Merck | MK2885-C | 59 |

TABLE 2

Increased solubility of DOPE lipid in a DOTMA/DOPE lipid mixture with a % molar ratio of 66:33 prepared in ethanol abs.
DOPE solubility in ethanol comprising 220 mM DOTMA

| Provider | Charge Nr. | mM after Filtration |
|---|---|---|
| Corden Pharma | F0624 | 93 |
| Corden Pharma | W0650 | 106 |
| NOF | 14099612 | 103 |
| Merck | MK2885-C | 94 |

According to these results, DOPE as purchased from different providers has an equilibrium solubility in ethanol of about 50 to 60 mM (room temperature). However, if a co-solution with the cationic lipid DOTMA is prepared, the equilibrium solubility increases significantly, for example to about 90 to 100 mM if a DOTMA/DOPE co-solution with a molar ratio of 66:33 is used.

Example 13: Manufacturing of Liposomes of Different Sizes

Liposomes were manufactured by ethanol injection using the protocol as described in Example 3. No filtration process was performed after ethanol injection. The lipid concentration in ethanol was varied, keeping all other parameters fixed. Liposome sizes and were measured as described by Dynamic Light Scattering (DLS) in Examples 5 and 6.

Figure 2:
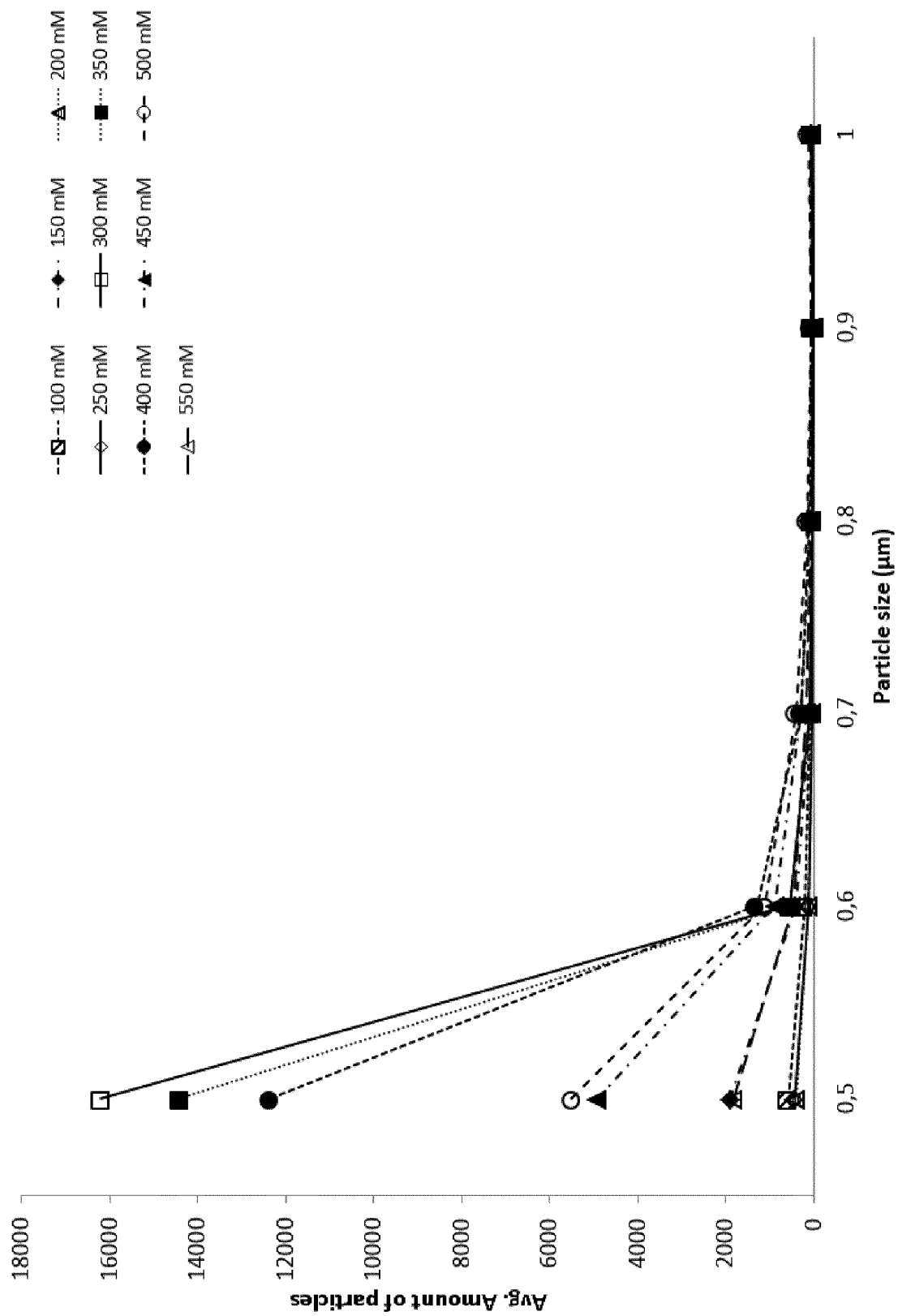
FIG. 2 shows the amount of particles present in the DOTMA/DOPE liposome formulations prepared with different lipid solutions at different concentrations.

As an example, results relating to liposomes obtained from a DOTMA/DOPE mixture with a % molar ratio 66:33 are shown in Table 3 (below) and FIGS. 1 and 2.

TABLE 3

Dependency of the sizes of liposomes on different lipid concentrations in the stock solution.

| Lipid stock sol. | Liposome Size (nm) raw colloid | | | Stat. Size | |
|---|---|---|---|---|---|
| mM | 1 | 2 | 3 | $\dot{X}$ | σ |
| 100 | 28 | 32 | | 30 | 2.83 |
| 150 | 36 | 35 | 34 | 35 | 1 |
| 200 | 82 | 76 | 74 | 76 | 4.16 |
| 250 | 202 | 195 | 194 | 195 | 4.36 |
| 300 | 371 | 220 | 369 | 369 | 86.61 |
| 350 | 620 | 644 | 652 | 644 | 16.65 |
| 400 | 665 | 665 | 740 | 665 | 43.3 |
| 450 | 721 | 783 | 723 | 723 | 35.23 |
| 500 | 739 | 767 | 766 | 766 | 15.89 |
| 550 | 770 | 754 | 656 | 754 | 61.72 |

As can be seen, the obtained sizes (Z-average) of the liposomes increase with the lipid concentration in the ethanol solution used for the ethanol injection. Thus, the lipid concentration in ethanol can be efficiently used for controlling the size of the liposomes. Interestingly, the size change was most prominent if the DOPE concentration was below and above the equilibrium solubility of DOPE in ethanol alone. If the DOPE concentration was above 50 mM (150 mM total lipid concentration) the obtained liposome size increased drastically, from <50 nm to more than 500 nm (FIG. 1). However, also above the solubility limit the liposomes size further monotonously increased with increasing lipid concentration.

A 0.5 μm liposomes fraction was present in all liposome formulations, this liposome fraction was higher in the liposomes prepared with a 300 mM lipid solution and decreased in the liposomes prepared at lower and higher lipid concentrations. Furthermore, 0.6 μm and 0.7 μm liposome fractions were measured in the liposome formulations prepared at higher lipid concentrations (FIG. 2). After ethanol injection of a high concentrated lipid solution, larger liposomes were formed. The total amount of liposomes formed was lower in comparison to the liposome formulations prepared at low lipid concentration in the lipid solution. The obtained results represented the mean value of the amount of particles of three measurements.

Example 14: Manufacturing of RNA Lipoplexes from Liposomes of Different Sizes RNA lipoplexes were manufactured as described in Example 4 using different liposome precursors, where the size of liposomes for their formation were varied, keeping all other parameters fixed. Liposome sizes (z-average) and polydispersity indices (PDI) were determined in the course of Dynamic Light Scattering (DLS) experiments as described in Examples 5 and 6. Results relating to the impact of the lipid concentrations for liposome preparation (and thus on liposome precursor size) on the RNA lipoplex sizes (Z-average) are shown in Table 4 (below) and corresponding FIGS. 3 and 4.

TABLE 4

Amount of particles present in the RNA lipoplex formulations prepared with different liposome precursors (non-filtered liposomes). The amount of 0.5 μm particles increases in the RNA lipoplex formulations prepared with larger liposomes. The liposomes were prepared by ethanol injection using different lipid stock solutions at different concentrations. Size of the liposomes increases with the lipid concentration in the stock solution.
RNA lipoplex size measurements

| Lipid sol. | Z-average (nm) | | | PDI | | | Z-average stat. (nm) | | PDI stat. | |
|---|---|---|---|---|---|---|---|---|---|---|
| mM | 1 | 2 | 3 | 1 | 2 | 3 | $\dot{X}$ | Std. Dev. | $\dot{X}$ | Std. Dev. |
| 100 | 196 | 200 | 190 | 0.136 | 0.171 | 0.186 | 195.07 | 4.82 | 0.16 | 0.03 |
| 150 | 208 | 220 | 187 | 0.3 | 0.165 | 0.17 | 205.03 | 17.04 | 0.21 | 0.08 |
| 200 | 189 | 207 | 212 | 0.093 | 0.125 | 0.14 | 202.43 | 11.81 | 0.12 | 0.02 |
| 250 | 208 | 282 | 270 | 0.3 | 0.203 | 0.202 | 253.17 | 39.61 | 0.24 | 0.06 |
| 300 | 473 | 476 | 475 | 0.432 | 0.372 | 0.356 | 474.7 | 1.41 | 0.39 | 0.04 |
| 350 | 448 | 479 | 485 | 0.294 | 0.407 | 0.402 | 470.83 | 19.99 | 0.37 | 0.06 |
| 400 | 465 | 447 | 415 | 0.424 | 0.295 | 0.292 | 442.03 | 25.29 | 0.34 | 0.08 |
| 450 | 412 | 447 | 434 | 0.338 | 0.312 | 0.311 | 431.2 | 17.66 | 0.32 | 0.02 |
| 500 | 448 | 443 | 419 | 0.401 | 0.312 | 0.333 | 436.73 | 15.62 | 0.35 | 0.05 |
| 550 | 434 | 470 | 417 | 0.316 | 0.46 | 0.294 | 440.43 | 27.29 | 0.36 | 0.09 |

Figure 3:
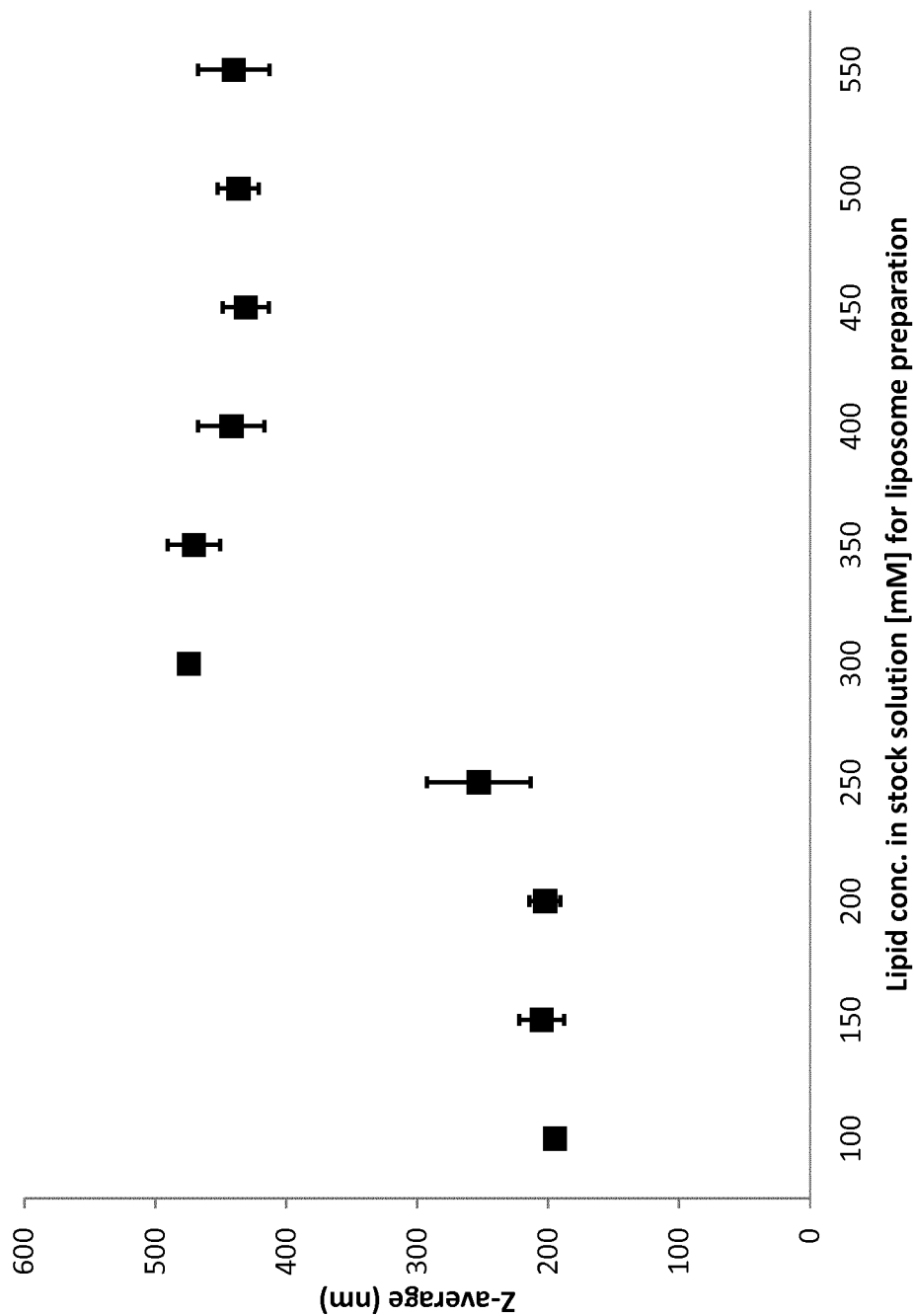
FIG. 3 shows the impact of the liposome precursor size (non-filtered liposome colloid used) on the RNA-lipoplex size. Small RNA-lipoplexes were obtained when small liposomes were used for their formation. No clear correlation between liposome size and RNA-lipoplex size was found in all RNA-lipoplex prepared with larger liposomes.

According to this test series, RNA lipoplexes obtained from small liposomes were smaller than those from large liposomes. RNA lipoplexes obtained from liposomes which were manufactured with a 300 mM solution and above were about two times larger than those from liposomes which were obtained from a 150 mM stock solution. No correlation between liposome size and RNA lipoplex size was found in all RNA lipoplexes prepared with larger liposomes (FIG. 3).

Figure 4:
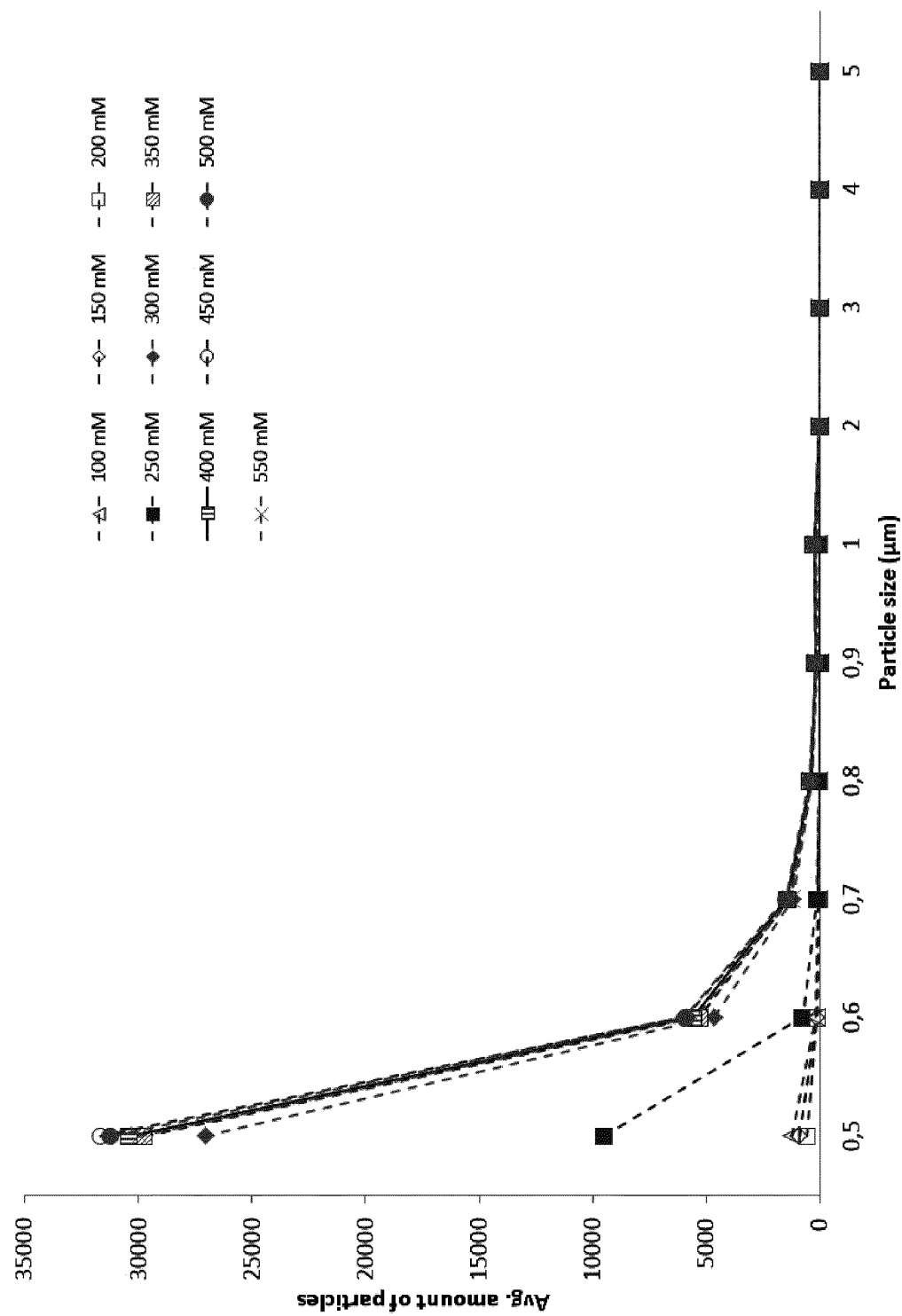
FIG. 4 shows the amount of particles present in the RNA-lipoplex formulations prepared with different liposome precursors (non-filtered liposomes). The amount of 0.5 µm particles increases in the RNA-lipoplex formulations prepared with larger liposomes. The liposomes were prepared by ethanol injection using different lipid stock solutions at different concentrations.

The obtained amount of RNA-lipoplex increased with the size of the liposome used for their formation. Higher amounts of larger RNA-lipoplexes particles were measured in the formulations prepared with larger liposomes confirming the data obtained from the dynamic light scattering measurements (FIG. 4). The obtained results represented the mean value of the amount of particles of three measurements.

Example 15: Small Angle X-Ray Scattering (SAXS) from Different Lipoplexes

Small angle X-ray scattering experiments were performed as described with RNA lipoplexes obtained from liposomes from differently concentrated stock solutions. For example, the RNA lipoplexes were formed from DOTMA/DOPE 2/1 (mol/mol) liposomes, and RNA at a charge ratio of 1.3 to 2. Liposomes were manufactured by ethanol injection as described from lipid concentrations in ethanol of 100 mM, 300 mM and 400 mM.

Figure 5:
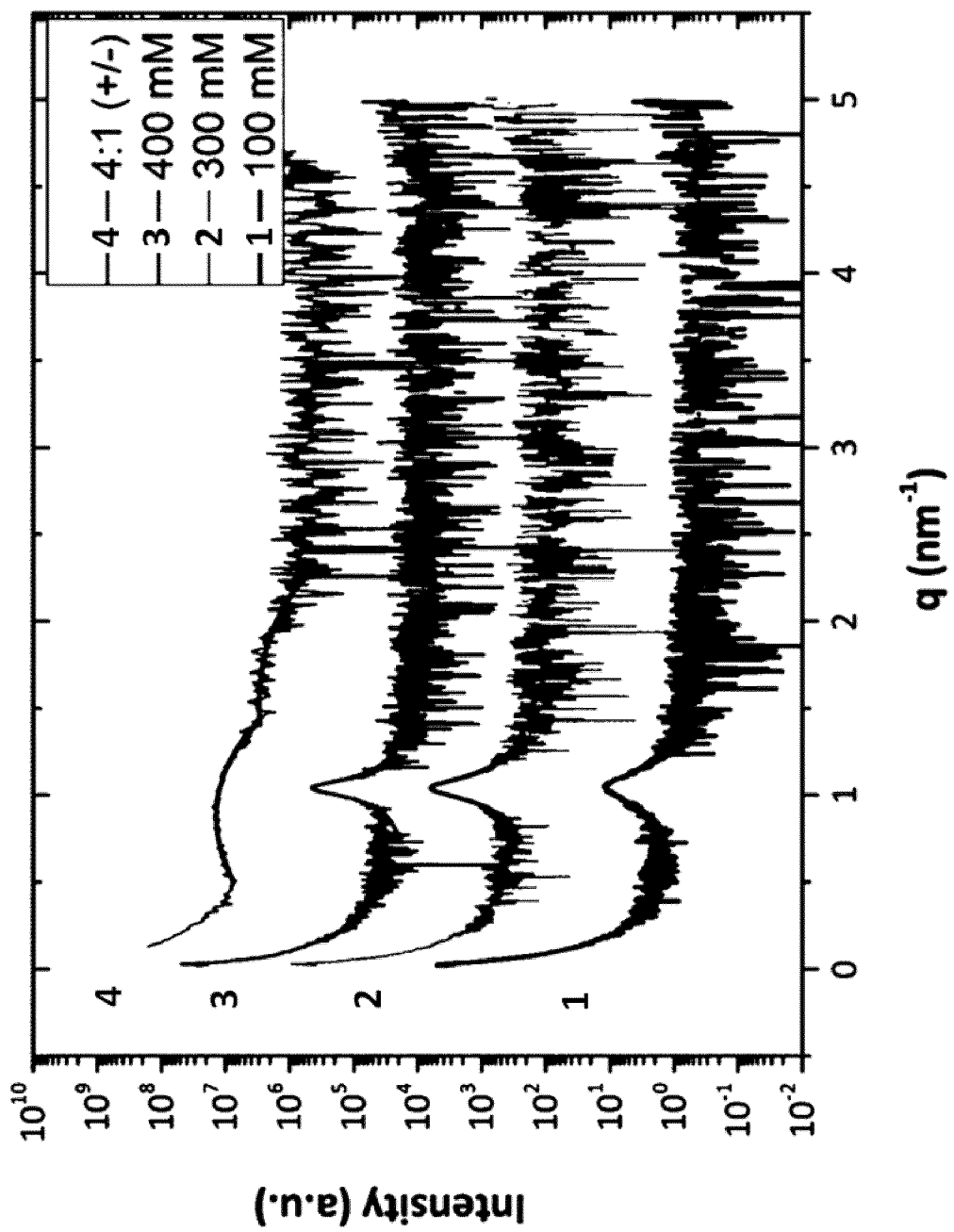
FIG. 5 shows diffraction curves obtained from SAXS measurements from RNA-Lipoplex formed with liposomes prepared at a charge ratio of 4/1 (top) and at a charge ratio of 1.3/2, where the liposomes for lipoplex formation were obtained with mM lipid stock solution in ethanol of 400 mM, 300 mM and 100 mM.

The diffraction curves obtained from Small Angle X-Ray Scattering measurements from RNA lipoplexes formed with liposomes prepared at a charge ratio of 4/1 (top) and at a charge ratio of 1.3/2, where the liposomes for lipoplex formation were obtained with mM lipid stock solution in ethanol of 400 mM, 300 mM and 100 mM, are shown in FIG. 5.

The scattering patterns comprise a single Bragg peak at around 1 $nm^{-1}$. This is the typical diffraction pattern for spleen targeting lipoplexes where an excess of (negatively charged) RNA was used for lipoplex formation. If the lipoplexes are not negatively charged, the scattering profile is completely different. As an example, RNA lipoplexes at a +/−4/1 charge ratio were measured, where much less pronounced peaks are found. As well a second order peak (although low in intensity) is discernible. In fact, general feature of x-ray scattering profiles of lipoplexes is that there are several peaks which may be equidistant of may have other spacings, depending on the phase state. Here. In contrary, only one single peak is determined. Furthermore, the peak width changes depending on the concentration of the stock solution which was originally used for liposome manufacturing. If the concentration in ethanol was higher, the peak width was lower. The Bragg peak indicates that the lipoplexes are regularly ordered, where the repeat distance (d-spacing) is given from the peak position as:

$$d = \frac{n \cdot 2\pi}{q_{max(n)}} \quad (1)$$

Here q is the momentum transfer, with $$q = \frac{4\pi}{\lambda}\sin\theta,$$

with n the order and $q_{max}$ the maximum position of the respective Bragg peak, λ the wavelength, and θ the angle. The d-spacing that can be derived from Bragg peaks is in the order of 6.5 nm.

The peak width, Δq, decreases with increasing number of repeat units in the stack. For a liquid crystalline array the correlation length can be given as:

$$\xi = \frac{2}{\Delta q} \quad (2)$$

For the lipoplex product here, a clear correlation of the scattering pattern with the before-mentioned lipid concentration in ethanol for liposome manufacturing and the biological activity can be derived. While the peak position is invariant, the peak width monotonously changes with the applied lipid concentration in ethanol. Increasing lipid concentration in ethanol (which leads to increasing liposome size) corresponds to decreasing peak width and therefore higher correlation length. At the same time, the biological activity increases with increasing correlation length. Thus, the described lipoplexes with improved activity, which are manufactured from liposomes for which the higher concentrated lipid stock solution in ethanol was used for manufacturing, was used, can be discerned by a clear structural feature. In addition, also by other methods, like asymmetric field flow fractionation (AF4), the described lipoplexes with improved activity can be discerned from those of lower activity.

Example 16: Transfection Efficiency of RNA Lipoplexes in Human Dendritic Cells Luc-RNA lipoplexes were manufactured as described using different liposome precursors, where the size of liposomes for their formation was varied (by varying the starting lipid concentration for their formation), keeping all other parameters fixed. Thereafter, RNA transfection efficiency of the different RNA lipoplex formulations was investigated in human dendritic cells seeded in medium or whole blood.

Figure 6:
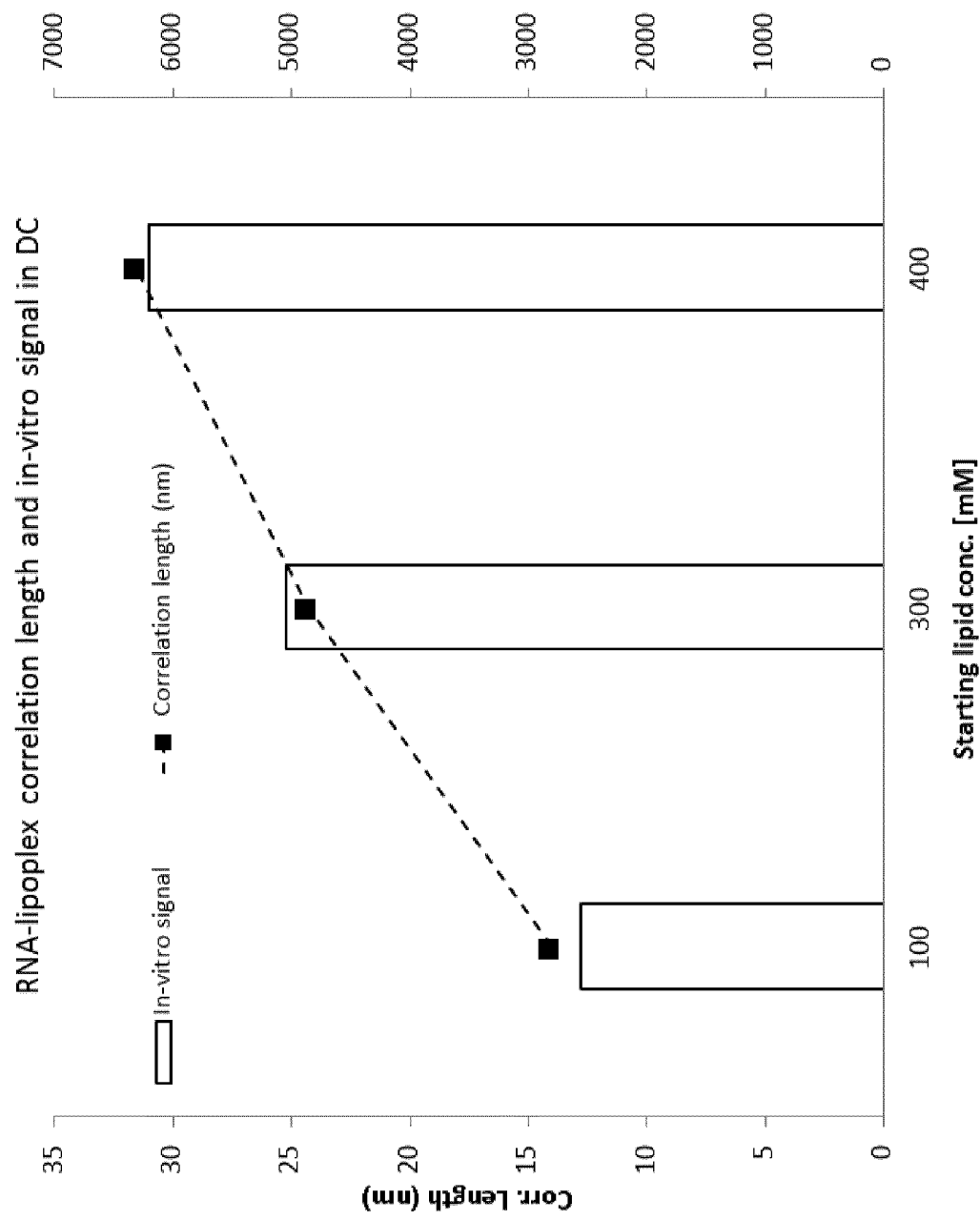
FIG. 6 shows correlation length and transfection efficiency in-vitro (human dendritic cells) of different RNA-lipoplexes prepared with different liposome precursors. Biological activity (in-vitro RNA transfection) increases monotonously with the correlation length of the RNA-lipoplex. Liposomes were prepared by ethanol injection and different lipid stock solutions prepared at different lipid concentrations.

Results illustrating the transfection efficiency in-vitro (human dendritic cells) as determined by measuring the luciferase expression and the corresponding biological activity of different RNA lipoplexes prepared with different liposome precursors are shown in FIG. 6.

Biological activity (in-vitro RNA transfection) increases monotonously with the correlation length of the RNA lipoplexes. A higher correlation length indicates a more homogenous population of lipid bilayers in the RNA lipoplex.

Example 17: Asymmetric Flow Field Flow Fractionation of Different Lipoplexes Asymmetrical flow field flow fractionation (AF4), nowadays a common and state-of-the art method for fractionation and separation of particles in a suspension, was used to determine further differences of RNA lipoplexes. According to the AF4 theory, particles with similar properties and equal size should elute at the same time.

Figure 7:
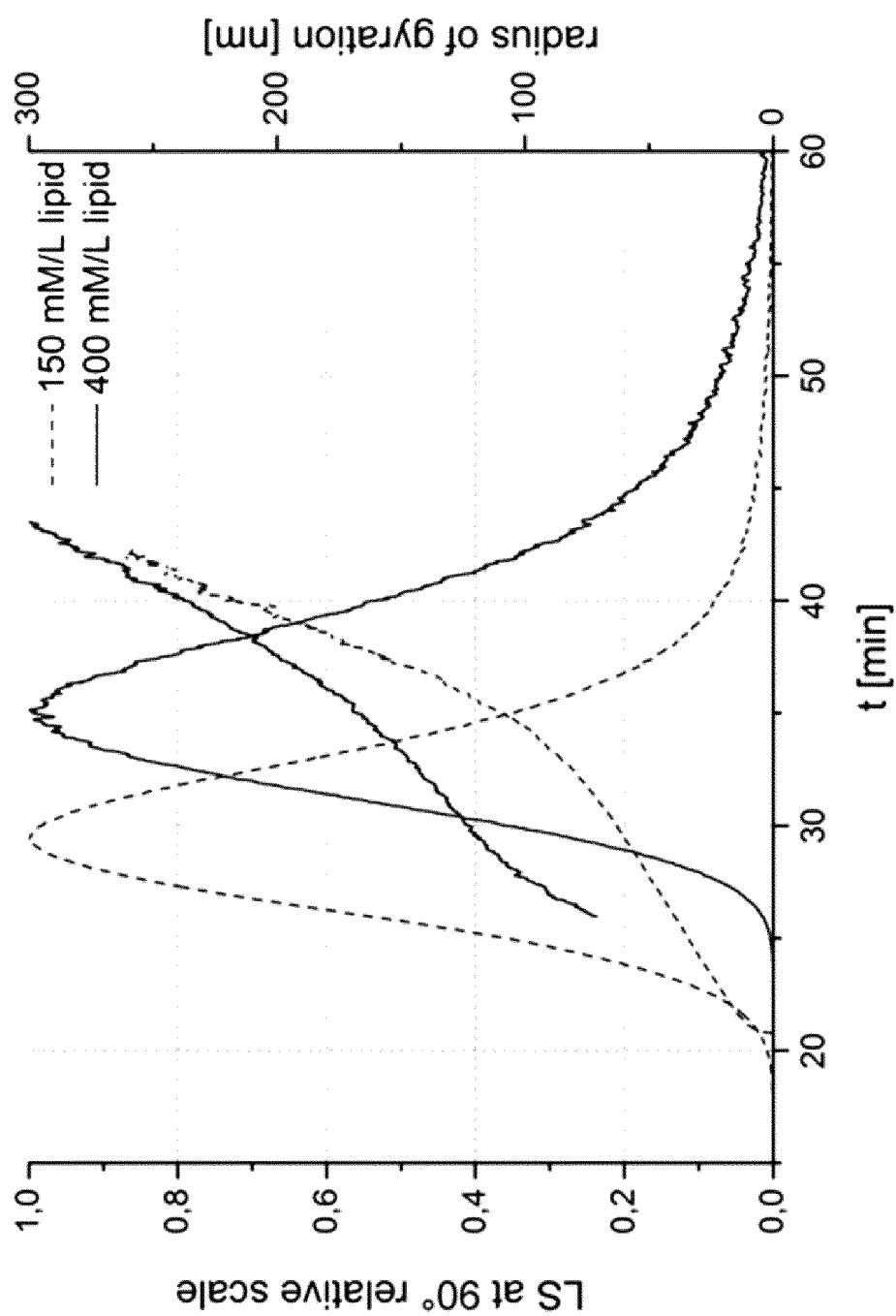
FIG. 7 shows AF4 measurements of lipoplexes from two different types of liposomes, either manufactured from a 150 mM stock solution in ethanol, or from a 400 mM stock solution in ethanol.

Some results relating to the AF4 measurements of lipoplexes from two different types of liposomes, either manufactured from a 150 mM stock solution in ethanol, or from a 400 mM stock solution in ethanol are shown in FIG. 7.

In summary, measurements of Field-Flow-Fractionation demonstrate that lipoplexes from liposomes from 150 mM lipid concentration in ethanol are qualitatively and quantitatively different from those from 400 mM lipid concentration. The 150 mM derived lipoplexes are smaller but, contraintuitively, elute later, hence there must be a qualitative difference (shape, medium interactions, charge) between the two moieties. RNA lipoplexes from the 150 mM ethanol solution elute later, although they are smaller in size. This indicates that RNA lipoplexes from liposomes which are manufactured from liposomes where 150 mM lipid solution in ethanol was used are in the average smaller than those from 400 mM lipid in ethanol. Even at the same size, the 150 mm derived lipoplexes have different physicochemical properties than the 400 mM derived ones. These differences in size and physicochemical properties are correlated with the higher biological activity of the 400 mM derived RNA lipoplexes.

Example 18: Biological Activity of RNA Lipoplexes In Vitro

Figure 8:
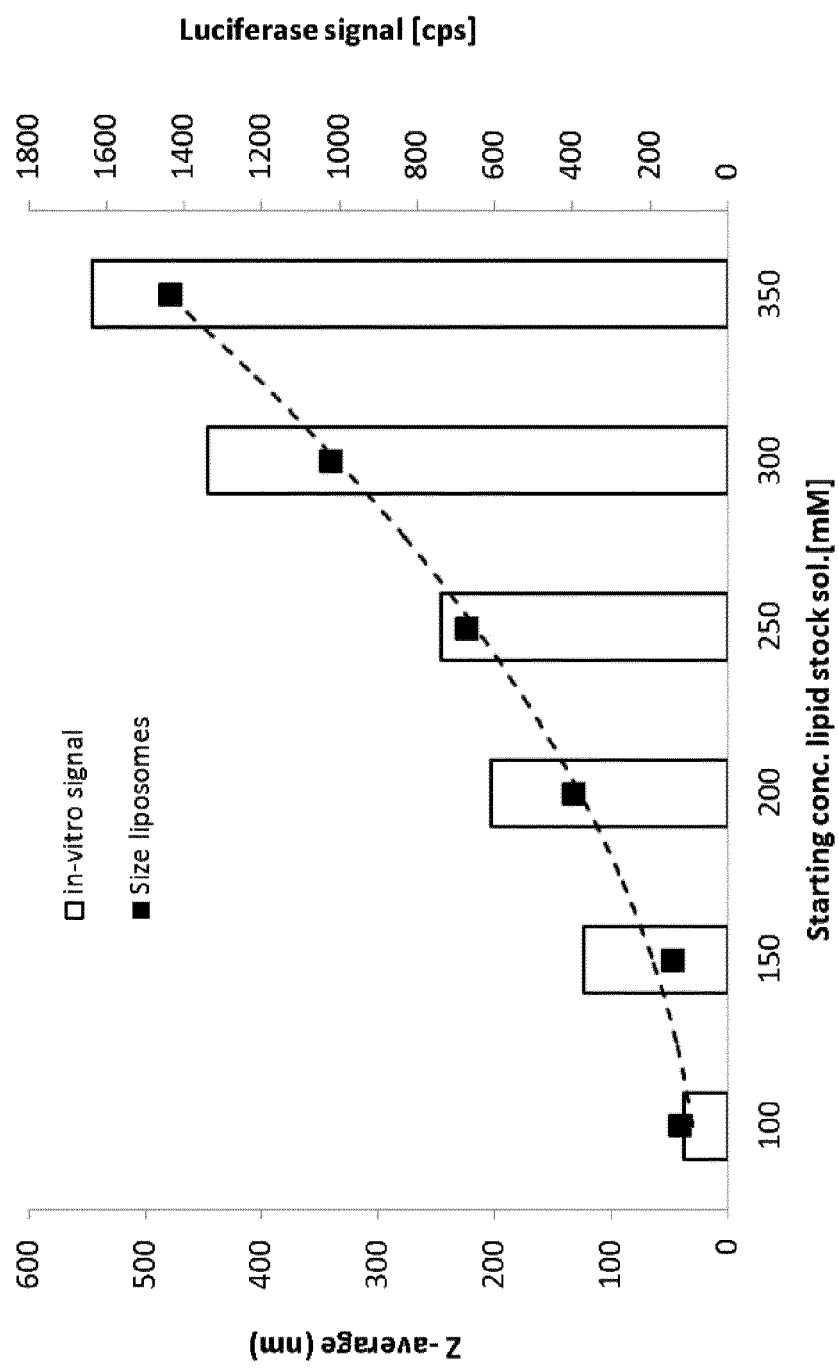
FIG. 8 shows in-vitro transfection efficiency of different RNA-lipoplex in dendritic cells. Luciferase signal increase monotonously with the liposome size used for the RNA-lipoplex formation.
Figure 9:
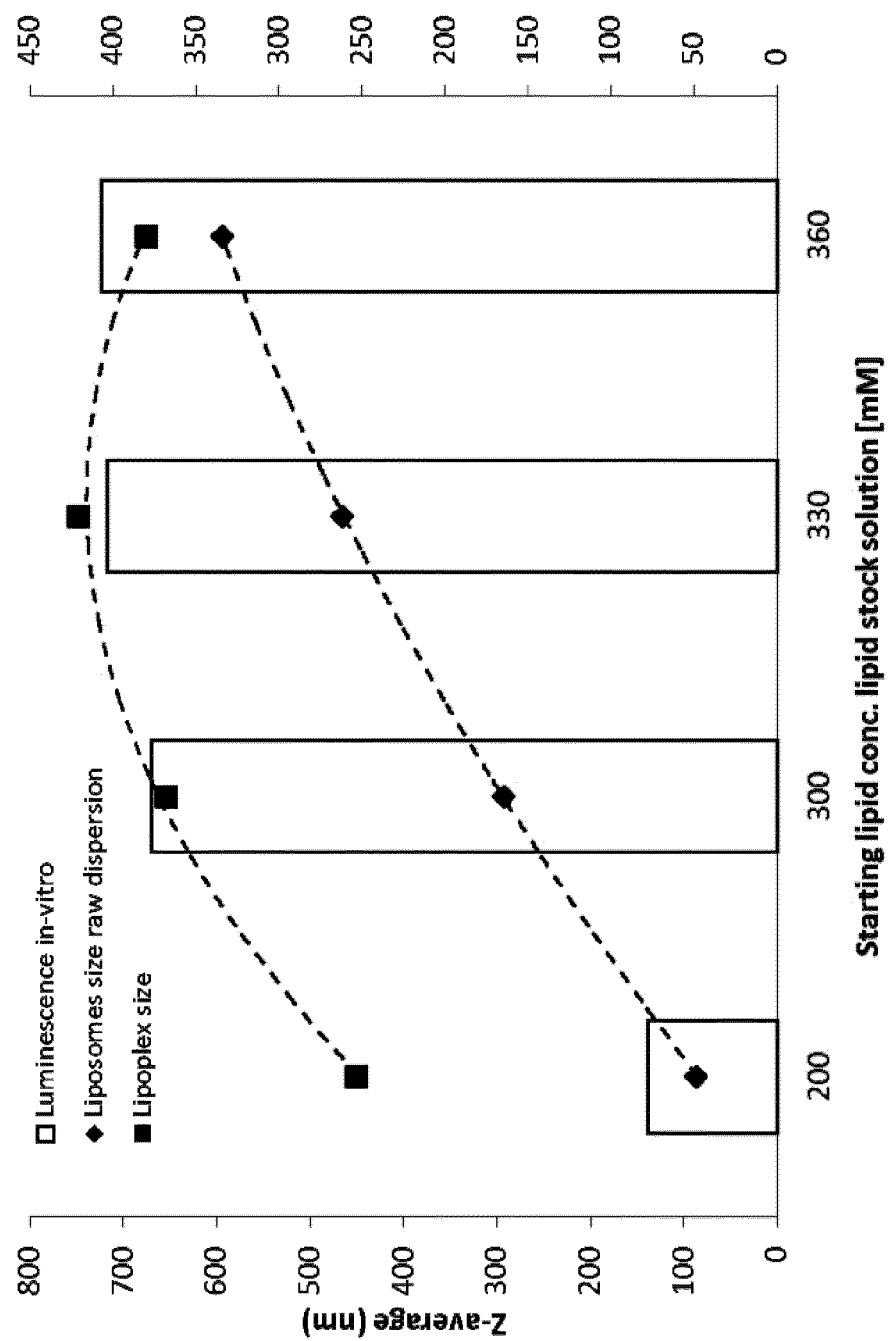
FIG. 9 shows in-vitro transfection efficiency of different RNA-lipoplex in dendritic cells. Luciferase signal increase monotonously with the liposome size.

As determined by cell culture transfection experiments (dendritic cells) with luciferase-encoding RNA lipoplexes of different sizes prepared from liposomes, different lipid stock solutions and/or different lipid concentrations as described, luciferase signals and thus biological activities increase monotonously with the lipid starting concentrations and thus with the liposome sizes used for the RNA lipoplex formation. Corresponding results are shown in FIGS. 6, 8 and 9.

In summary, RNA lipoplexes generated from higher lipid concentrations for liposome manufacturing exhibit a significantly higher activity in vitro.

Example 19: Biological Activity of RNA Lipoplexes In Vivo

As determined by cell culture transfection experiments (dendritic cells) with luciferase-encoding RNA lipoplexes prepared from liposomes of different sizes, RNA lipoplexes prepared with larger liposomes result in a significantly higher luciferase expression and corresponding biological activity.

Figure 10:
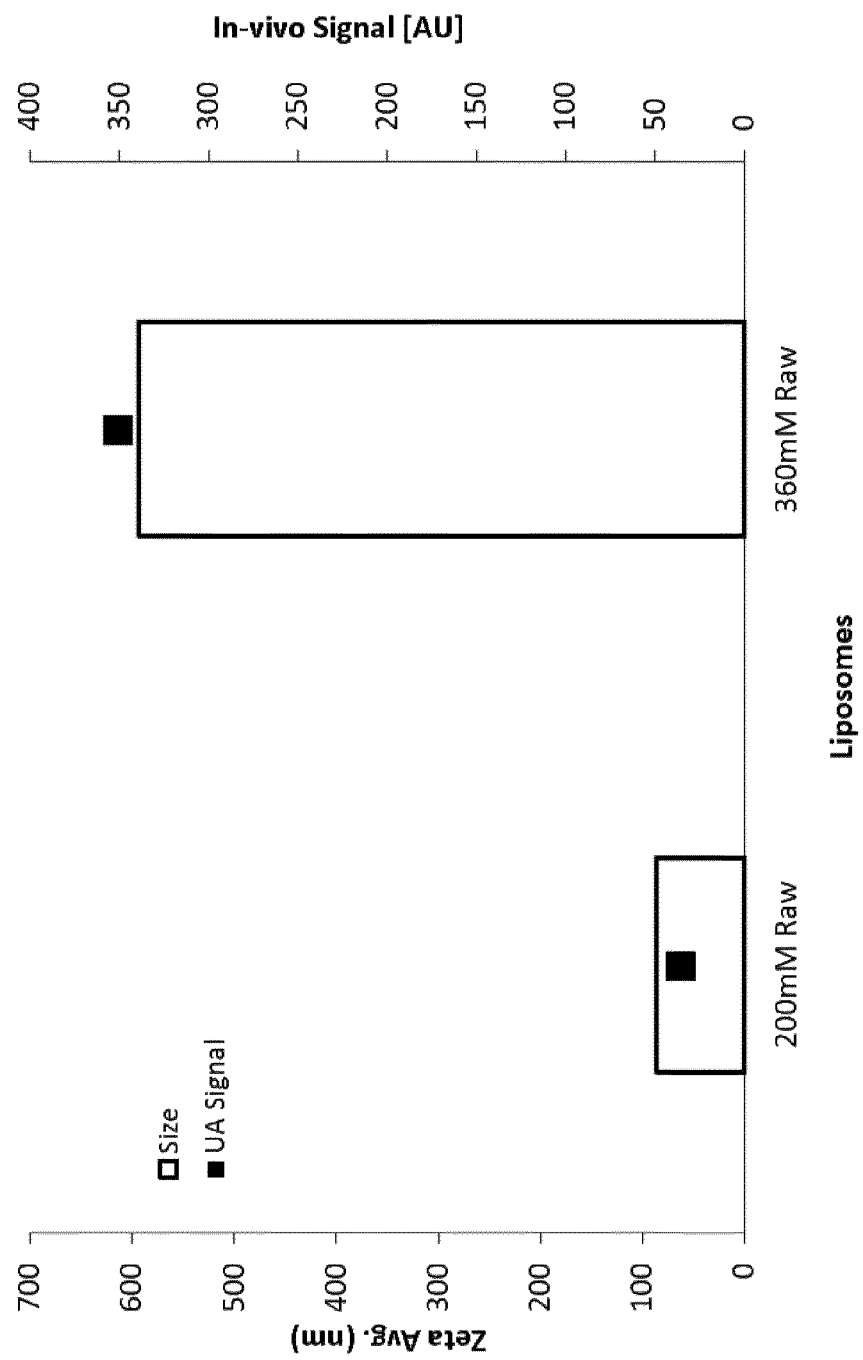
FIG. 10 shows in-vivo transfection efficiency of RNA-lipoplex formulations 6 h after application. RNA-lipoplexes were prepared with small and large liposomes (non-filtered liposomes). RNA-lipoplexes prepared with larger liposomes results in a higher luciferase expression.
Figure 11:
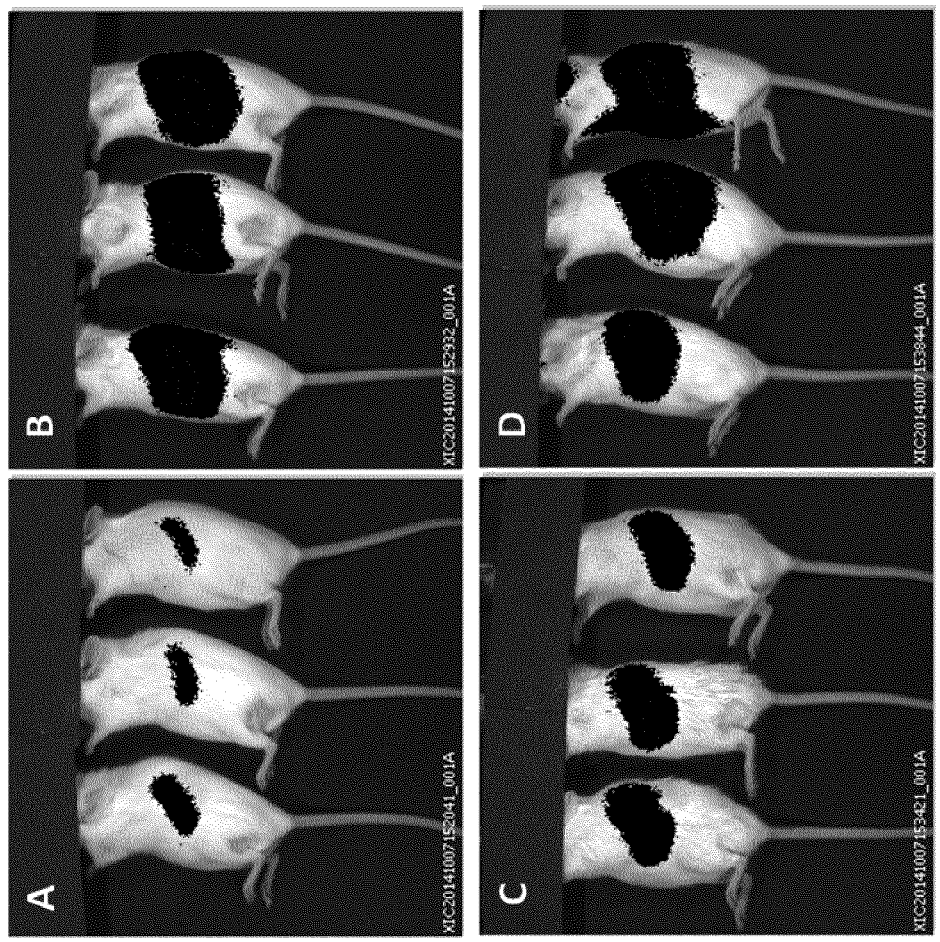
FIG. 11 shows in-vivo imaging of RNA-lipoplexes 6 h after application. RNA-lipoplexes were prepared with small and large liposomes. A) RNA-lipoplex prepared with small liposomes from a raw colloid. B) RNA-lipoplex prepared with larger liposomes from a raw colloid. C) RNA-lipoplex prepared with small filtered liposomes. D) RNA-lipoplex prepared with large filtered liposomes. Higher bioluminescence signals obtained with the RNA-lipoplex prepared with larger liposomes.

A non-limiting example of this test series is shown in FIGS. 10 and 11. RNA lipoplexes prepared with larger liposomes from a 360 mM raw colloid lead to a significantly in vivo expression signal than small RNA lipoplexes from a 200 mM raw colloid.

Example 20: Automated Manufacturing of RNA Lipoplexes

Figure 12:
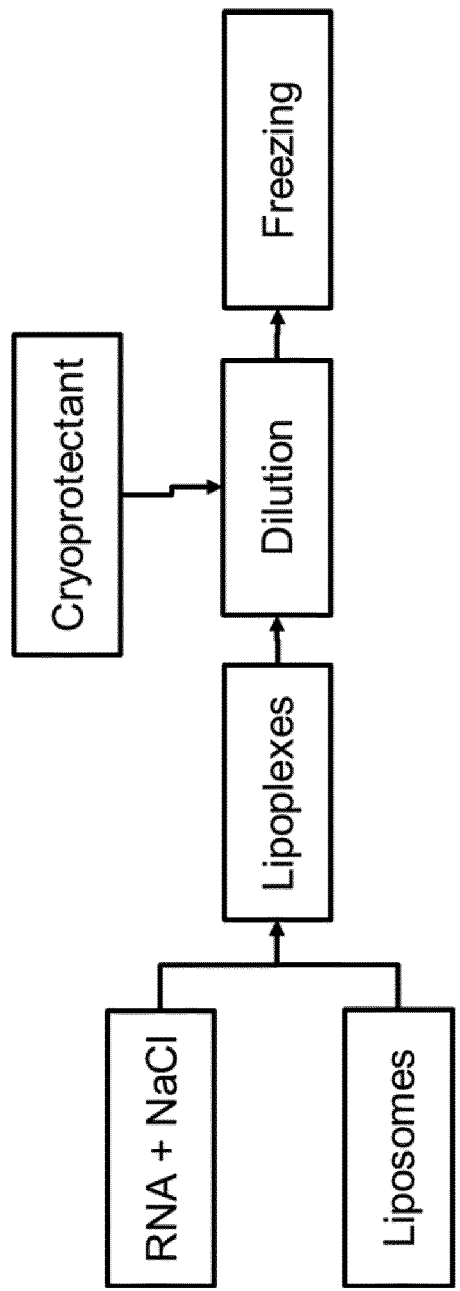
FIG. 12 shows the general procedure for automated batch manufacturing of RNA lipoplexes.

For automated batch manufacturing of RNA lipoplexes, a generally applicable procedure has been developed which is shown in FIG. 12. All steps are performed using a pre-sterilized single use fluid path allowing for safe aseptic handling of the materials. First, the concentration of the RNA is adjusted to the liposome concentration and NaCl is added for condensation of the RNA. Thereby, the RNA solution is adjusted to an RNA concentration allowing for mixing of identical volumes of RNA and liposomes. Both the RNA and the liposome solution are transferred into large-volume syringes and both syringes are mounted onto a single syringe pump simultaneous driving the two pistons of the syringes. After RNA lipoplex formation, a cryoprotectant solution is added and the final concentration of the drug product is adjusted. After filling of the drug product in to glass bottles, the drug product is frozen as a concentrate for long term storage.

A critical quality attribute of RNA lipoplexes is the charge ratio adjusted by the mixing ratio between RNA and liposomes. An automatable and scalable industrial manufacturing process for RNA lipoplexes allowing for efficient control of the mixing ratio was developed. In a process for manufacturing of small scales (≤10 liters), control of the mixing of identical volumes of two aqueous solutions containing liposomes and RNA is achieved by using a single perfusor pump simultaneously driving two large-volume syringes filled with RNA or liposomes. For equivalent pumping of larger volumes (≥10 liters) pumping systems as pressurized vessels, membrane pumps, gear pumps, magnetic levitation pumps, or peristaltic pumps are used in combination with flow rate sensors with feedback-loop for online-control and real-time adjustment of the flow rate. For automated RNA lipoplex manufacturing a static mixing element ensuring efficient mixing of the aqueous solutions containing RNA and liposomes is required. Commercially available microfluidic mixing elements containing serpentines and embedded structures for enhancement of mixing, as well as prototype mixing elements with comparable architecture were found to block during manufacturing. Therefore these mixing elements are not suited for automated manufacturing of RNA lipoplexes. Y-type and T-type mixing elements with diameters between 1.2 and 50.0 mm were found to be suited for automated manufacturing of RNA lipoplexes.

Method:

RNA lipoplexes were prepared by using different mixing elements (table 1). During manufacturing of the lipoplexes, the mixing elements were observed by the operator and deposition of material or clogging was documented.

Results:

With the commercially available microfluidic chip (NanoAssemblr™, Precision Nanosystems, Vancouver, Canada), clogging was observed after preparation of 3 mL of RNA lipoplexes. Similar observations were made during testing of further prototype microfluidic mixing elements (Table 5). Whereas for all (micro) fluidic mixing elements comprising architectures comparable to the commercially available mixing element deposition and particularly blocking of the elements could be observed, there were no observations when using Y-type or T-type mixing elements. Besides the described y-type mixing element with a diameter of 2.4 mm, mixing elements with larger diameters have been tested. As no limitation for the diameter of the Y-type mixing element were found, the described method is considered to be suited for preparation of RNA lipoplexes at diameters of up to 50 mm of the y-type mixing elements.

TABLE 5

Clogging of microfluidic chip.

| Mixing element | Channel with (μm) | Particle size RNA lipoplexes (nm) | Deposits or clogging |
|---|---|---|---|
| NanoAssemblr™ | ca. 0.2 mm | 374 | Clogging after 3 mL |
| Prototype 1 | ca. 0.3 mm | 337 | Clogging after 34 mL |
| Prototype 2 | ca. 0.3 mm | 372 | Clogging after 88 mL |
| Prototype 3 | ca. 0.4 mm | 336 | Deposition, no clogging until 120 mL |
| Prototype 4 | ca. 1.0 mm | 326 | Deposition, no clogging until 180 mL |
| Y-type mixing element | 2.4 mm | 348 | No deposition, no clogging until 200 mL |

When using Y-type or T-type mixing elements, a minimum flow rate is required in order to achieve sufficient mixing. RNA lipoplex preparation can be performed by mixing two aqueous solutions containing RNA and liposomes by using a Y-type or T-type mixing element with an inner diameter of 1.6 to 50 mm. The Reynolds number resulting from the flow rate for mixing should not be lower than ca. 300 in order to ensure efficient mixing. The flow rate to diameter of the mixing element ratio should not be lower than ca. 150 in order to ensure efficient mixing. Reynolds numbers up to about 2100 were experimentally tested and found to be suited for automated manufacturing. The data support that also higher flow rates are feasible. This is derived from the fact, that at the Reynolds number of 2100 the conditions were already in turbulent mode and therefore at even higher flow rates similar mixing conditions are to be expected.

Figure 13:
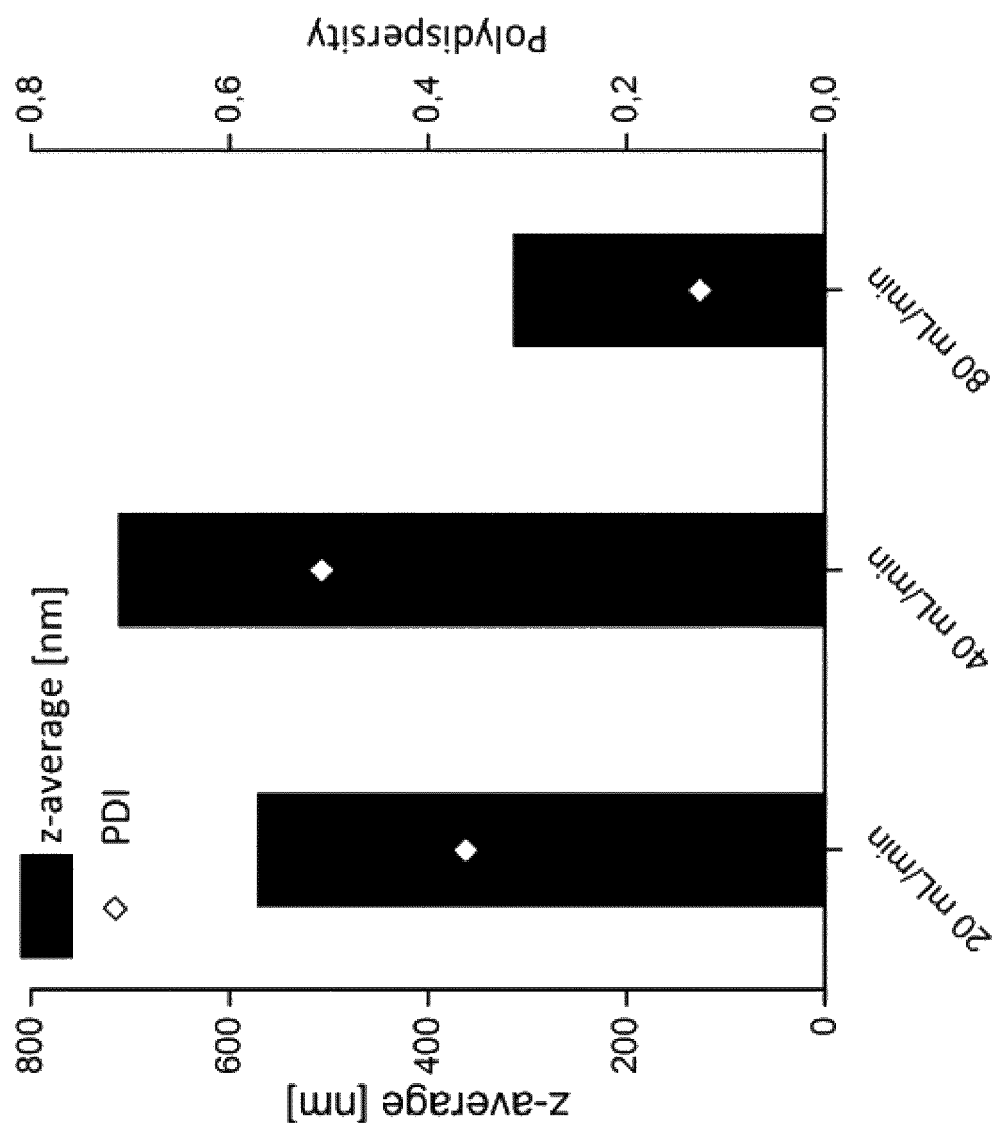
FIG. 13 shows Z-average and polydispersity of RNA lipoplexes being prepared using a Y-type mixing element with an inner diameter of 3.2 mm at different flow rates.

Method:

RNA lipoplexes were prepared by pumping the RNA solution and the liposome solution by using a single perfusor pump. RNA lipoplex formation was performed with representative Y-type mixing elements comprising an inner diameter of 2.4 and 3.2 mm. Particle sizes and polydispersity of RNA lipolexes were analyzed by photon correlation spectroscopy (PCS) measurements. Reynolds numbers resulting from the investigated combination of flow rate and diameter of the mixing elements were theoretically calculated using equation (FIG. 13). The flow rate to diameter of the mixing element ratio was calculated by dividing the flow rate ($cm^3$/min) by the diameter of the mixing element (cm). The factor is given as a dimensionless number.

Figure 14:
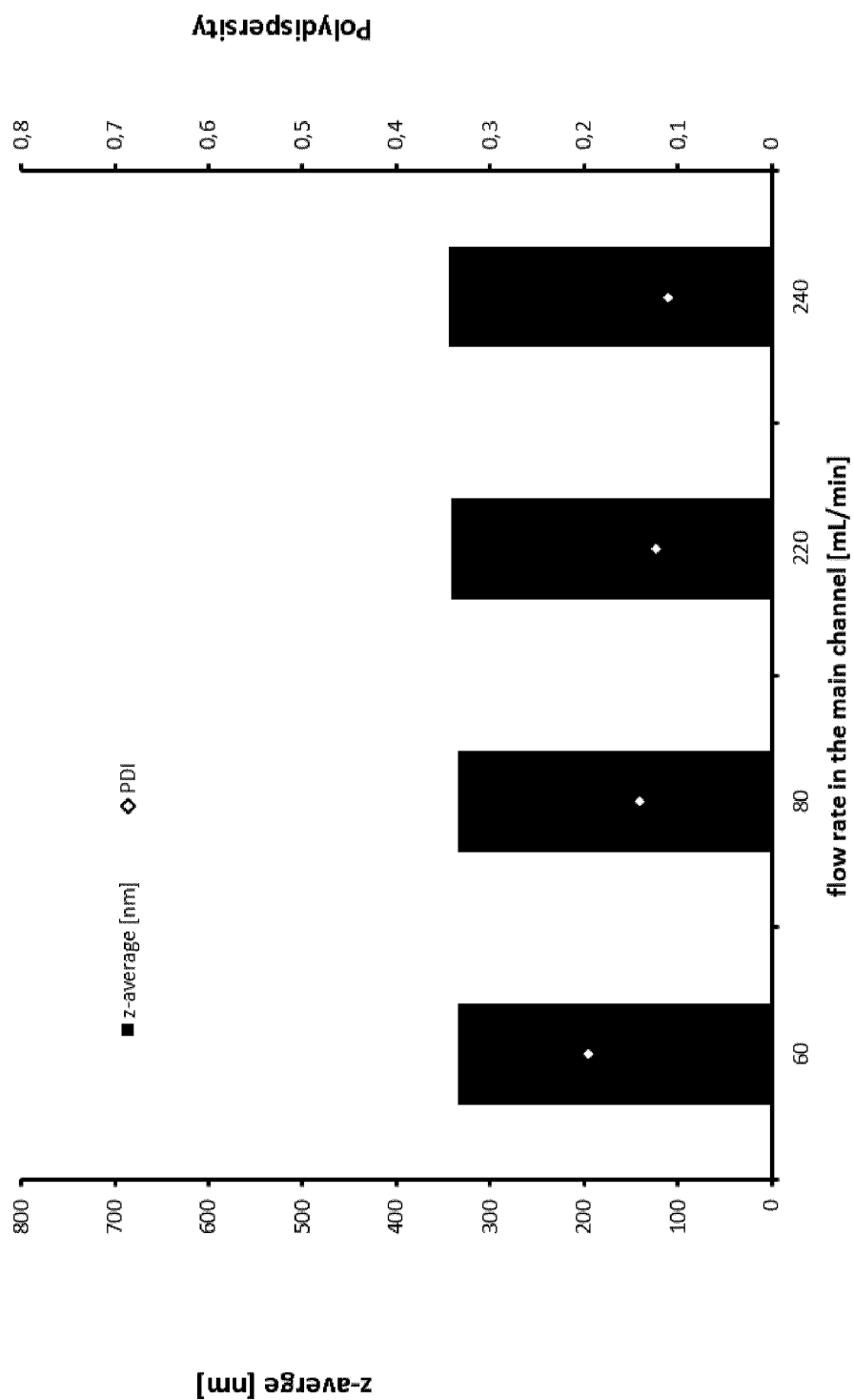
FIG. 14: shows Z-average and polydispersity of RNA lipoplexes being prepared using a Y-type mixing element with an inner diameter of 2.4 mm at different flow rates.

Results:

When manufacturing RNA lipoplexes with flow rate and mixing element combinations resulting in theoretically calculated Reynolds numbers below ca. 300, RNA lipoplexes with increased particle size and polydispersity are formed (FIG. 13 and Table 6). In order to ensure reproducible formation of RNA lipoplexes with the desired particle characteristics, the theoretically Reynolds number should be min. ca. 300 (FIGS. 13 and 14 and table 6) and the flow rate to diameter of the mixing element ratio should be min. ca. 150. The 2.4 mm mixing element was found to enable efficient and reproducible mixing of RNA and liposomes in a wide range of flow rates (60 to 240 mL/min). As no upper limit was found during these studies, no upper limitation of the Reynolds number or the flow rate to diameter of the mixing element ratio is expected.

TABLE 6

Calculated Reynolds numbers and ratio of folw rate to diameter of mixing element.

| Diameter of mixing element (mm) | Flow rate (mL/min) | Calculated Reynolds number[a] | Ratio flow rate to diameter mixing element[b] |
|---|---|---|---|
| 3.2 | 20 | 132 | 63 |
| 3.2 | 40 | 265 | 125 |
| 3.2 | 80 | 530 | 250 |
| 2.4 | 60 | 531 | 250 |
| 2.4 | 80 | 707 | 333 |
| 2.4 | 220 | 1945 | 917 |
| 2.4 | 240 | 2122 | 1000 |

[a]Viscosity (0.001 Pa s) and density (1000 kg/$m^3$) of water was used for calculation of the Reynolds Number.
[b]The factor was calculated by dividing the flow rate ($cm^3$/min) by the diameter of the mixing element (cm). The factor is given as a dimensionless number.

Example 21: Influence of RNA Concentrations

RNA lipoplexes were prepared with the y-type mixing element with representative dimensions (2.4 mm). In order to identify the concentration range in which RNA lipoplexes can be prepared in the current setup, the RNA concentration was systematically varied from 0.05 mg/mL to 0.5 mg/mL. In order to investigate the stability of the formed lipoplexes, the final formulation was adjusted to 0.05 mg/mL RNA, 22% sucrose and 20 mM NaCl and the formulations were frozen three times.

Figure 15:
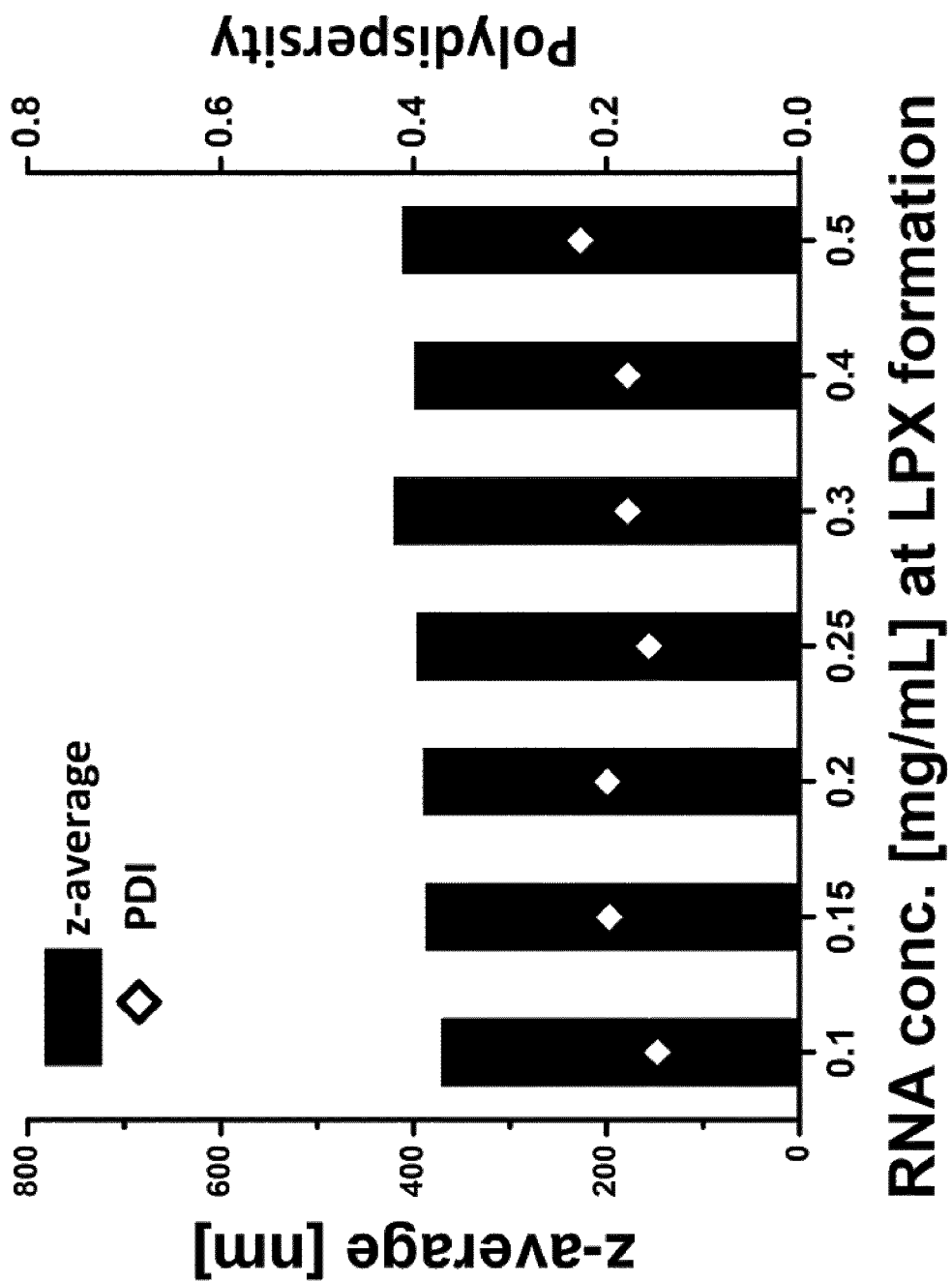
FIG. 15 shows the correlation of particle size and RNA conc. at lipoplex formation. PCS measurement was performed prior to freezing.
Figure 16:
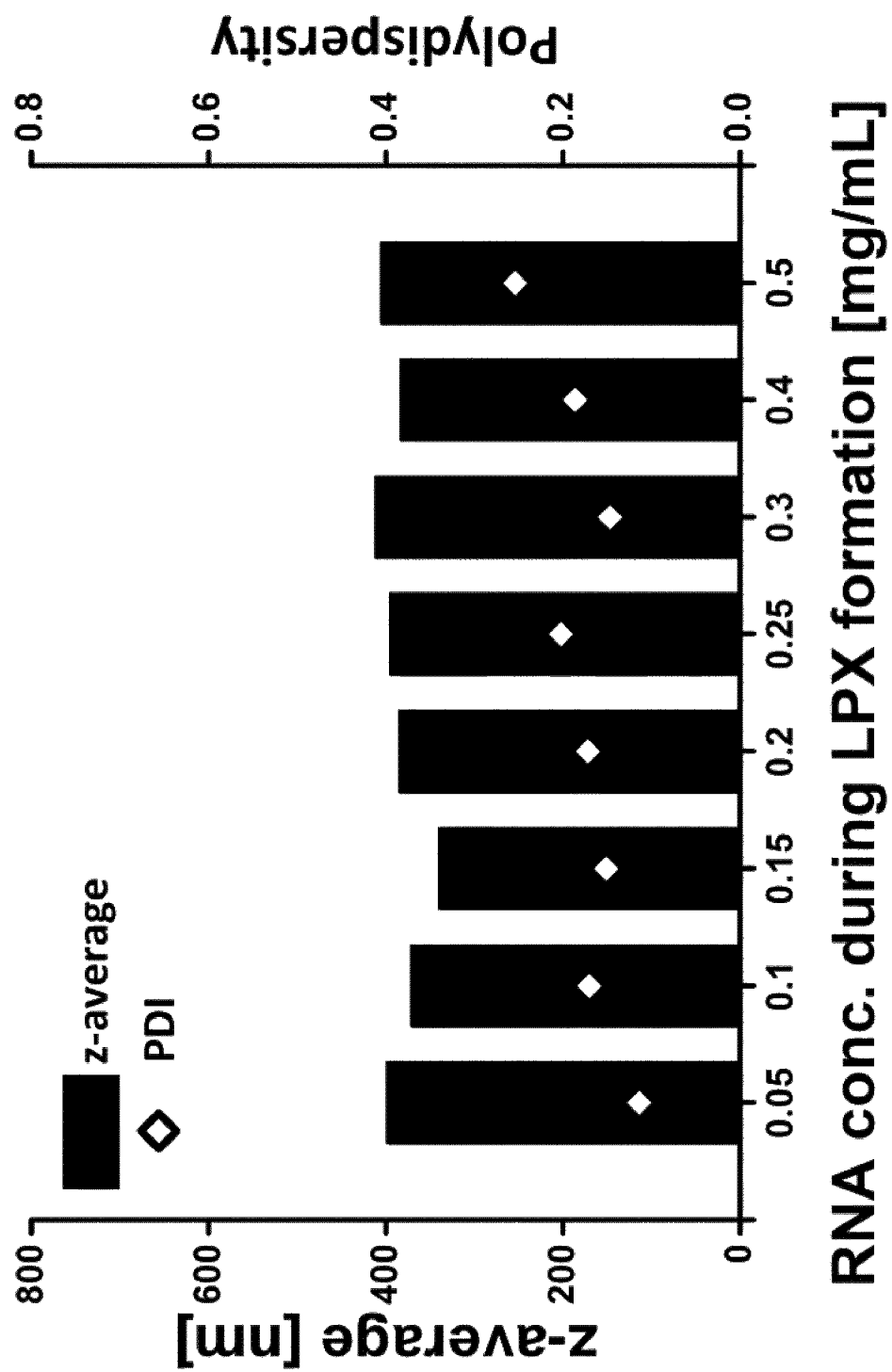
FIG. 16 shows the correlation of particle characteristics and RNA conc. at lipoplex formation after three freeze thaw cycles.

RNA lipoplex formation at RNA concentrations between 0.1 and 0.5 mg/mL during RNA lipoplex formation results in comparable particle characteristics (FIG. 15). The particle characteristics of such particles are also preserved upon three times freezing indicating a very robust manufacturing process with respect to variations of the RNA concentration (FIG. 16). As there are no hints for a limitation of the RNA concentration during the RNA lipoplex preparation, the described setup is considered as suited for RNA lipoplex preparation at a RNA concentration of up to 5 mg/mL.

The described process for automated manufacturing of RNA lipoplexes allows for reproducible preparation of stable RNA lipoplexes with different charge ratios.

Method:

In order to prove the robustness of the semi-automated preparation of RNA lipoplexes with respect to the charge ration, this parameter was systematically varied from 1.0:2.0 to 2.1:2.0 and from 2.0:1.0 to 5.0:1.0. Particle sizes and polydispersity of RNA lipoplexes were analyzed by photon correlation spectroscopy (PCS) measurements.

Figure 17:
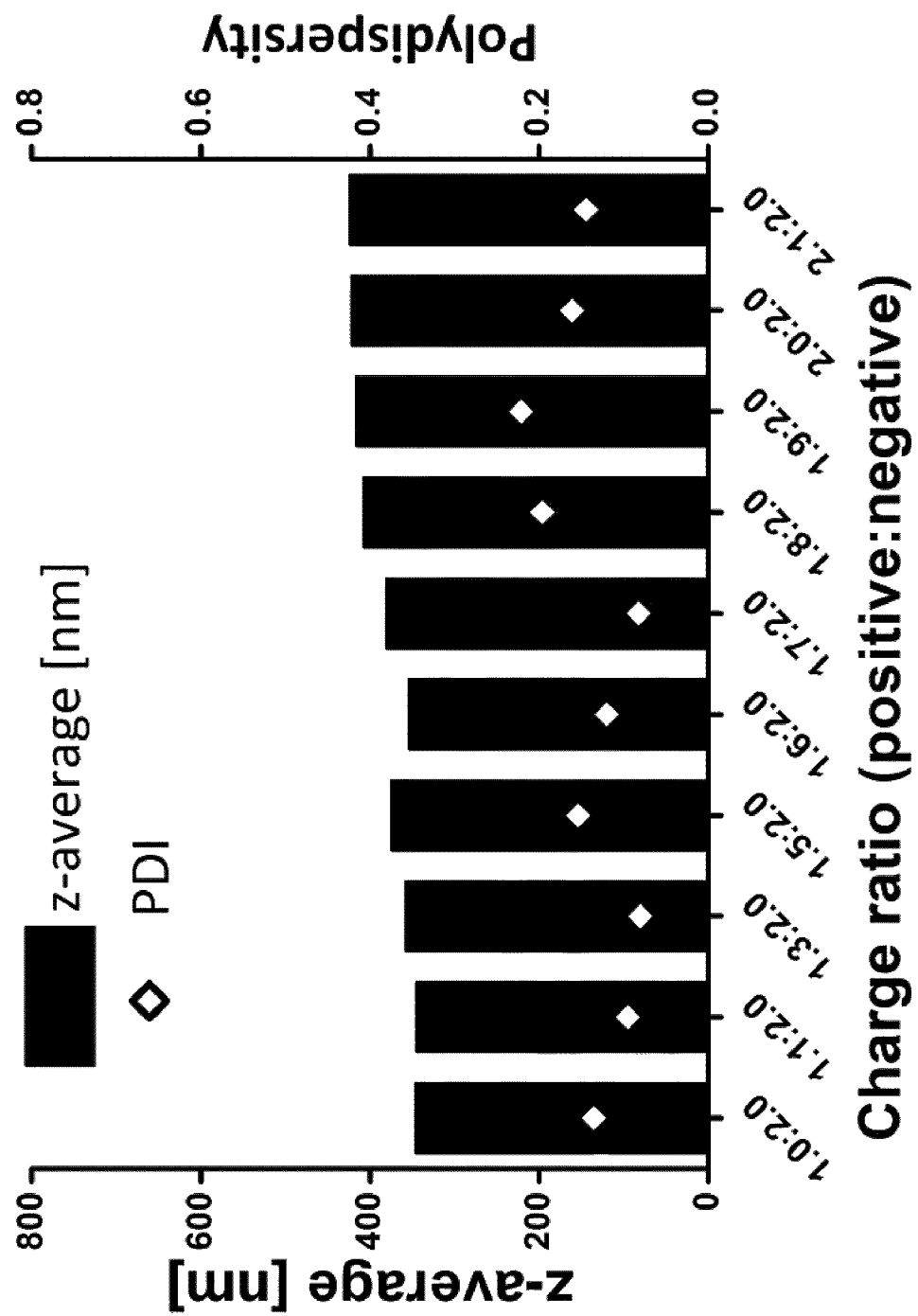
FIG. 17 shows the correlation of particle characteristics and charge ratio (positive:negative) in the range from 1.0:2.0 to 2.1:2.0.
Figure 18:
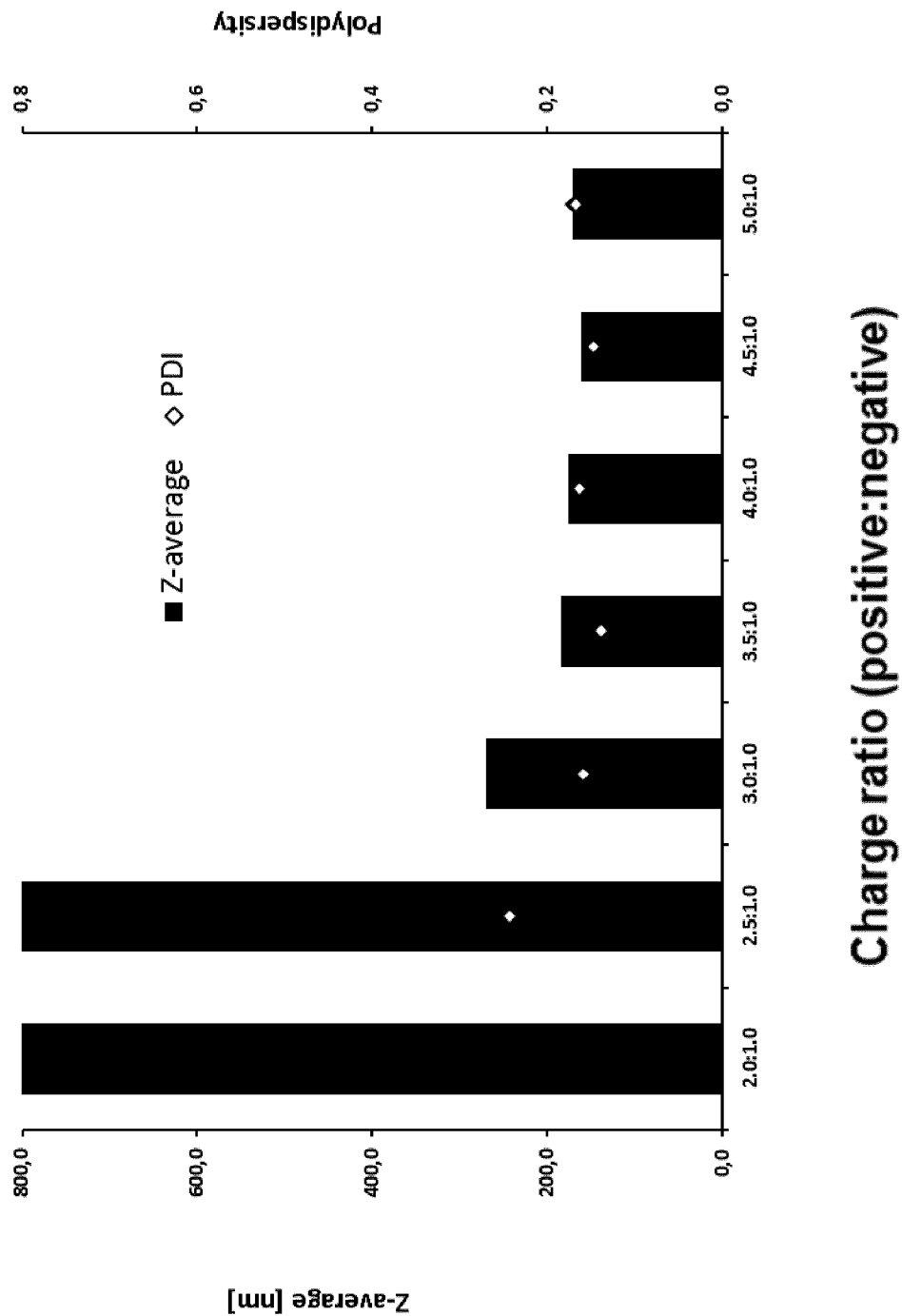
FIG. 18 shows the correlation of particle characteristics and charge ratio (positive:negative) in the range from 2.0:1.0 to 5.0:1.0.

Results:

No impact of variation of the charge ratio on RNA lipolexes size and polydispersity was found between a charge ratio of 1.0:2.0 and 2.1:2.0 (FIG. 17). Therefore, the range between 1.0:2.0 and 2.1:2.0 is considered to result in RNA lipoplex preparations with equivalent quality. Additionally, stable particles with defined size and polydispersity were formed between a charge ratio of 3.0:1.0 and 5.0:1.0 (FIG. 18).

Example 22: Salt Concentration During RNA Lipoplex Formation

For automated manufacturing of RNA lipoplexes comprising high biological activity, controlled ionic conditions during RNA lipoplex formation are required. In order to ensure biologic activity, RNA lipoplex formation has to be performed in the presence of 45 to 300 mM NaCl. Other ionic compounds as e. g. EDTA, HEPES, etc. contribute to the ionic strength and may reduce the required minimum concentration of NaCl.

Method:

RNA lipoplexes were automatically prepared at different concentrations of NaCl during RNA lipoplex formation. Particle sizes and polydispersity of RNA lipoplexes were analyzed by photon correlation spectroscopy (PCS) measurements. Additionally, the bioactivity of the lipoplexes was investigated by measuring the luciferase signal in vitro.

Figure 19:
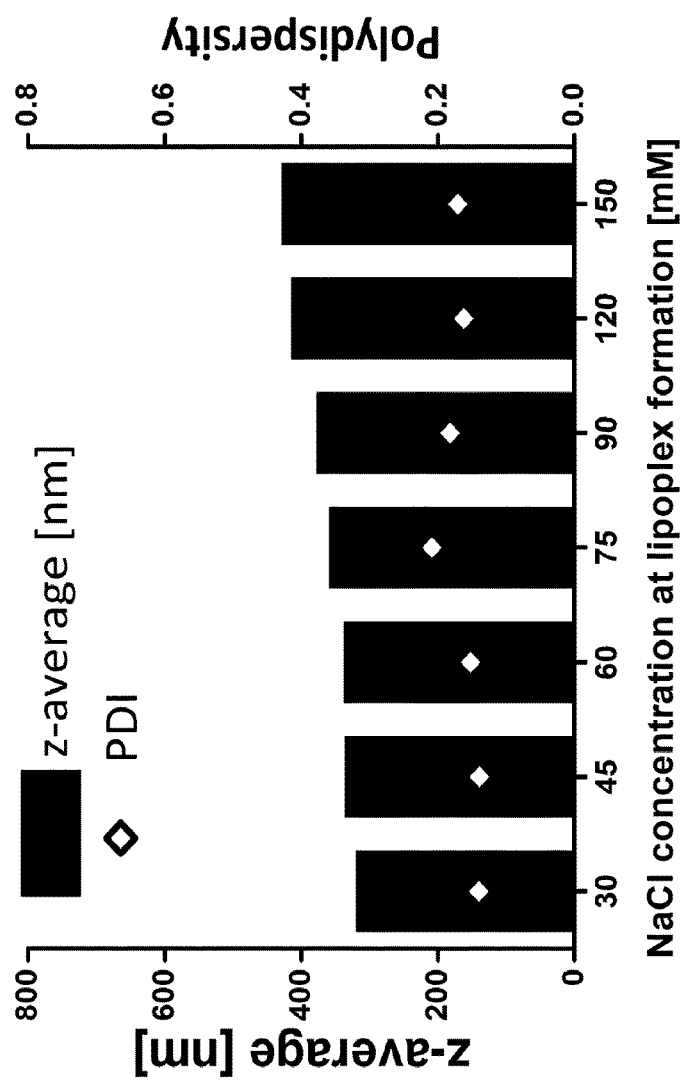
FIG. 19 shows the correlation of particle characteristics and NaCl concentration at lipoplex formation.
Figure 20:
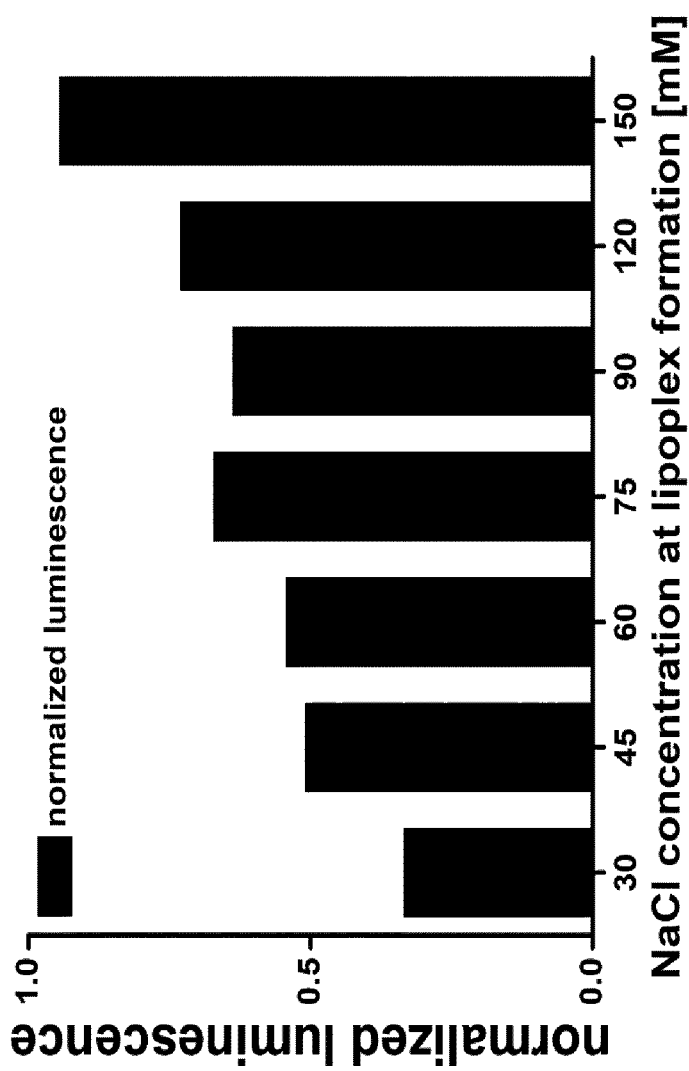
FIG. 20 shows the correlation of bioactivity and NaCl concentration at lipoplex formation.

Results:

Particle characteristics could be controlled by adjustment of the ionic strength. Increasing salt concentrations during manufacturing induced slightly increasing particle size (FIG. 19). The salt concentration was found to have an impact on the bioactivity. Increasing salt concentration during manufacturing induced increasing bioactivity (FIG. 20). Therefore the NaCl concentration during RNA lipoplex formation should not be lower than 45 mM NaCl.

Example 23

Stabilization of RNA lipoplexes

Buffer systems as HEPES, acetic acid/sodium acetate, and sodium phosphate for stabilization of RNA in lipoplexes in the pH range from pH 5.5 to 6.7 can be used for stabilization of RNA in RNA lipoplexes both in the presence and the absence of a cryoprotectant. The sodium carbonate system was found to not result in comparable stabilization efficacy.

Method:

For investigation of the optimum pH range and testing of the suitability of different buffering agents covering different pH-ranges (HEPES pH 6.8-8.2, acetic acid/sodium acetate pH 3.7-5.6, sodium phosphate pH 5.8-8.0, and sodium carbonate pH 6.2-8.6). RNA lipoplexes are initially incubated under stress conditions (40° C.) in the absence of cryoprotectant. RNA integrity was analyzed by capillary electrophoresis over 21 days. In order to investigate the optimum pH range in the presence of an exemplary cryoprotectant, RNA lipoplexes were incubated in the presence of HEPES and sucrose at 40° C. and RNA integrity was analyzed for 21 days.

Figure 21:
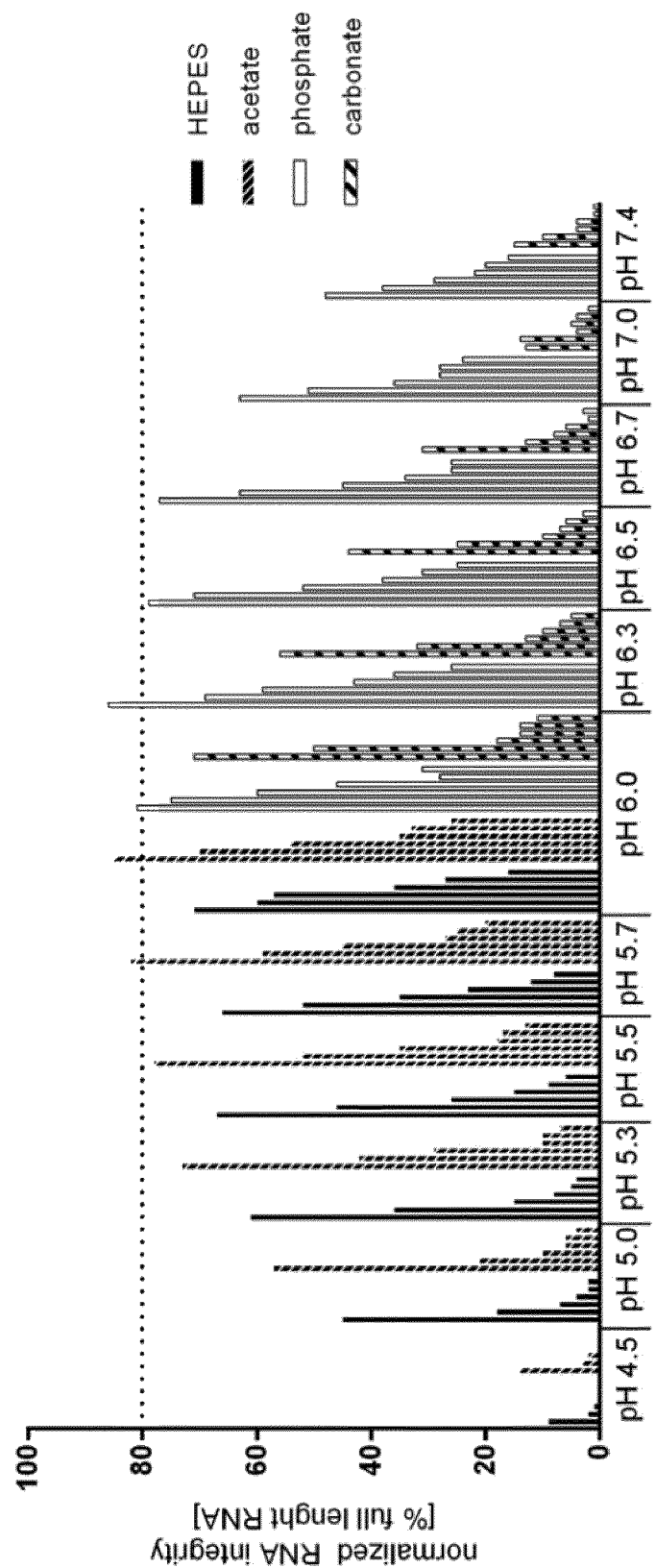
FIG. 21 shows measurements of RNA integrity in RNA $_{(LIP)}$ compositions without cryoprotectant using different buffer substances (HEPES; Na-acetate; Na-phosphate; Na-carbonate) at several pH-values after accelerated storage at +40° C. The different bars indicate increasing storage periods from left (3 days) to right (21 days).
Figure 22:
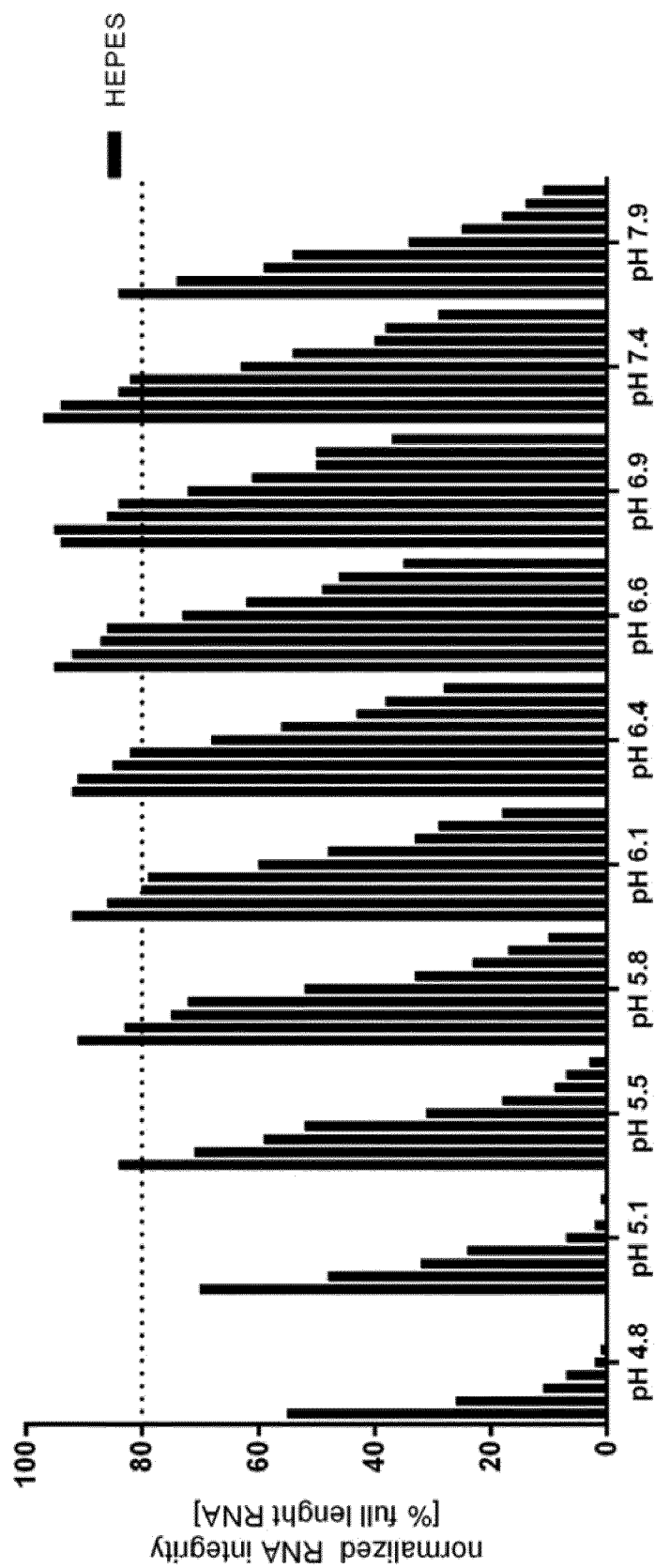
FIG. 22 shows measurements of RNA integrity in RNA lipoplex formulations with sucrose as cryoprotectant using HEPES as buffer substance at several pH-values after accelerated storage at +40° C. The different bars indicate increasing storage periods from left (1 day) to right (21 days).

Results:

Whereas for the buffering systems HEPES, acetic acid/sodium acetate, and sodium phosphate comparable results were obtained, the carbonate system did not result in comparable stabilization of the RNA (FIG. 21). The RNA integrity depends on the pH value of the formulation. The optimum pH range was identified to be in the range between pH 5.5, and 7.4. In the presence of the exemplary cryoprotectant sucrose, a pH range of pH 5.5 to 8.0 was identified resulting in the best stabilization of the RNA (FIG. 22).

Bivalent metal ions can arise from the RNA synthesis process, formulation excipients or glass containers and can affect the RNA stability. EDTA disodium salt forms stable water-soluble complexes with alkaline earth and heavy-metal ions. EDTA disodium salt contributes to the concentration of ions present during RNA lipoplex formation and thereby reduces the concentration of NaCl required for preparation of bioactive RNA lipoplexes. RNA lipoplex formation in the presence of EDTA (0 to 20 mM) is possible with the described process.

Method:

RNA lipoplexes were formed in the presence of increasing concentrations of EDTA (up to 18 mM) and upon dilution incubated at reduced EDTA content (0.1 mM to 5.4 mM) at 40° C. RNA integrity was analyzed as a key physicochemical parameter over 21 days.

Figure 23:
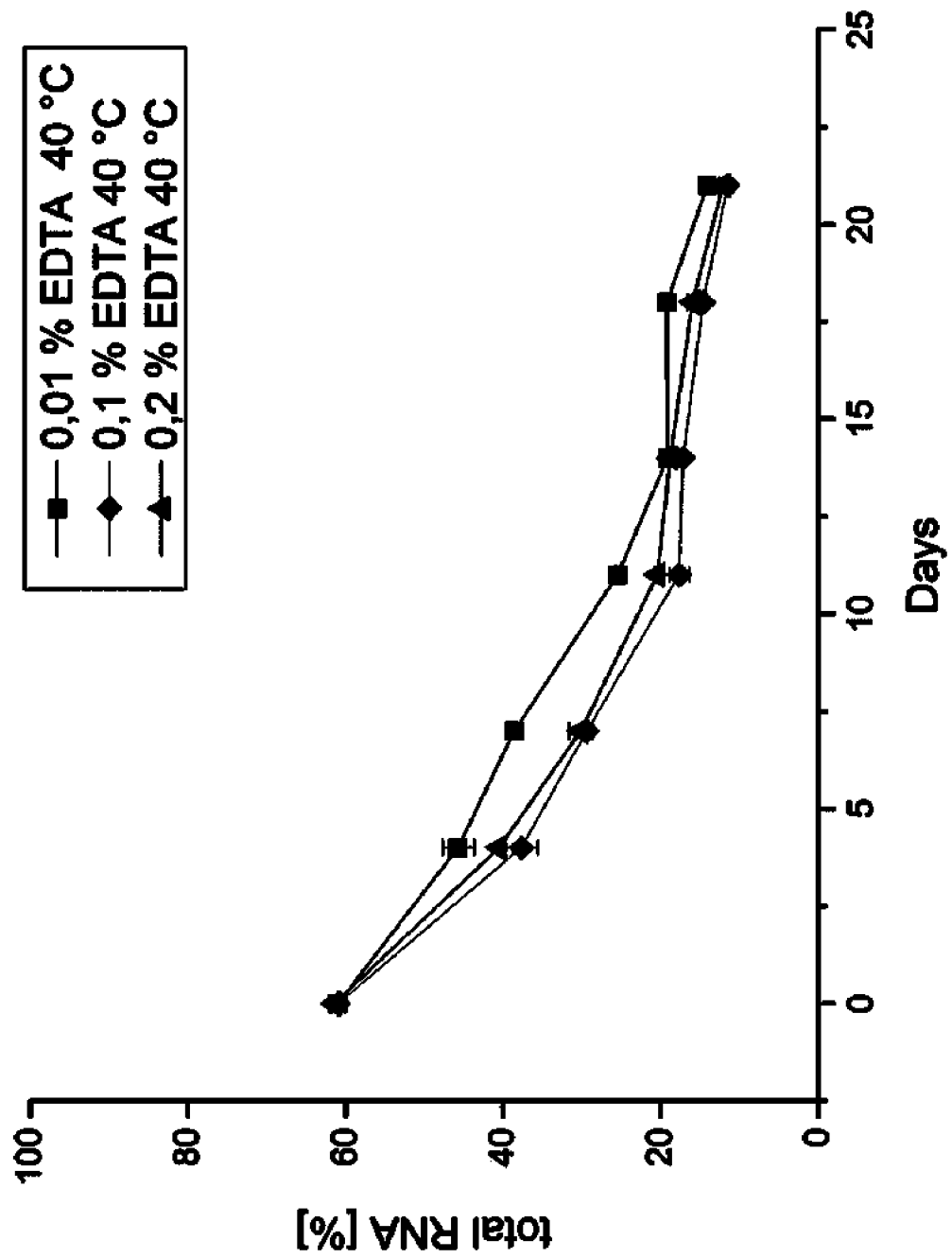
FIG. 23 shows the integrity of RNA in lipoplexes stored at 40° C. with different content of EDTA.

Results:

The formation of RNA lipoplexes in the presence of high concentrations of EDTA (up to 18 mM) was found to result in equivalent particle characteristics as the preparation in the presence of lower concentrations. No significant difference was found between the different groups containing between 0.01% (w:v) (0.1 mM) and 0.2% (w:v) (5.4 mM) EDTA (FIG. 23) during storage. As EDTA disodium salt contributes to the concentration of ions present during RNA lipoplex formation and can work as a scavenger for bivalent metal ions potentially decreasing RNA integrity, the presence of EDTA concentrations up to 20 mM during RNA lipoplex formation are considered advantageous.

Example 24: Optimization of NaCl and Cryoprotectant Content

Figure 24:
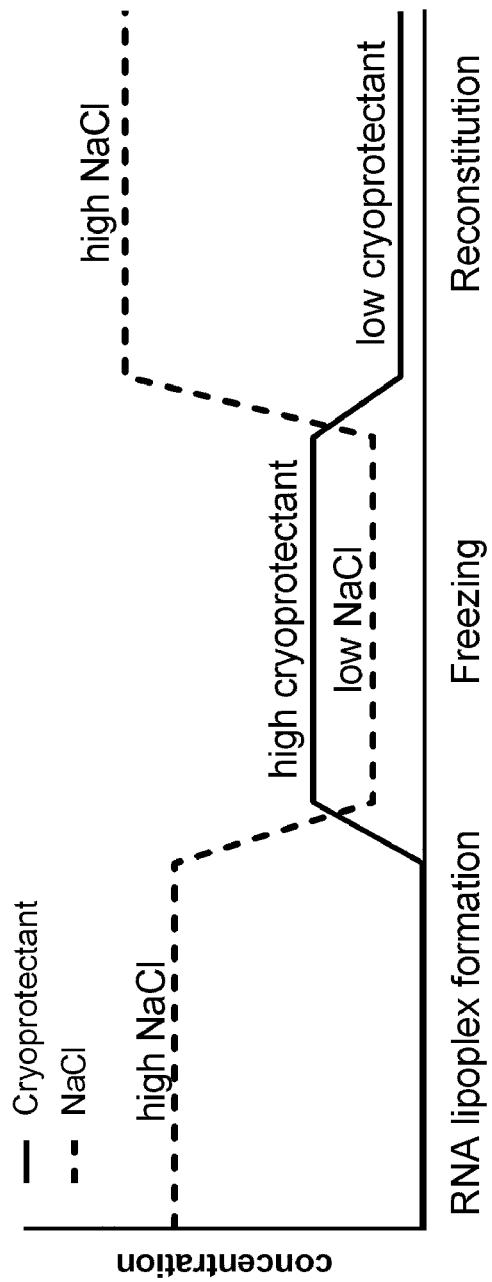
FIG. 24 is a general diagram indicating that the concentration of NaCl and cryoprotectant was optimized in each step.

The adjusted ionic conditions need to be adjusted during RNA lipoplex manufacturing, long-term storage, and application to the patient (FIG. 24). Concentration of NaCl can be 45 to 300 mM during the formation of RNA lipoplexes; 10 to 50 mM during long-term storage of RNA lipoplexes in the frozen state; and 80 to 150 mM after thawing and dilution with saline.

For each NaCl concentration ≤70 mM, a respective content of cryoprotectant was found which should not be deceeded in order to ensure stabilization of particle characteristics upon multiple freezing. As cryoprotectant can be used mono- and bimolecular sugars as glucose, sucrose, mannitol, trehalose, sorbitol, triols as glycerine, and mixtures thereof in concentrations between 12.5 and 35.0% (w:v). The stabilization efficacy of sorbitol is lower when being compared with the latter compounds and arginine is not efficiently stabilizing RNA lipoplexes during freezing.

TABLE 7

Combinations of NaCl concentration and cryoprotectant content investigated after a single freezing step.

| NaCl (mM) | Cryoprotectant (% w:v) | | | |
|---|---|---|---|---|
| | 5 | 10 | 15 | 20 |
| 0 | X | X | X | X |
| 20 | X | X | X | X |
| 40 | X | X | X | X |
| 60 | X | X | X | X |

TABLE 8

Combinations of NaCl concentration and cryoprotectant content investigated after 1, 2, 3, 5 and 10 freezing steps.

| NaCl (mM) | Cryoprotectant (% w:v) | | | | | | | |
|---|---|---|---|---|---|---|---|---|
| | 10.0 | 12.5 | 15.0 | 17.5 | 20.0 | 22.5 | 25.0 | 27.5 |
| 50 | X | X | X | X | X | X | X | X |
| 70 | X | X | X | X | X | X | X | X |
| 90 | X | X | X | X | X | X | X | X |

Figure 25:
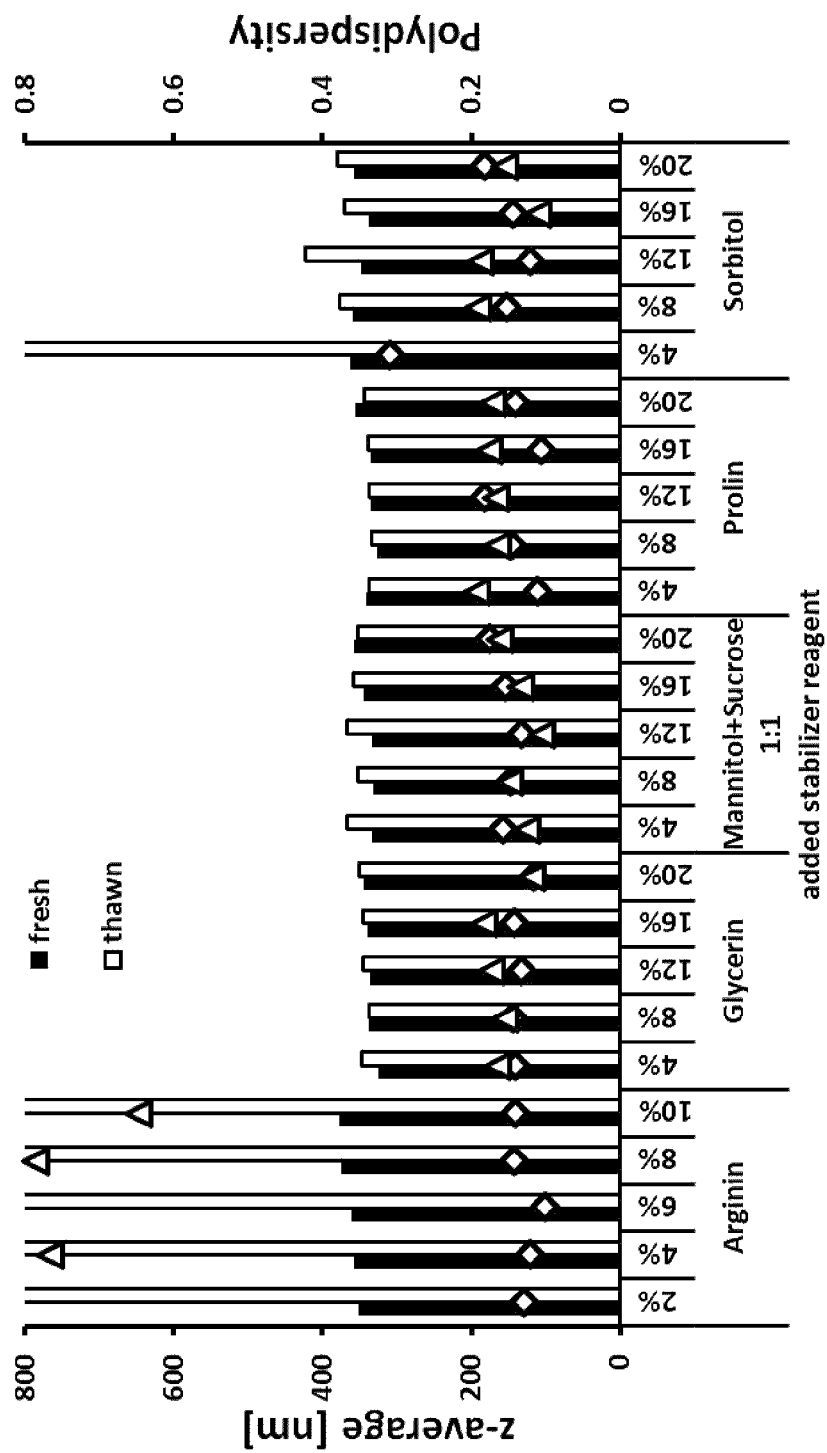
FIG. 25 shows Z-average and polydispersity of RNA lipoplexes frozen in the presence of increasing amounts of alternative cryoprotectants.
Figure 26:
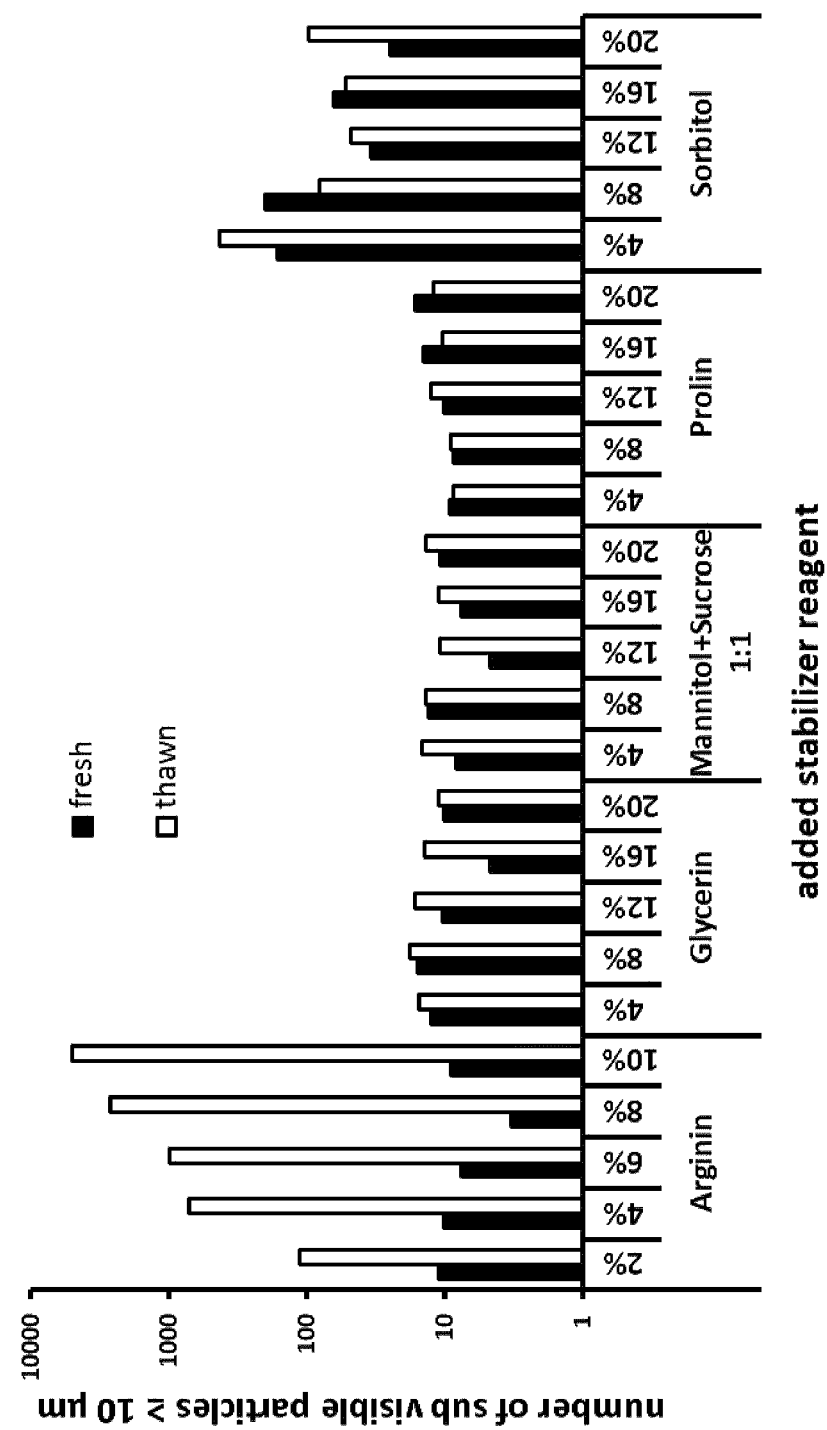
FIG. 26 shows the number of subvisible particles ≥10 μm in RNA lipoplex formulations frozen in the presence of increasing amounts of alternative cryoprotectants.

Methods:

Different compounds representative for monosaccharides (glucose and sorbitol), disaccharides (sucrose and trehalose), amino acids (arginine, prolin), triols (glycerin) as well as cryoprotectant systems containing mixtures of different sugars (mannitol and sucrose) were investigated in order to identify suited cryoprotectants (FIGS. 25 and 26). Therefore RNA lipoplexes were frozen in the presence of increasing concentration of these compounds. In order to identify minimum content of cryoprotectant at a certain concentration of NaCl, RNA lipoplexes were frozen in the presence of increasing amounts of sucrose or trehalose as representative cryoprotectants (Table 7). The samples were initially frozen a single time in order to determine the concentration range of cryoprotectant to be investigated in detail. In a third experiment, the efficacy of stabilization of the particle size was challenged by freezing of the RNA lipoplexes up to 10 times in the presence of the cryoprotectant trehalose (Table 8).

Results:

Whereas arginine clearly destabilizes the RNA lipoplexes, the other cryoprotectants are generally applicable for the stabilization of RNA lipoplexes during freezing (FIGS. 25 and 26). Glycerin, mannitol and sucrose (1:1, w:w), proline, and sorbitol can be used as cryoprotectants for RNA lipoplexes. Besides arginine, all additionally tested stabilizers appear suited indicating that a broad range of amino acids, sugars, and mixtures of such compounds are suited for stabilization of RNA lipoplexes during freezing. The stabilization efficacy of sorbitol is lower when being compared with the latter compounds.

Figure 27:
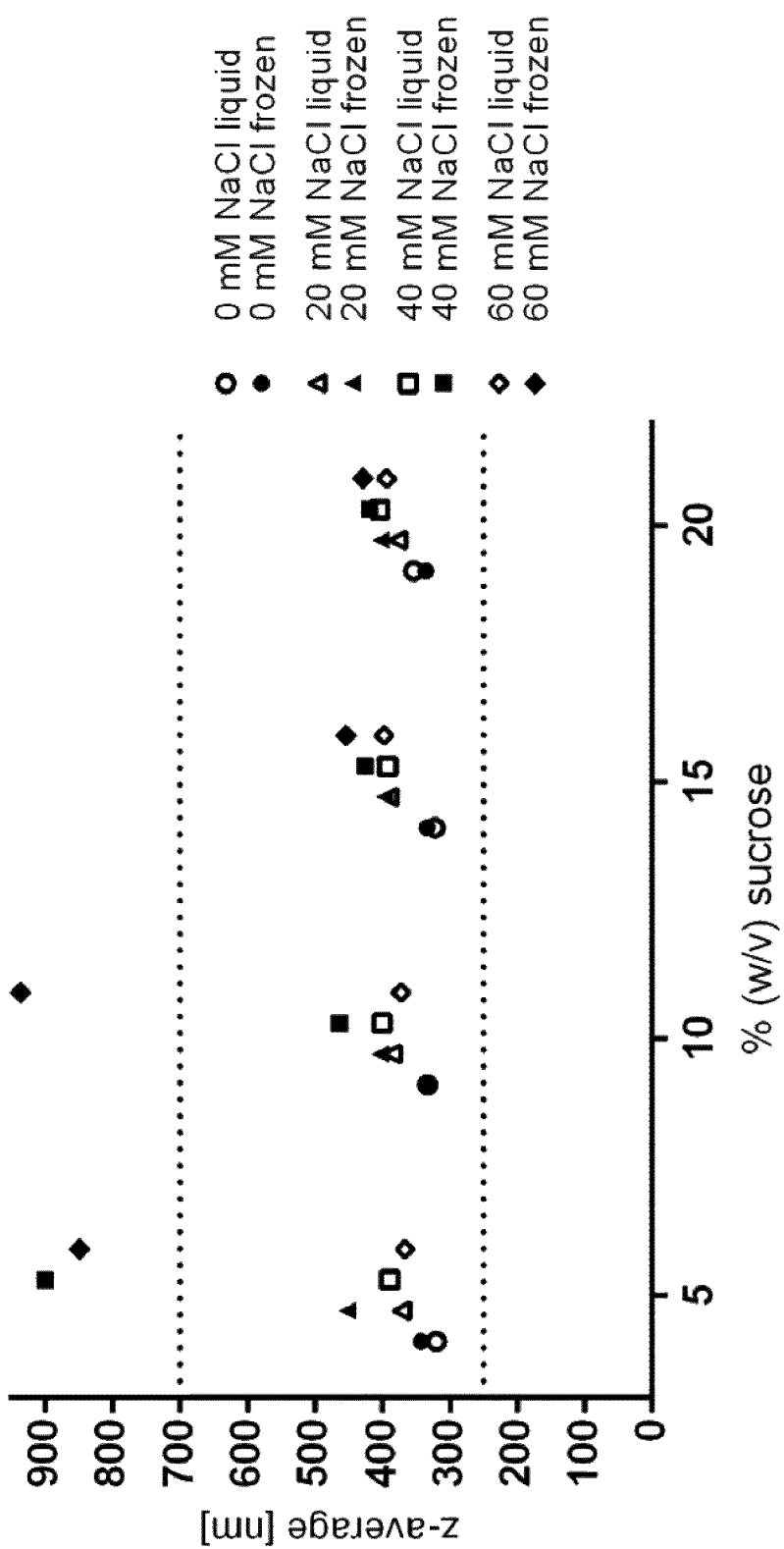
FIG. 27 shows measurements of particle size in RNA lipoplex formulations containing 5-20% w/v sucrose (X-axis) and various low NaCl concentrations before and after freezing at −30° C.
Figure 28:
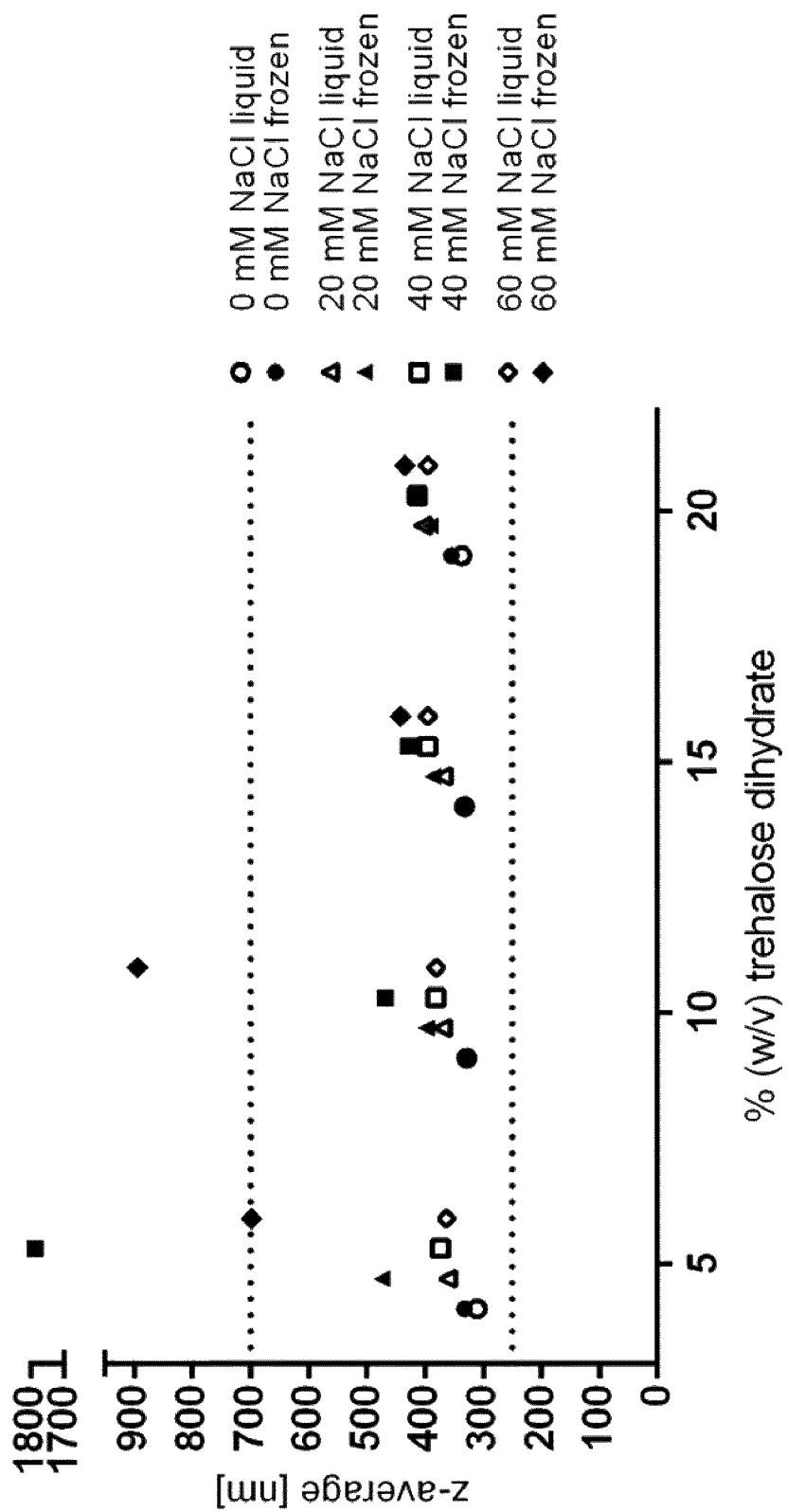
FIG. 28 shows measurements of particle size in RNA lipoplex formulations containing 5-20% w/v trehalose dihydrate (x-axis) and various low NaCl concentrations before and after freezing at −30° C.

When investigating in detail the required amount of cryoprotectant at each concentration of NaCl (Table 8), a direct correlation between the NaCl concentration and the required concentration of the cryoprotectant was found after a single freezing step (FIGS. 27 and 28). Whereas acceptable preservation of particle size was found after a single freezing step for 0 to 60 mM of NaCl at 20% (w:v) sucrose or Trehalose dihydrate, there was insufficient stabilization found for lower percentage of cryoprotectant (e. g. ≤15% for 60 mM NaCl; ≤10% for 40 mM NaCl; ≤5% for 20 mM NaCl). Within the investigated range, there was no difference found between sucrose and trehalose.

Figure 29:
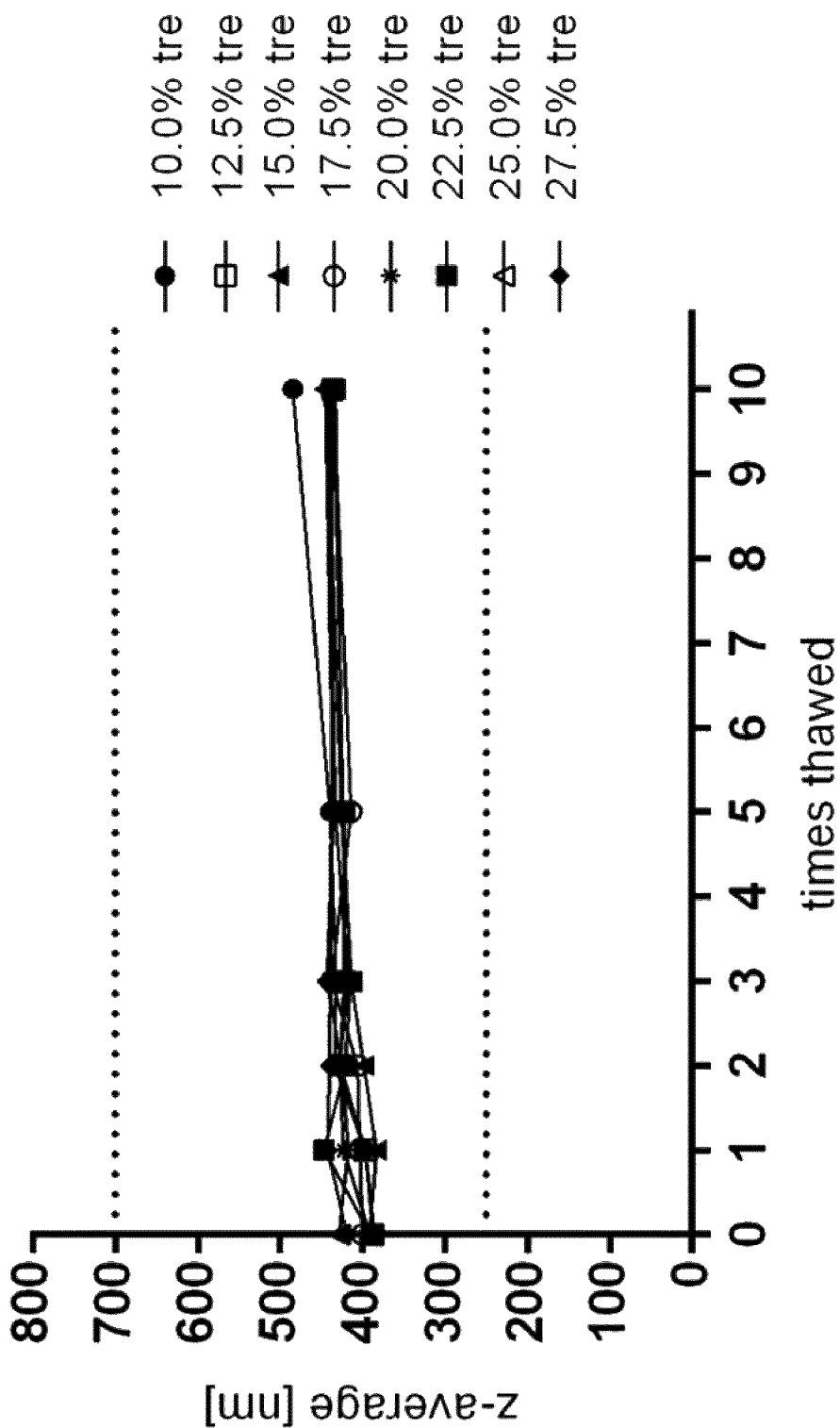
FIG. 29 shows measurements of particle size in RNA lipoplex formulations containing 50 mM NaCl and various amounts (% w:v) of Trehalose dihydrate after multiple freeze thaw cycles.
Figure 30:
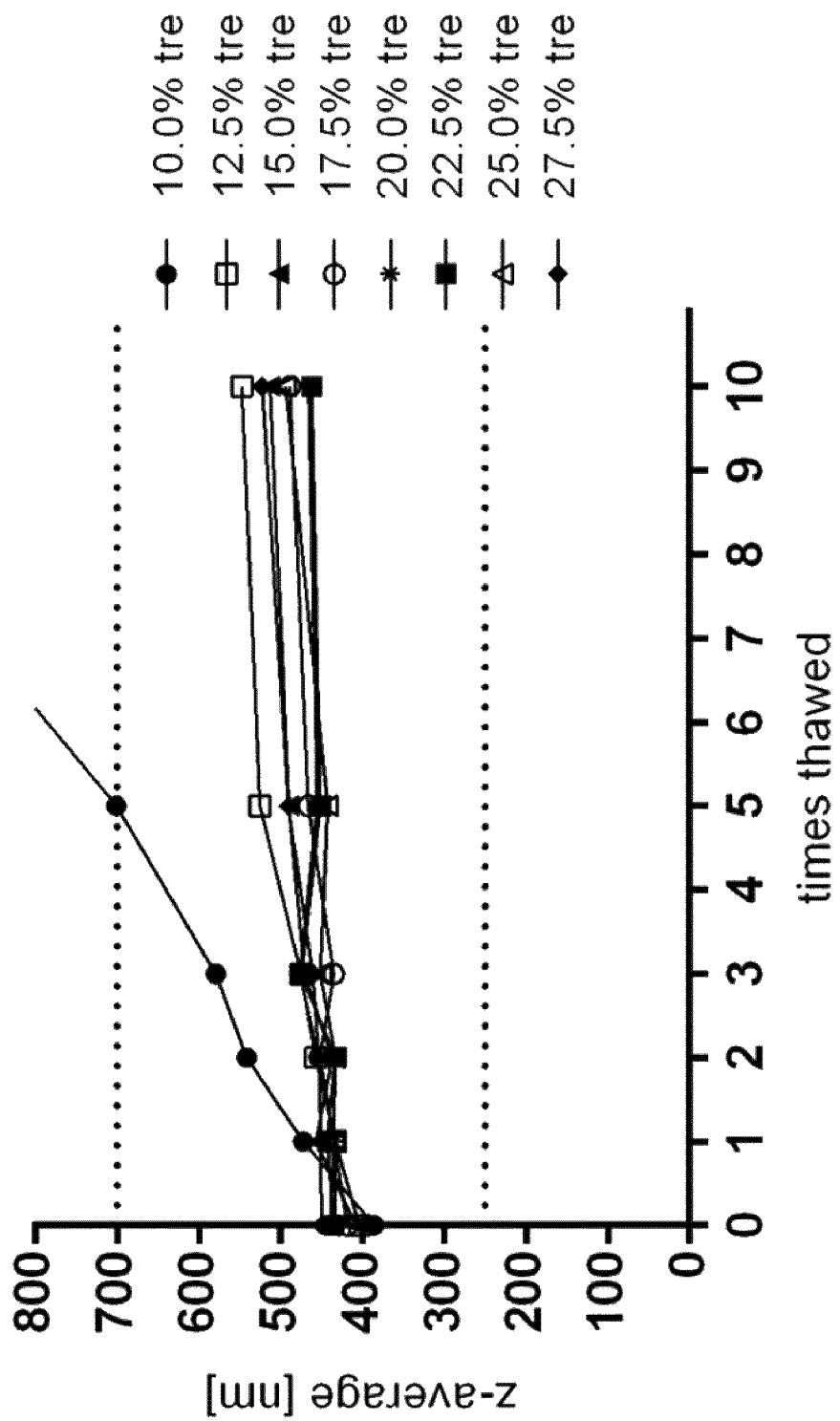
FIG. 30 shows measurements of particle size in RNA lipoplex formulations containing 70 mM NaCl and various amounts (% w/v) of trehalose dihydrate after multiple freeze thaw cycles.
Figure 31:
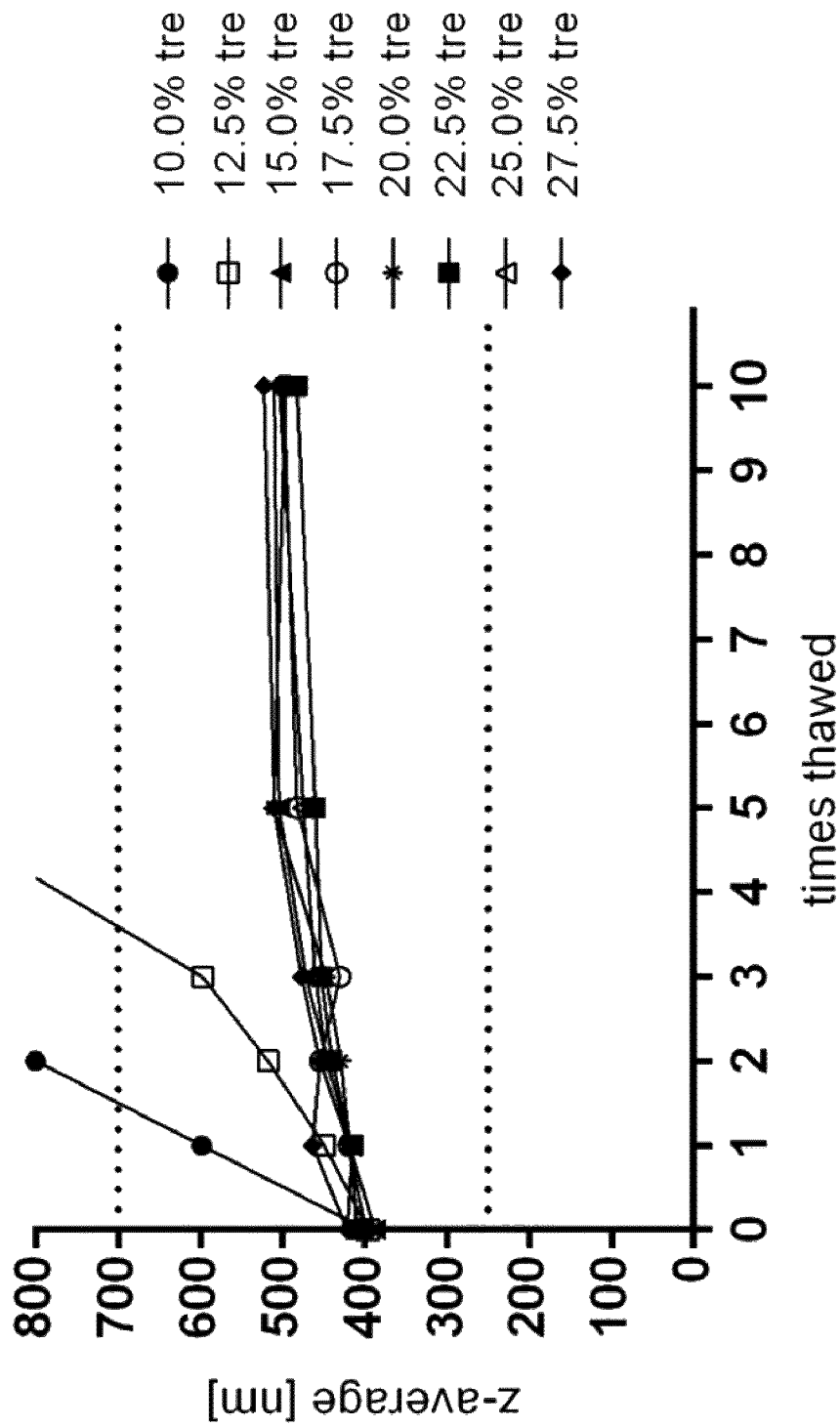
FIG. 31 shows measurements of particle size in RNA lipoplex formulations containing 90 mM NaCl and various amounts (% w/v) of trehalose dihydrate after multiple freeze thaw cycles.

When analyzing the particle size of RNA lipoplexes after 1, 2, 3, 5, and 10 times freezing in the presence of the combinations of NaCl and Trehalose shown in Table 9.3.2, the following results were obtained. Whereas at a concentration of 50 mM NaCl≥12.5% trehalose was sufficient for stabilization of RNA lipoplex particle characteristics even after 10 times freezing (FIG. 29), at 70 mM of NaCl≥12.5% were required for minimum stabilization and ≥22.5% were required for exact preservation of the particle size (FIG. 30). At 90 mM NaCl, ≥15.0% trehalose were required for minimum stabilization and exact preservation of the particle size could not be achieved even with the highest investigated concentration of 27.5% (FIG. 31).

Example 25: Combination of Salt and Cryoprotectants for Long Term Storage

For long-term storage at the given temperature, the combinations of NaCl and cryoprotectant listed in table 9 should be used.

Methods:
To investigate the minimum content of cryoprotectant for long-term storage at −15 to −30° C. at a certain concentration of NaCl, RNA lipoplexes were frozen in the presence of combinations of NaCl and either sucrose or trehalose. The samples were frozen at −30° C. and then transferred to the respective temperature for long-term storage (either −15 or −30° C.). After defined storage time, samples were analyzed and preservation of the colloidal stability was analyzed by measuring the particle size using PCS.

Figure 32:
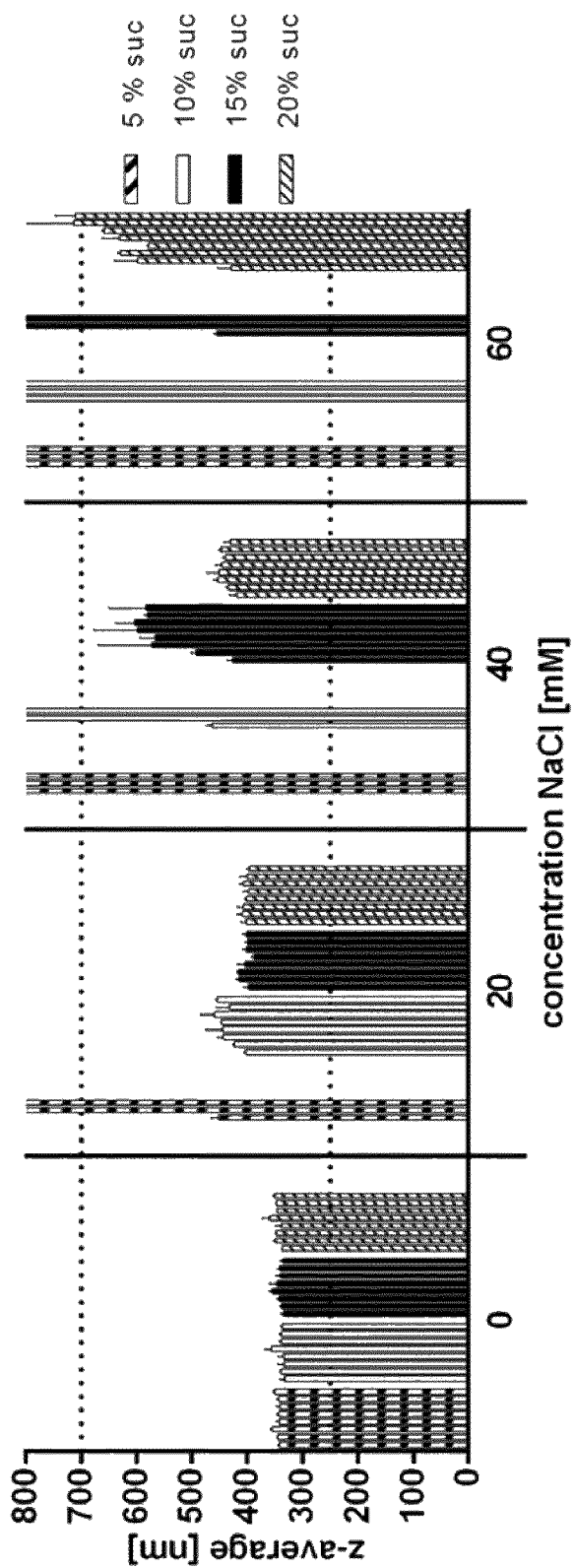
FIG. 32 shows measurements of particle size in RNA lipoplex formulations containing 5-20% w/v sucrose and various low NaCl concentrations after storage at −15° C. for 8 months. The different bars indicate increasing storage periods from left (0 month) to right (8 month). At sucrose/NaCl combinations with less than 8 bars, the particles size exceeded specifications at two following time points and the analysis was stopped.
Figure 33:
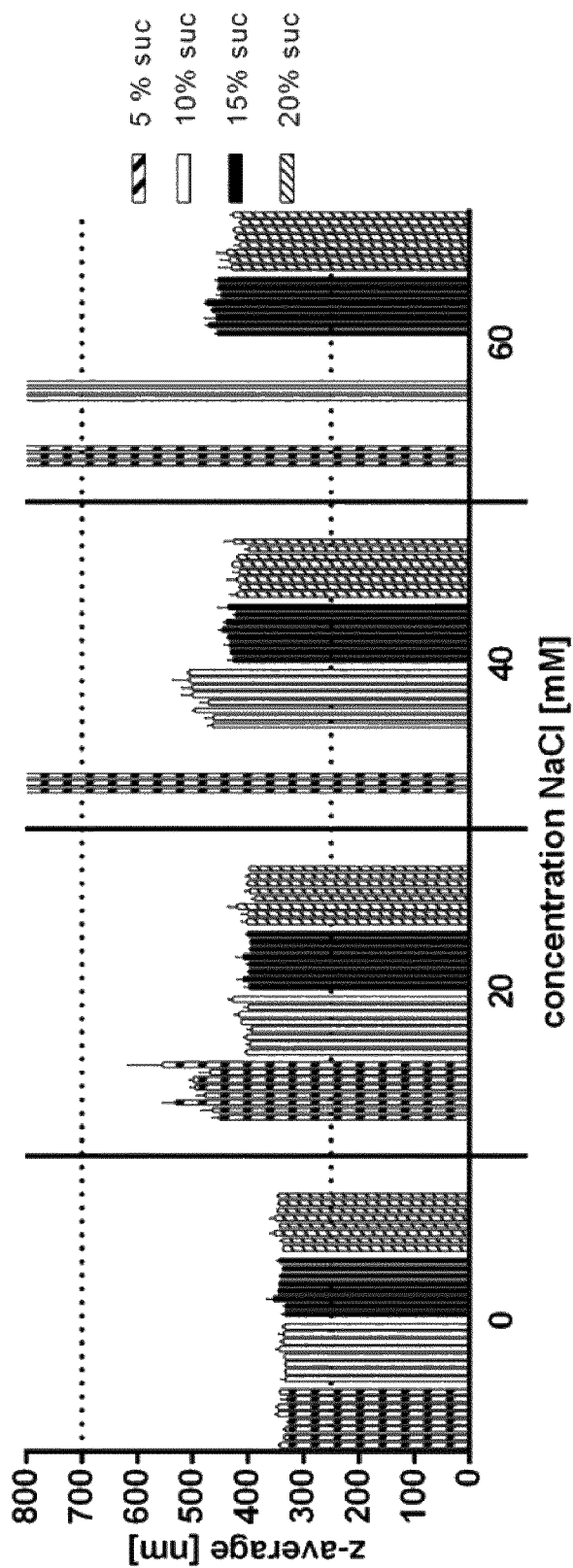
FIG. 33 shows measurements of particle size in RNA lipoplex formulations containing 5-20% w/v sucrose and various low NaCl concentrations after storage at −30° C. for 8 months. The different bars indicate increasing storage periods from left (0 month) to right (8 month). At sucrose/NaCl combinations with less than 8 bars, the particles size exceeded specifications at two following time points and the analysis was stopped.
Figure 34:
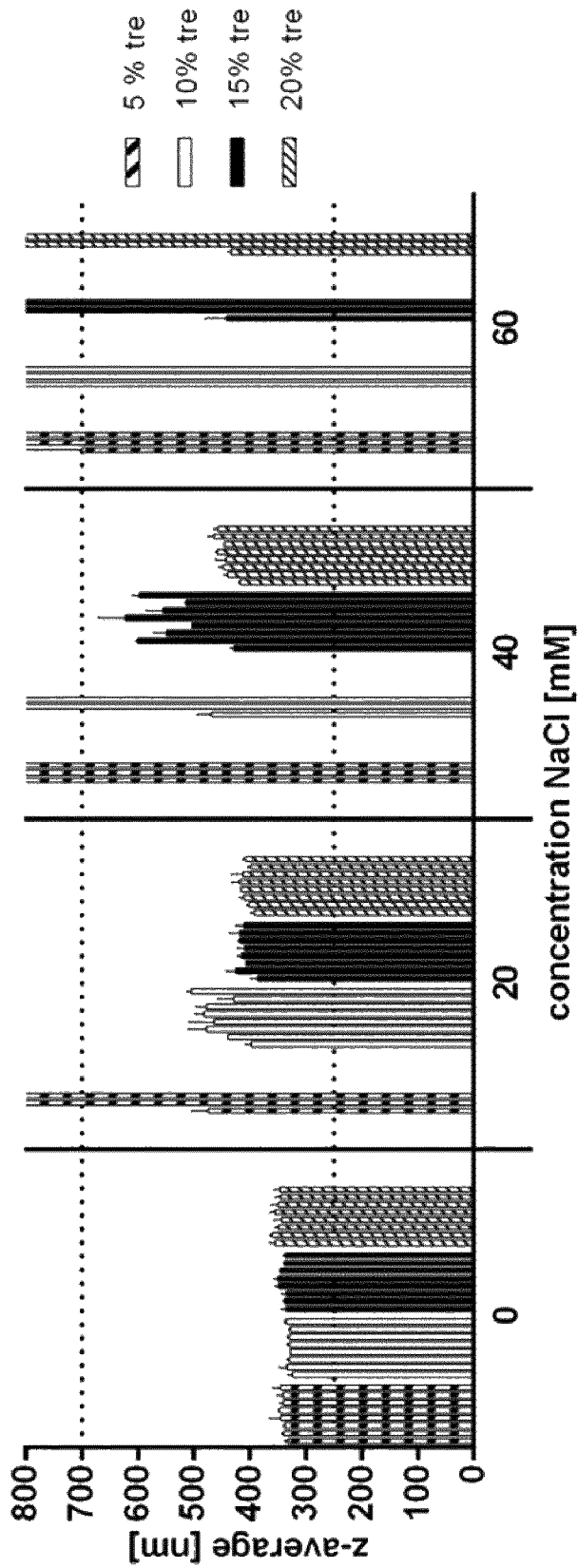
FIG. 34 shows measurements of particle size in RNA lipoplex formulations containing 5-20% w/v trehalose dihydrate and various low NaCl concentrations after storage at −15° C. for 8 months. The different bars indicate increasing storage periods from left (0 month) to right (8 month). At trehalose/NaCl combinations with less than 8 bars, the particles size exceeded specifications at two following time points and the analysis was stopped.
Figure 35:
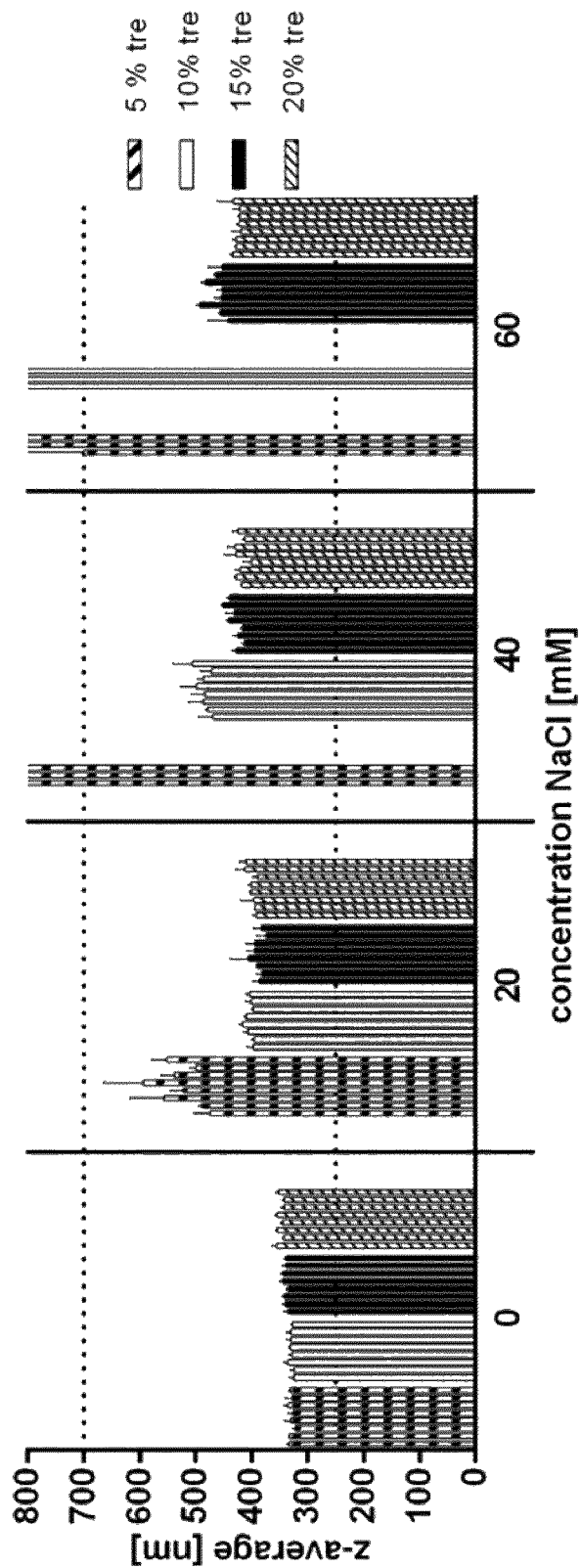
FIG. 35 shows measurements of particle size in RNA lipoplex formulations containing 5-20% w/v trehalose dihydrate and various low NaCl concentrations after storage at −30° C. for 8 months. The different bars indicate increasing storage periods from left (0 month) to right (8 month). At trehalose/NaCl combinations with less than 8 bars, the particles size exceeded specifications at two following time points and the analysis was stopped.

Results:
Whereas particles characteristics of RNA lipoplexes could be preserved during freezing in the presence of up to 70 mM NaCl, an additional effect contributing to destabilization of the colloidal stability could be observed in these experiments. Also acceptable stabilization of the particle characteristics was confirmed after freezing for e. g. a combination of 60 mM NaCl and 20% sucrose, over time the particle size of these formulations increased significantly (FIGS. 32 and 33) at a storage temperature of −15° C. This effect was reduced upon storage at −30° C. (FIGS. 34 and 35).

The stability of RNA lipoplexes at a given NaCl content depends on the amount of cryoprotectant. The amount of cryoprotectant needed to stabilize increases with increasing content of salt within the storage solution. This effect is independent of the sugar type used as cryoprotectant. Compositions of RNA lipoplexes for long-term storage in the frozen state at −15 or −30° C. should contain the content of cryoprotectant listed in table 9.

TABLE 9

The maximum acceptable NaCl concentrations in combination with in the content of cryoprotectant (either sucrose or trehalose) for storage at −15 C and −30 C.

|  | Cryoprotectant (% w:v) | |
| --- | --- | --- |
| NaCl (mM) | Storage at −15° C. | Storage at −30° C. |
| 0 | ≥5 | ≥5 |
| 20 | ≥15 | ≥10 |
| 40 | ≥20 | ≥15 |
| 60 | insufficient stabilization | ≥20 |

Example 26: Long Term Storage with Different Cryoprotectants

Stabilization over 9 month in the presence of 22% (w:v) mono- or bimolecular sugars is possible with 10 to 40 mM NaCl. These formulations can be frozen at −15 to −40° C. and can be kept at the respective temperature for long-term storage. In the presence of 12.6 to 16.8% (w:v) dextran, 10 to 30 mM NaCl are feasible.

Method:
To investigate the minimum content of representative cryoprotectants as sucrose, trehalose, glucose and mixtures including dextran required for long-term storage at −20° C., RNA lipoplexes were frozen at a fixed cryoprotectant content in combination with varying NaCl concentrations. For monomeric or dimeric molecular cryoprotectants as glucose, sucrose, and trehalose a concentration of 22% (w:v) was adjusted. These formulations were frozen and stored at −15 to −40° C. and long-term stability was investigated by measuring the particle size using PCS after defined storage time.

For formulations containing mixtures of the polymer dextran the compositions listed in table 9.5.1 were adjusted. The samples were frozen and stored at −20° C. After defined storage time, samples were analyzed and preservation of the colloidal stability was analyzed by measuring the particle size.

Figure 36:
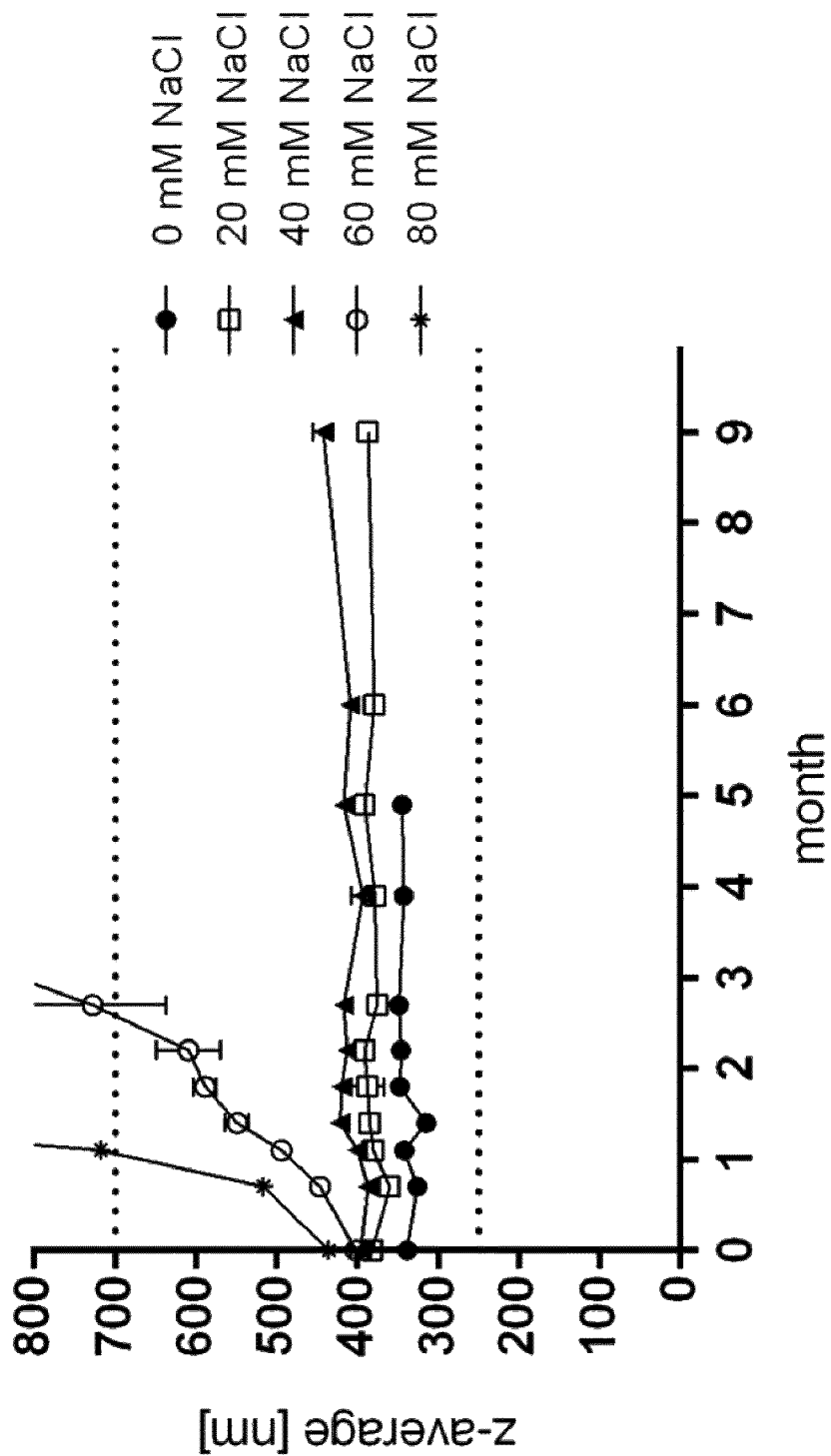
FIG. 36 shows measurements of particle size in RNA lipoplex formulations containing 22% w/v sucrose and various low NaCl concentrations after storage at −20° C.
Figure 37:
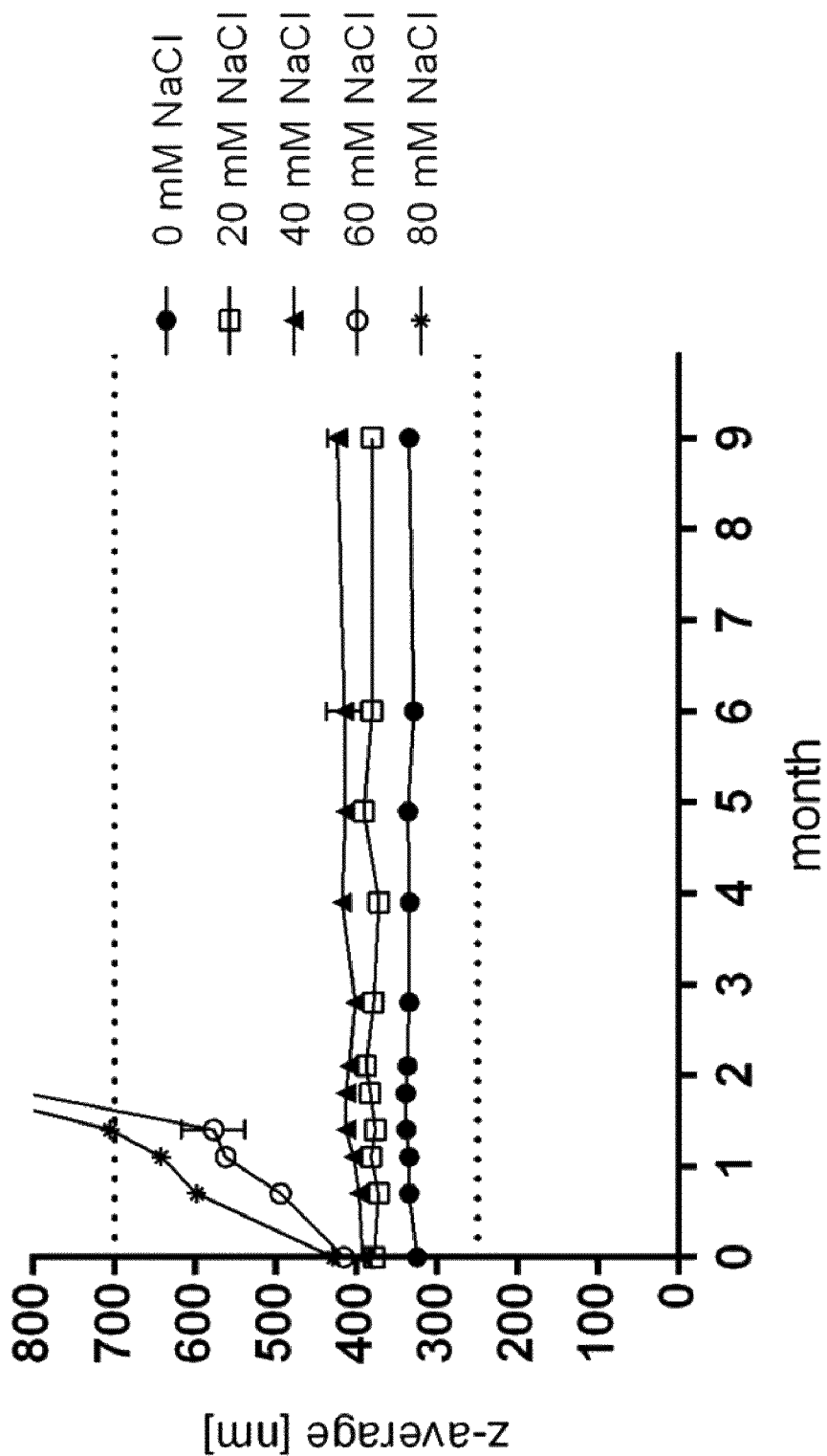
FIG. 37 shows measurements of particle size in RNA lipoplex formulations containing 22% w/v trehalose dihydrate and various low NaCl concentrations after storage at −20° C.
Figure 38:
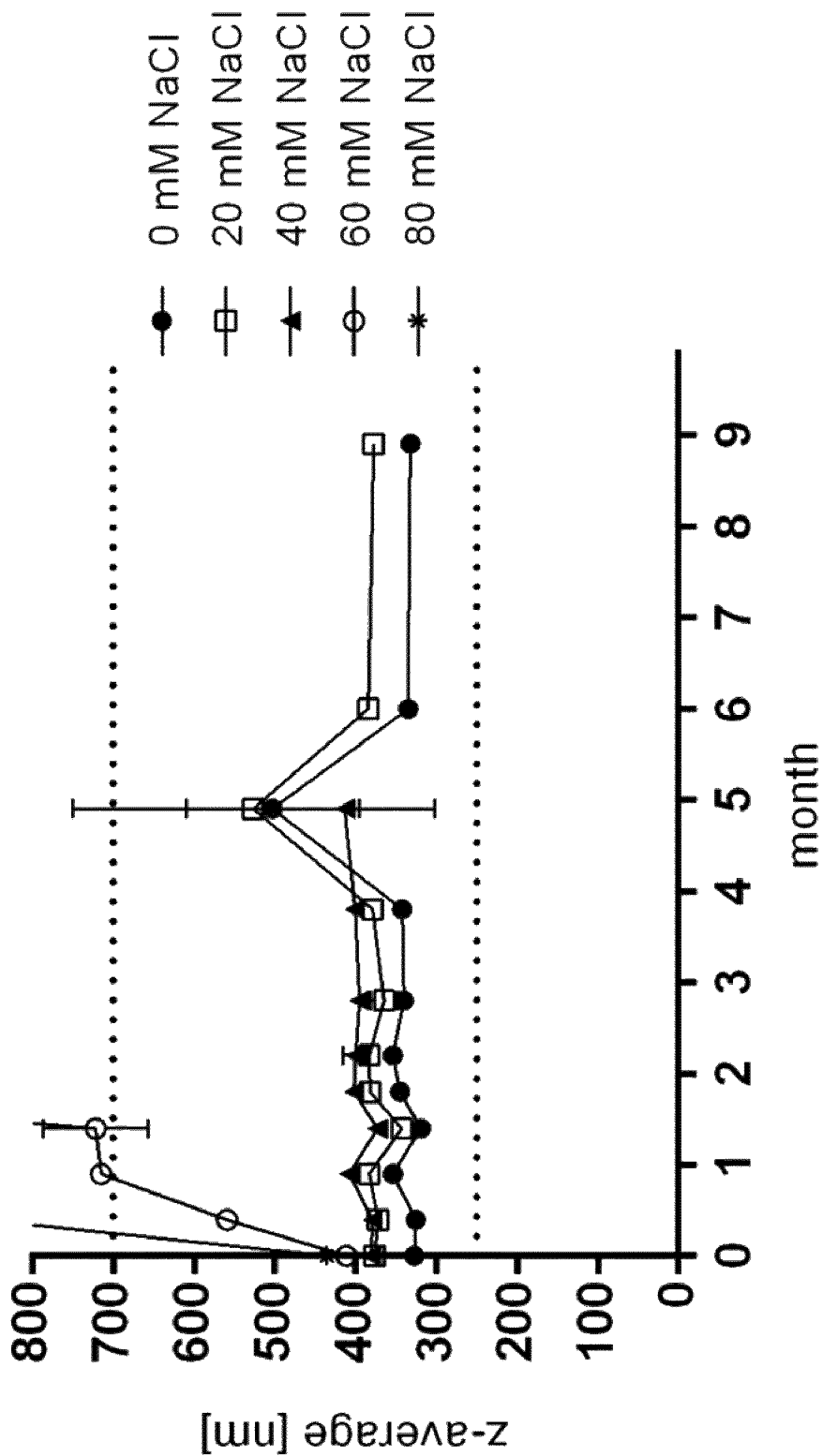
FIG. 38 shows measurements of particle size in RNA lipoplex formulations containing 22% w/v glucose and various low NaCl concentrations after storage at −20° C.
Figure 39:
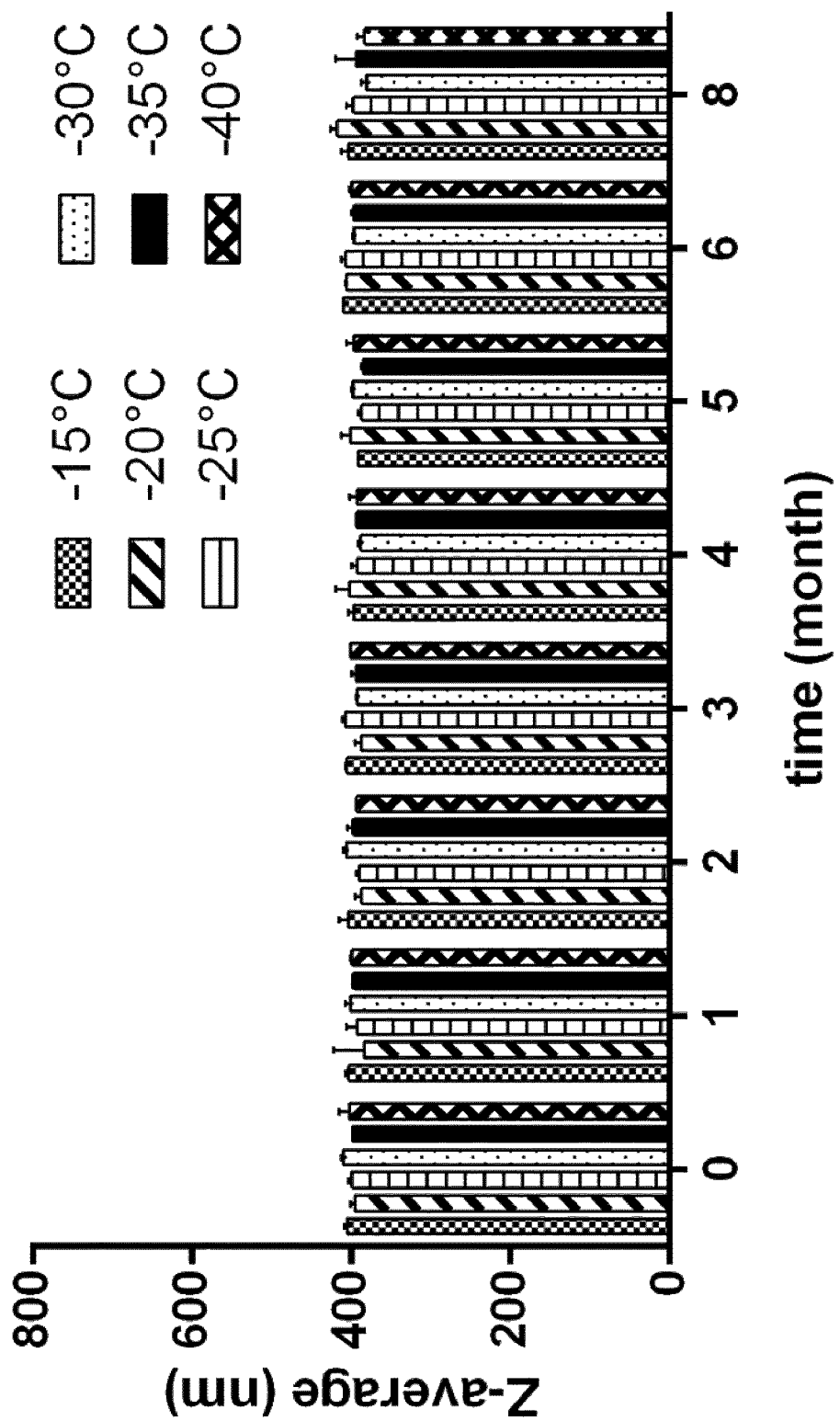
FIG. 39 shows measurements of particle size in RNA lipoplex formulations containing 22% w/v glucose and 20 mM NaCl being frozen and stored at −15 to −40° C.

Results:
For all investigated monomeric or dimeric molecular cryoprotectants, a maximum NaCl concentration was found which should not be exceeded in order to ensure long-term stabilization of RNA lipoplexes in the frozen state. Whereas 60 and 80 mM of NaCl resulted in fast destabilization of lipoplexes, colloidal properties could be preserved for minimum 9 month when the NaCl concentration was ≤40 mM when being stored at −20° C. (Table 10 and FIGS. 36 to 38). No difference in the stabilization efficacy could be found for sucrose, trehalose and glucose. For a formulation including 20 mM NaCl, no difference in long-term stability was found when samples were frozen and stored at −15 to −40° C. (FIG. 39).

Figure 40:
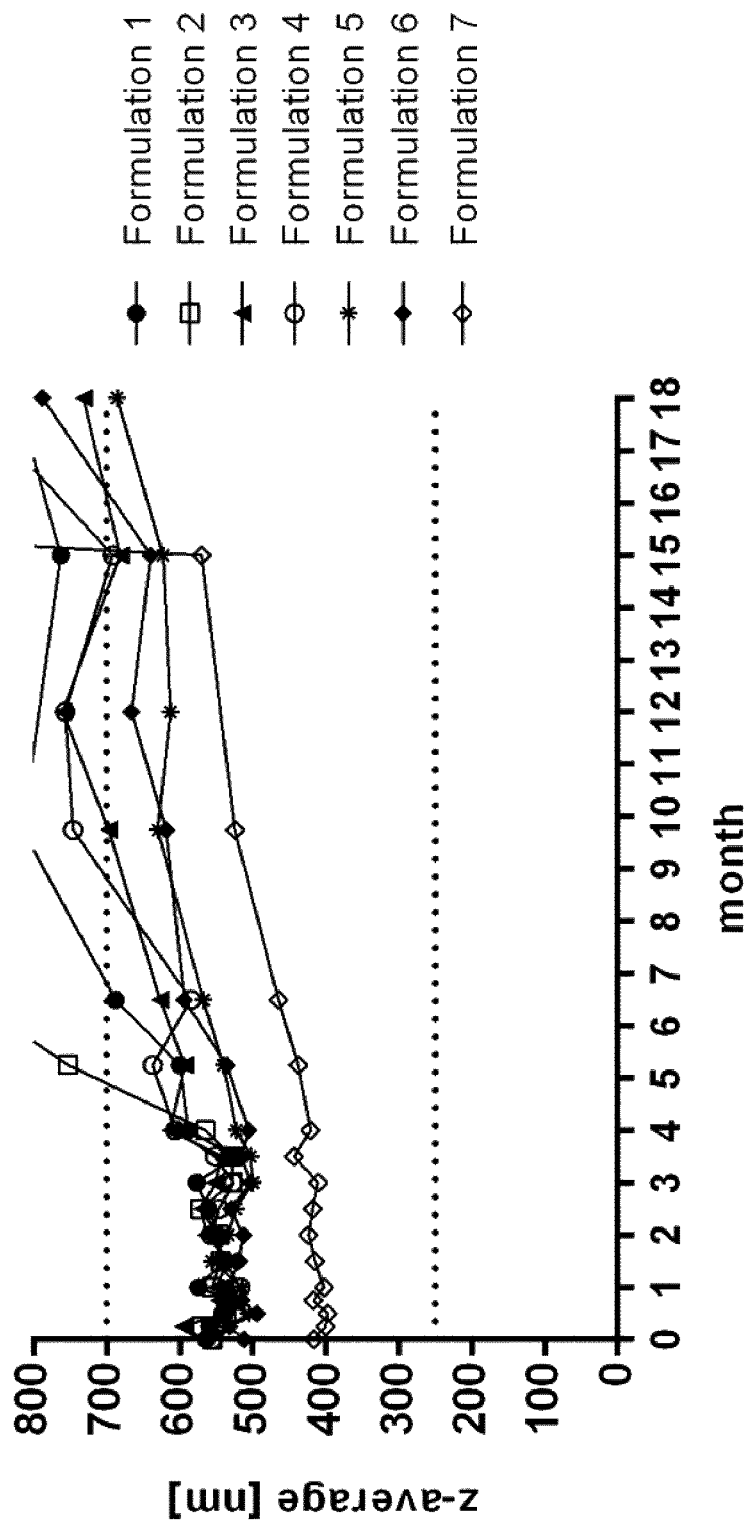
FIG. 40 shows measurements of particle size of RNA lipoplexes frozen in compositions containing the combinations of cryoprotectants listed in Table 10 after storage at −20° C.

As formulations containing dextran were investigated with lower cryoprotectant content (12.6 to 16.8% (w:v)), the efficacy of the stabilization is comparable or better when being compared to mono- or bimolecular sugars (FIG. 40).

TABLE 10

Composition of formulation 1 to 7 containing dextrans (see FIG. 40).

| Formulation | Conc. NaCl (mM) | Dextran 40 (% w:v) | Co-Stabilizer | Co-Stabilizer content (% w:v) |
|---|---|---|---|---|
| Formulation 1 | 90 | 10.0 | Dextran 1 | 4.4 |
| Formulation 2 | 90 | 10.0 | Trehalose | 2.6 |
| Formulation 3 | 70 | 10.0 | Dextran 1 | 6.3 |
| Formulation 4 | 70 | 10.0 | Trehalose | 3.1 |
| Formulation 5 | 50 | 8.0 | Dextran 1 | 8.8 |
| Formulation 6 | 50 | 8.0 | Trehalose | 4.7 |
| Formulation 7 | 40 | 0 | Dextran 1 | 12.9 |

Example 27: Freeze-Drying a) Freeze Thawing

Figure 41:
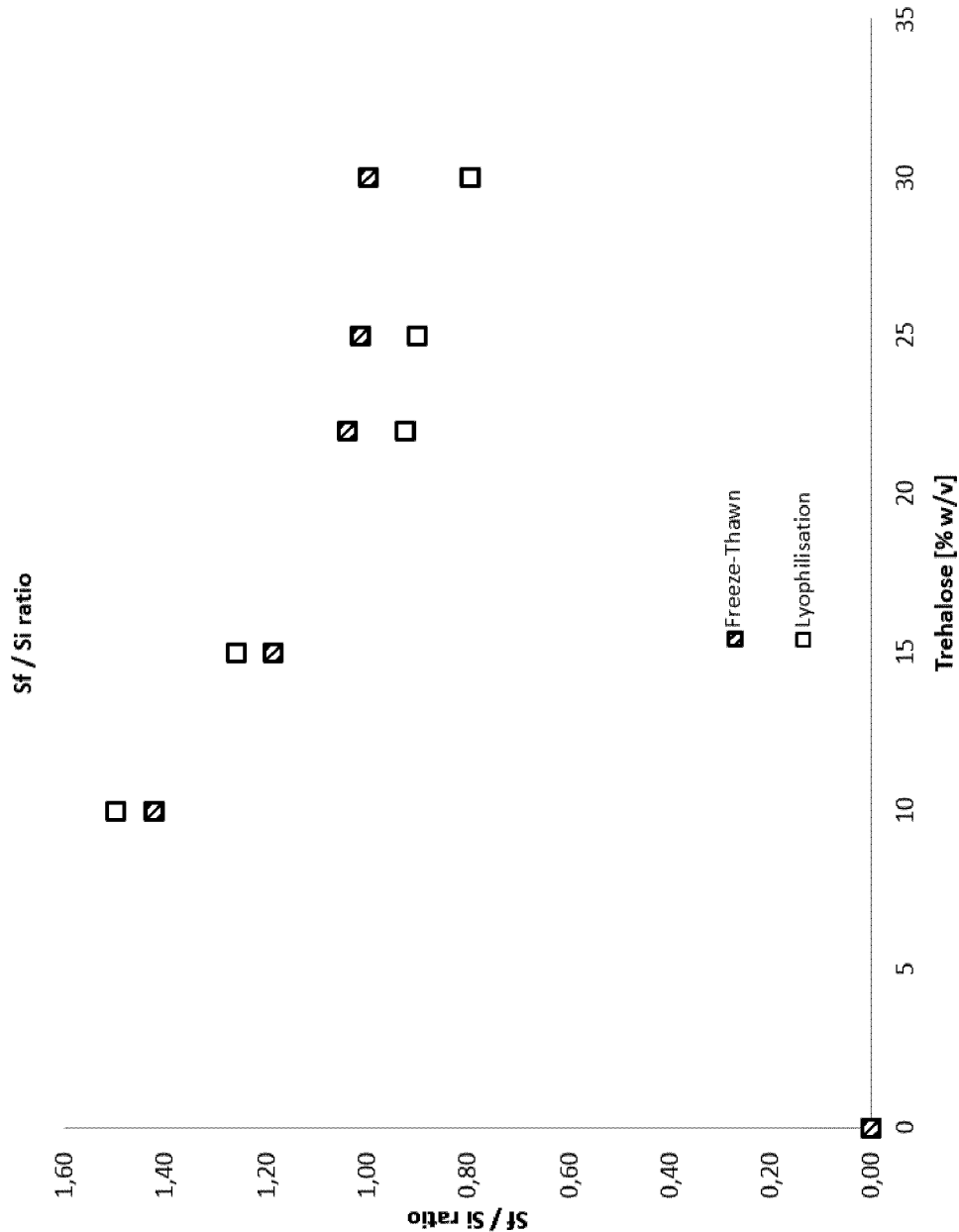
FIG. 41 shows the effect of trehalose concentration in the RNA lipoplex formulations [RNA (lip)] formulation after freeze-thaw or after freeze-drying and reconstitution.

In order to determine the most effective cryo/lyoprotectant concentration freeze-thawing studies were performed. The RNA lipoplex formulations were freeze-thawed in 5 mM HEPES, 80 mM NaCl, 2.6 mM EDTA with the addition of 10%, 15%, 20%, 25% and 30% trehalose. Particle size was determined before and after storage at −20° C. Particle aggregation was observed in formulations frozen in absence of trehalose and their particle size was not determined. According to FIG. 41, formulations frozen with cryo/lyoprotectant showed concentration dependent cryoprotection, the particle size increased at lower lyo/cryoprotectant concentrations. At 22% w/v trehalose, only a minimal increase in particle size was observed with a Sf/Si (Sf=final size, Si=initial size) of 1.04, which being less than 1.3 is still considered acceptable. At lower trehalose concentrations, Sf/Si ratios were higher. The Sf/Si ratios obtained from the freeze-thawing studies correlated with the Sf/Si ratios obtained from the same formulations after freeze-drying and reconstitution.

b) Reconstitution and Particle Stability

RNA lipoplex formulations prepared in 5 mM HEPES, 2.6 mM EDTA, 0 mM, 10 mM, 20 mM, 30 mM, 40 mM, 50 mM, 60 mM. 80 mM NaCl and 5%, 10%, 15% and 22% Trehalose were freeze-dried. All freeze-dried samples exhibited good cake appearance. The samples were reconstituted in the original volume with 0.9% NaCl solution. All freeze-dried RNA lipoplex formulations instantly dissolved upon reconstitution with 0.9% NaCl solution or WFI. Particle size change in freeze-dried RNA lipoplex formulations prepared in 22% trehalose after reconstitution with 0.9% NaCl solution or water was determined.

Figure 42:
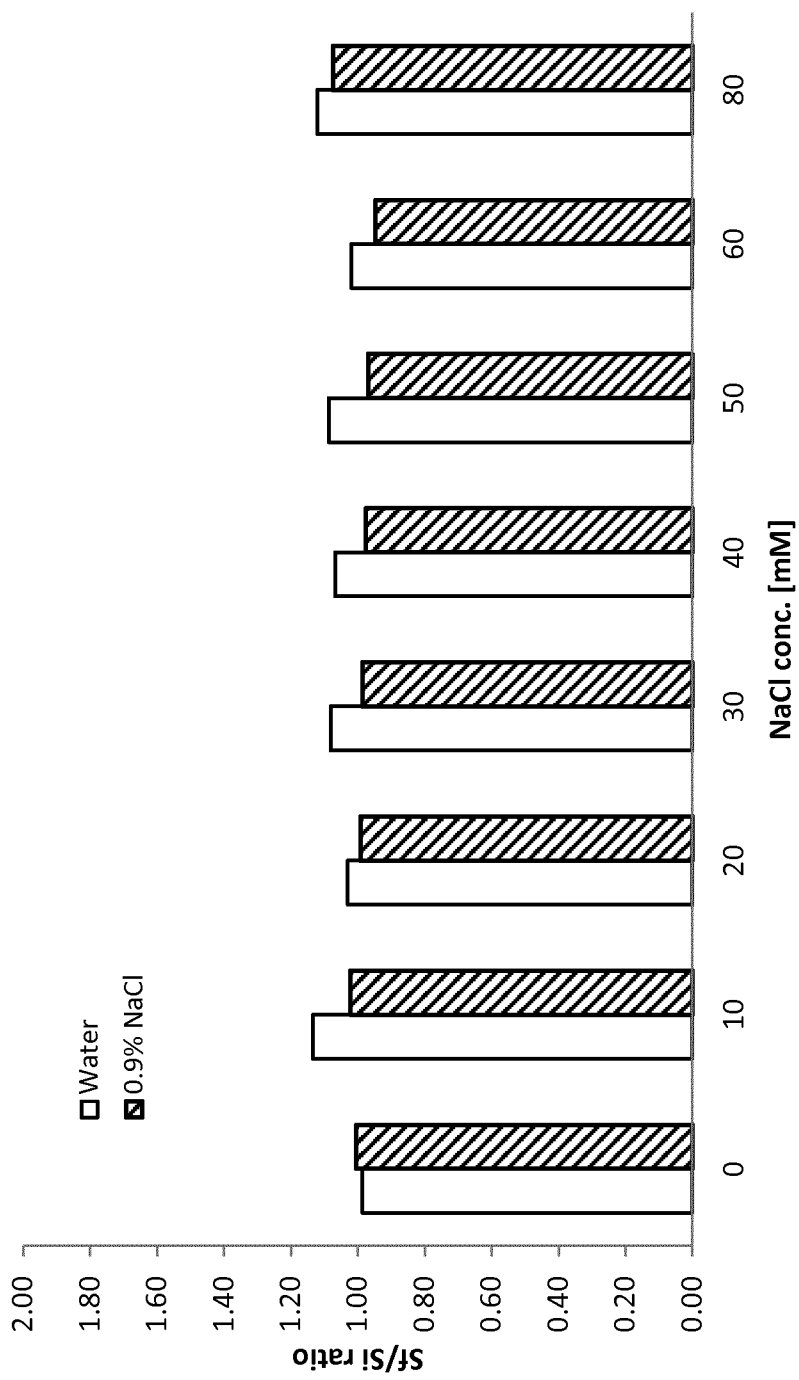
FIG. 42 shows the particle size change in freeze-dried RNA(lip) formulations prepared in 22% trehalose after reconstitution with 0.9% NaCl solution or WFI (water for injection).

According to FIG. 42, particle size remained stable in all freeze-dried RNA lipoplex formulations containing trehalose after freeze-drying and reconstitution. A slight decrease on the size of the RNA lipoplexes was observed when the freeze-dried samples were reconstituted with 0.9% NaCl in comparison to the freeze-dried samples reconstituted with water. A correlation between the NaCl to trehalose ratio and the particle stability was observed. The size of the RNA lipoplex particles increased in the formulations prepared at lower concentrations of trehalose and higher NaCl concentrations.

c) Cell Culture Experiments with Freeze-Dried RNA Lipoplex Formulations

Figure 43:
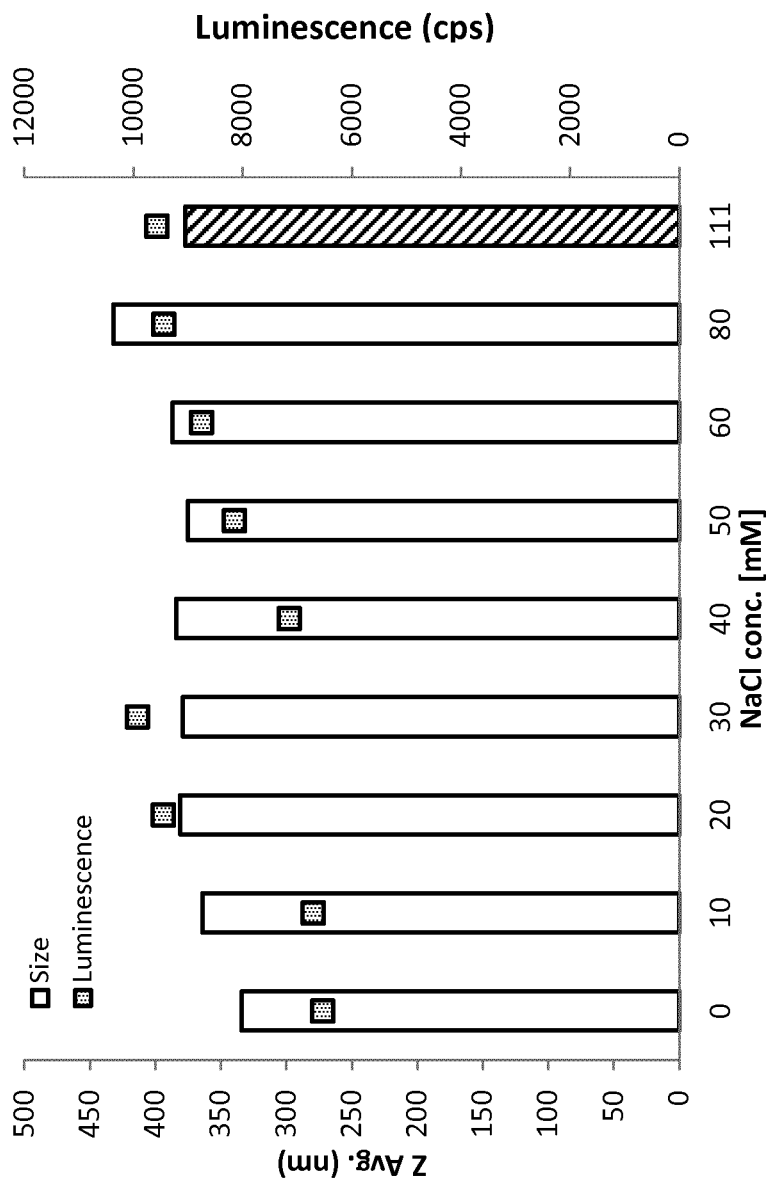
FIG. 43 shows Luc-RNA in-vitro transfection of freeze-dried RNA lipoplex formulations [RNA (lip)] prepared in 22% trehalose at different NaCl concentrations. Freeze-dried samples were reconstituted with 0.9% NaCl solution. (texturized column: liquid control).

In-vitro transfection experiments of freeze-dried luciferase-encoding RNA lipoplex formulations prepared in 22% trehalose at different NaCl concentrations were performed. Freeze-dried samples were reconstituted with 0.9% NaCl solution According to FIG. 43, freeze-dried RNA lipoplex formulations prepared at 22% trehalose and at different NaCl concentrations showed similar luc-RNA transfection levels in dendritic cells. No correlation between NaCl concentration present in the RNA lipoplex formulation and in-vitro RNA transfection was found. The freeze-dried samples showed a similar or even better luc-RNA transfection in comparison to a fresh RNA lipoplex control.

d) Stability Studies

Freeze-dried RNA lipoplex formulations containing 10% trehalose, 22% trehalose and 0 mM, 20 mM, 40 mM, 60 mM and 80 mM NaCl were investigated for stability studies at 4° C., 25° C. and 40° C. (1 month and 6 months). After reconstitution at the original volume with 0.9% NaCl solution, samples were characterized for particle size and RNA integrity (% full length RNA).

Figure 44:
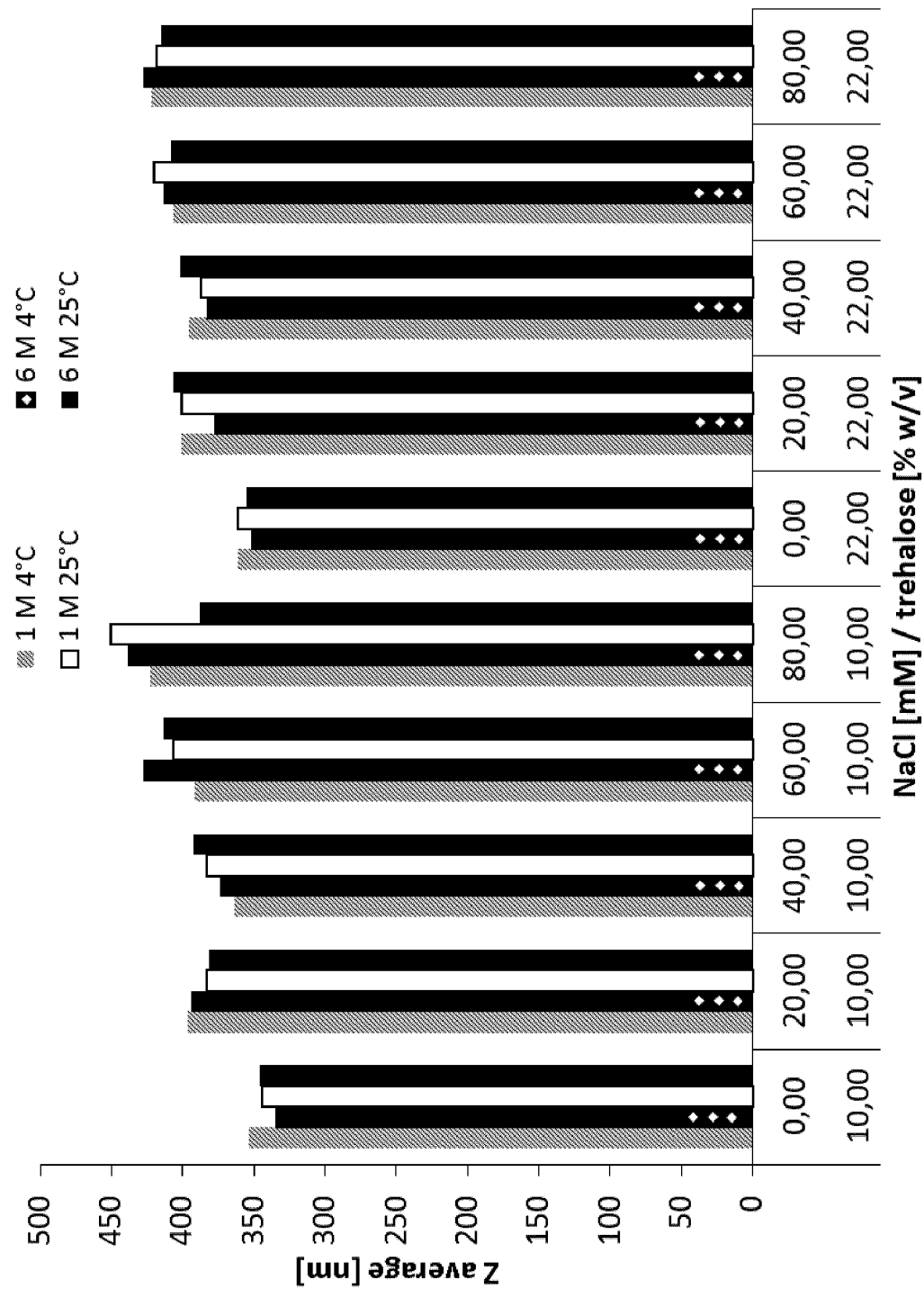
FIG. 44 shows Z-average diameter of freeze-dried RNA lipoplex formulations [RNA (lip)] formulated at different trehalose/NaCl ratios stored at 2-8° C. or 25° C. after reconstitution with 0.9% NaCl solution. The formulations were reconstituted in the original volume after freeze-drying.
Figure 45:
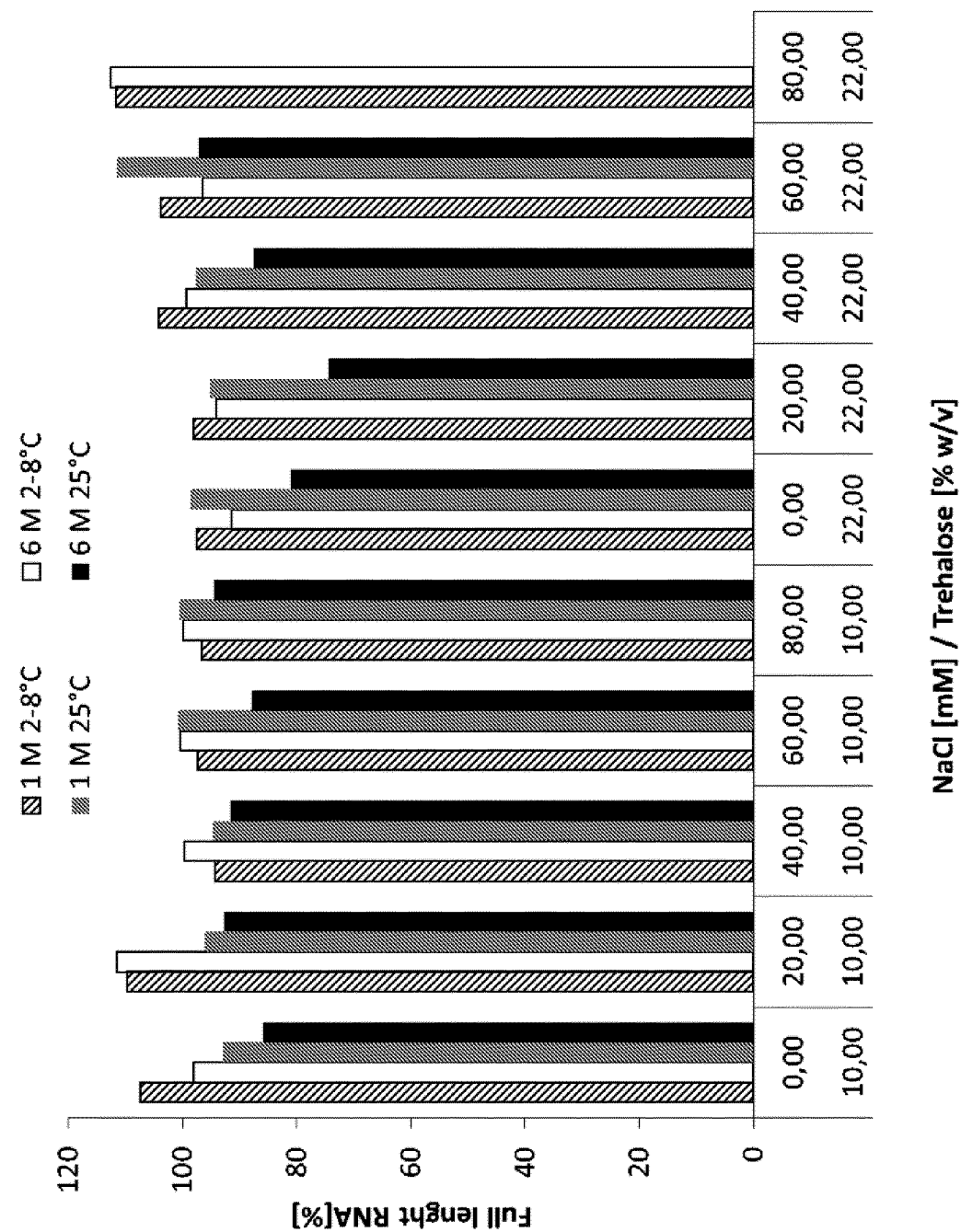
FIG. 45 shows the RNA integrity (% full length RNA) of freeze-dried RNA(lip) formulated at different trehalose/NaCl ratios after reconstitution with 0.9% NaCl solution and stored at 2-8° C. or 25° C. The formulations were reconstituted in the original volume after freeze-drying and diluted 1:1 with 0.9% NaCl solution for the cell culture experiments (0.01 mg/mL RNA).

According to FIGS. 44 and 45, sizes of the different RNA lipoplexes did not significantly change over the time independent of the formulation or storage temperature. Interestingly, lower amounts of cryoprotectant (e.g. 10%) are sufficient to maintain the particle stability in the freeze-dried formulation whereas a higher amount (e.g. 22%) is required in the case of the frozen formulation. RNA integrity (% full length RNA) in the freeze-dried samples after 6 months storage at 4° C. varied between 94% and 100% and for the RNA(lip) formulations stored at 25° C. varied between 85% and 94%. However, no correlation with trehalose to NaCl concentration ratio or storage time was identified.

The invention claimed is:

1. A method for continuous flow manufacturing of RNA lipoplex particles comprising:
   mixing, in a continuous-flow fluidic system other than a microfluidic system, (i) a first solution comprising RNA and having an ionic strength as achieved by NaCl at a concentration within a range of about 50 mM to about 300 mM; and (ii) a second solution comprising liposomes which comprise 1,2-di-O-octadecenyl-3-trimethylammonium propane (DOTMA) and 1,2-di-(9Z-octadecenoyl)-sn-glycero-3-phosphoethanolamine (DOPE), under controlled mixing conditions of the RNA and the liposomes such that RNA lipoplex particles having an average diameter within a range of about 300 nm to about 500 nm and a polydispersity index of smaller than 0.2 are manufactured,
   wherein the combined flow of the first solution and the second solution is characterized by a Reynolds number of greater than 300.

2. The method of claim 1, wherein the solution comprising liposomes is a liposome colloid.

3. The method of claim 2, wherein the liposomes in the liposome colloid have an average diameter of at least about 250 nm.

4. The method of claim 2, wherein the liposomes in the liposome colloid have an average diameter that ranges from about 250 nm to about 800 nm.

5. The method of claim 1, wherein a molar ratio of DOTMA and DOPE is from about 4:1 to about 1:2, from about 3:1 to about 1:1, or about 2:1.

6. The method of claim 2, wherein the liposome colloid is produced by a method comprising a step of injecting into an aqueous phase a lipid solution comprising lipids in ethanol, wherein at least one of the lipids is present in the lipid solution at a concentration that corresponds to or is higher than the equilibrium solubility of the at least one lipid alone in ethanol, wherein the lipids comprise DOTMA and DOPE.

7. The method of claim 1, wherein the first solution and the second solution are aqueous solutions.

8. The method of claim 1, wherein the combined flow of the first solution and the second solution is characterized by a Reynolds number from about 500 to about 2100.

9. The method of claim 1, wherein the controlled mixing conditions comprise controlling a mixing ratio of the first solution and the second solution.

10. The method of claim 1, wherein the controlled mixing conditions comprise controlling relative volumes of the first solution—and the second solution which are to be mixed.

11. The method of claim 9, wherein identical volumes (v/v) of the first solution and the second solution are mixed.

12. The method of claim 1, wherein clogging of the continuous-flow fluidic system is avoided.

13. The method of claim 12, wherein the RNA lipoplex particles are characterized by presence of a single Bragg peak in an X-ray scattering pattern at about 1 $nm^{-1}$, wherein the peak width is smaller than 0.2 $nm^{-1}$.

14. The method of claim 12, wherein the continuous-flow fluidic system comprises a Y-type or T-type mixing element.

15. The method of claim 14, wherein the Y-type or T-type mixing element has a diameter of from about 1.2 mm to about 50 mm.

16. The method of claim 1, wherein the continuous-flow fluidic system comprises a syringe pump, a first syringe comprising the first solution, and a second syringe comprising the second solution, wherein the first syringe and the second syringe are placed in parallel in the same syringe pump.

17. The method of claim 1, wherein the continuous-flow fluidic system comprises a pumping system with flow rate sensors, wherein the pumping system comprises a pressurized vessel, a membrane pump, a gear pump, a magnetic levitation pump, or a peristaltic pump.

18. The method of claim 17, wherein the flow rate sensors comprise elements that provide feedback-loop for online-control and real-time adjustment of flow rates.

19. The method of claim 1, wherein a mixture produced from the mixing of the first solution and the second solution has an ionic strength of at least about 50 mM.

20. The method of claim 1, wherein the RNA encodes a peptide or protein comprising at least one epitope.

21. The method of claim 1, wherein a ratio of positive charges to negative charges in the RNA lipoplex particles is from about 1:2 to about 1.9:2, or about 1.3:2.0.

22. The method of claim 14, wherein a ratio of the combined flow rate of the first solution and the second solution—to a diameter of the mixing element is at least 150 $cm^2$/min.

23. The method of claim 1, wherein a mixture produced from the mixing of the first solution and the second solution has an ionic strength of at least about 45 mM.

24. The method of claim 1, wherein a ratio of positive charges to negative charges in the RNA lipoplex particles is from about 1:2 to about 2.1:2.

25. The method of claim 1, wherein a ratio of positive charges to negative charges in the RNA lipoplex particles is from about 3:1 to about 5:1.

26. The method of claim 1, wherein the concentration of lipid(s) in the solution comprising liposomes is within a range of about 250 mM to about 550 mM.

27. The method of claim 1, wherein the second solution was prepared without addition of NaCl.

28. The method of claim 1, wherein the first solution has an ionic strength as achieved by NaCl at a concentration within a range of about 75 mM to about 150 mM NaCl.

29. The method of claim 1, wherein the RNA lipoplex particle preferentially targets the spleen upon administration to a patient.

30. The method of claim 1, wherein the RNA lipoplex particle is intended to be administered by intravenous administration.

31. The method of claim 1, wherein, upon intravenous administration of the RNA lipoplex particle intravenously to a patient, the RNA lipoplex particle preferentially targets the spleen of the patient.

\* \* \* \* \*